United States Patent
Goldberg et al.

(10) Patent No.: US 11,740,239 B2
(45) Date of Patent: *Aug. 29, 2023

(54) IDENTIFICATION AND ISOLATION OF HUMAN CORNEAL ENDOTHELIAL CELLS (HCECS)

(71) Applicant: EMMETROPE OPHTHALMICS LLC, Menlo Park, CA (US)

(72) Inventors: Jeffrey L. Goldberg, Menlo Park, CA (US); Noelia J. Kunzevitzky, Menlo Park, CA (US)

(73) Assignee: Emmetrope Ophthalmics LLC, Menlo Park, CA (US)

( * ) Notice: Subject to any disclaimer, the term of this patent is extended or adjusted under 35 U.S.C. 154(b) by 423 days.

This patent is subject to a terminal disclaimer.

(21) Appl. No.: 16/877,176

(22) Filed: May 18, 2020

(65) Prior Publication Data
US 2020/0277572 A1 Sep. 3, 2020

Related U.S. Application Data

(63) Continuation of application No. 14/888,875, filed as application No. PCT/US2014/036616 on May 2, 2014, now Pat. No. 10,655,102.
(Continued)

(51) Int. Cl.
*G01N 33/569* (2006.01)
*G01N 33/50* (2006.01)
*C12N 5/079* (2010.01)

(52) U.S. Cl.
CPC ..... *G01N 33/56966* (2013.01); *C12N 5/0621* (2013.01); *G01N 33/5064* (2013.01)

(58) Field of Classification Search
CPC ......... G01N 33/56966; G01N 33/5064; C12N 5/0621
See application file for complete search history.

(56) References Cited

U.S. PATENT DOCUMENTS

| 10,655,102 | B2* | 5/2020 | Goldberg | G01N 33/5064 |
| 2014/0170751 | A1* | 6/2014 | Hayashi | C12N 5/0621 |
| | | | | 435/402 |
| 2014/0370007 | A1* | 12/2014 | McCabe | A61L 27/3808 |
| | | | | 424/278.1 |

OTHER PUBLICATIONS

Foets et al. A comparative immunohistochemical study of human corneotravecular tissue. Graefe's Arch Clin Exp. Ophthalmol 230: 269-274 (1992).*

(Continued)

*Primary Examiner* — Gailene Gabel
(74) *Attorney, Agent, or Firm* — Rodney J. Fuller; Booth Udall Fuller, PLC

(57) ABSTRACT

The present invention provides methods for the identification, isolation and/or enrichment of human corneal endothelial cells (HCECs). In some embodiments, the method comprises a positive selection process in which a cell population containing human corneal cells is contacted with a positive affinity reagent that selectively binds to HCECs relative to cells other than HCECs (e.g., corneal keratocytes, etc.) in the population and/or a negative selection process in which a cell population containing HCECs is contacted with a negative affinity reagent that selectively binds to cells other than HCECs in the population relative to HCECs. The present invention also provides reagents and kits for the identification, isolation and/or enrichment of HCECs as well as compositions that are enriched in HCECs.

20 Claims, 5 Drawing Sheets

Specification includes a Sequence Listing.

Related U.S. Application Data

(60) Provisional application No. 61/819,146, filed on May 3, 2013.

(56) References Cited

OTHER PUBLICATIONS

Kisselbach et al. CD90 Expression on human primary cells and elimination of contaminating fibroblasts from cell cultures. Cytotechnology 59: 31-44 (2009).*

* cited by examiner

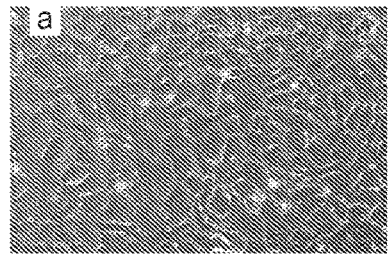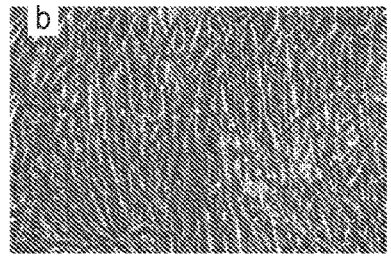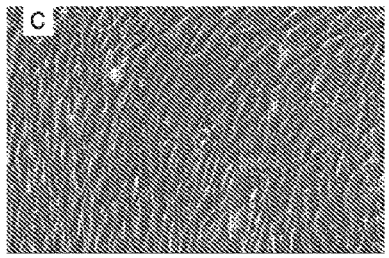
P2 HCEC CULTURE - "GOOD"  
FIG. 1A
P3 HCEC CULTURE - "FIBROBLASTIC"  
FIG. 1B
P3 CORNEAL KERATOCYTE CULTURE  
FIG. 1C
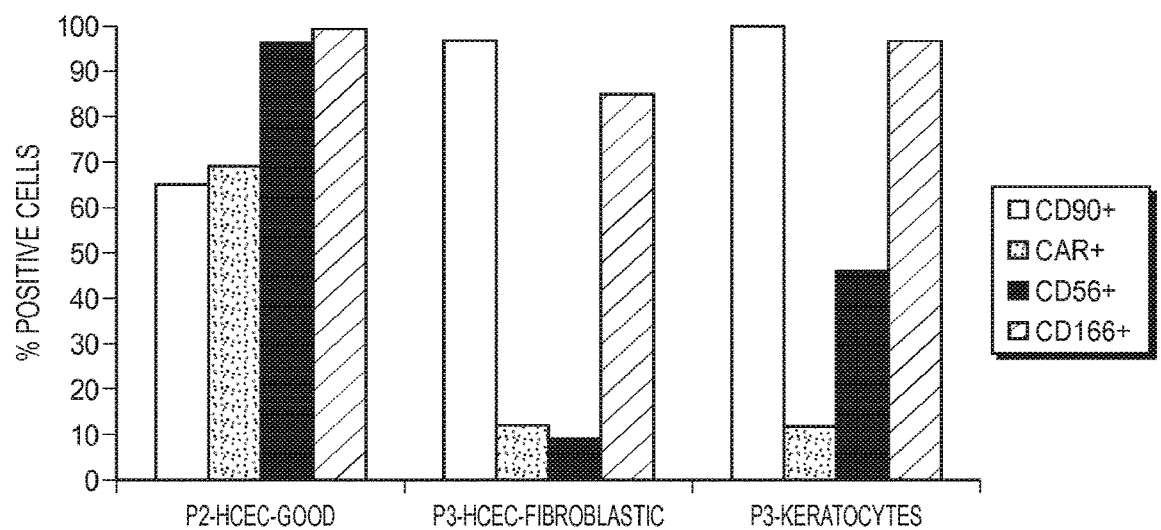
FIG. 2

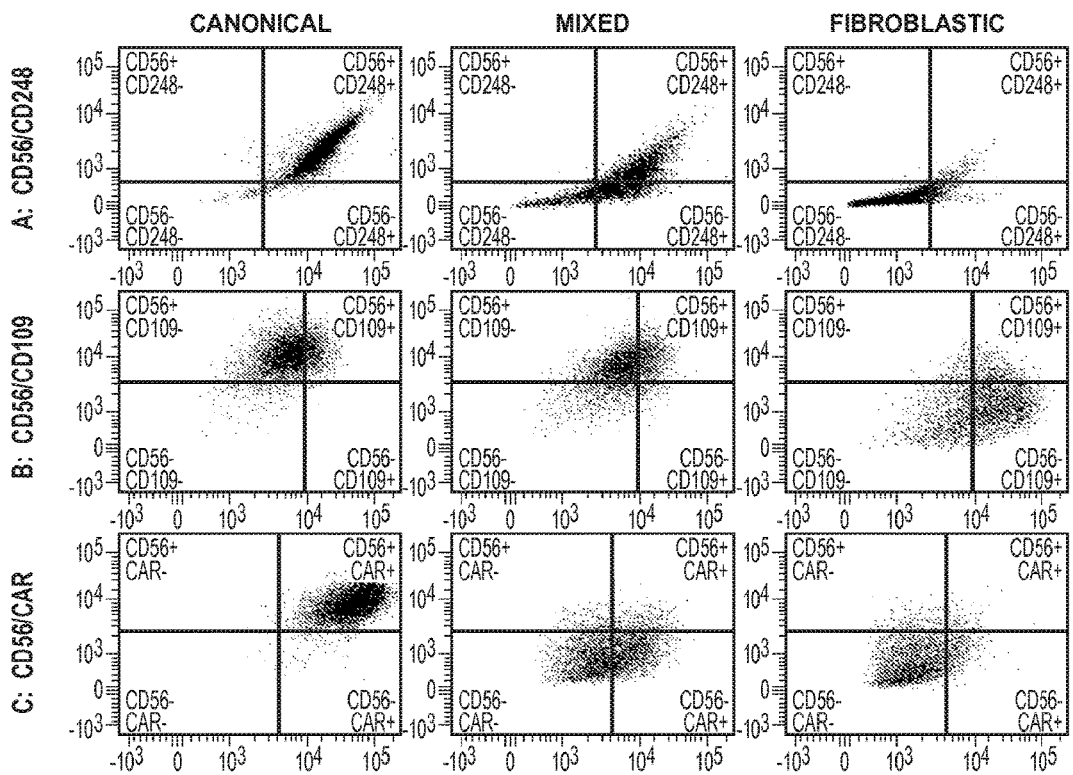
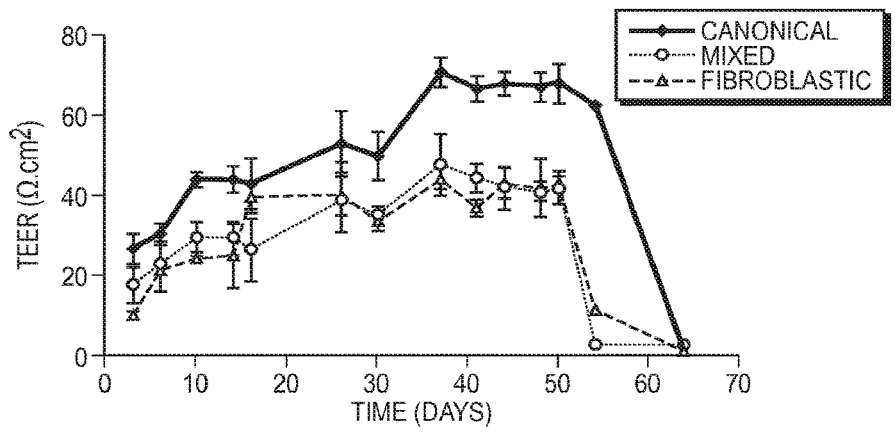
FIG. 7

IDENTIFICATION AND ISOLATION OF HUMAN CORNEAL ENDOTHELIAL CELLS (HCECS)

CROSS-REFERENCE TO RELATED APPLICATIONS

This application is a continuations of U.S. patent application Ser. No. 14/888,875, filed Nov. 3, 2015 (published as US20160102290), which is the U.S. National Stage of International Patent Application No. PCT/US2014/036616, filed May 2, 2014, which claims the benefit of U.S. Patent Application No. 61/819,146, entitled "METHOD FOR IDENTIFYING AND ISOLATING HUMAN CORNEAL ENDOTHELIAL CELLS (HCECS)," filed May 3, 2013, the contents of each of which are hereby incorporated by reference in their entireties.

INCORPORATION-BY-REFERENCE OF MATERIAL ELECTRONICALLY FILED

Incorporated by reference in its entirety herein is a computer-readable nucleotide/amino acid sequence listing submitted concurrently herewith and identified as follows: One 821,867 byte ASCII (text) file named "Seq_List" created on Aug. 13, 2018.

BACKGROUND OF THE INVENTION

When the innermost layer of the cornea, the endothelium, is damaged, for example from trauma (e.g., from cataract surgery), disease or dystrophy, the cornea swells with fluid (edema) and loses its optical clarity. Patients consequently suffer from vision loss and pain, and their only option to treat advanced disease is with corneal transplant surgery (also known as penetrating keratoplasty, PK) or Descemet's stripping endothelial keratoplasty (DSAEK), both technically difficult procedures that are very invasive to the patient and have significant limitations, such as the number of donor corneas available.

Recent studies have proposed the use of human corneal endothelial cells (HCECs) obtained from cadaveric donors to replace the damaged cells. See, e.g., Joyce and Zhu, *Cornea.* 2004 November; 23(8 Suppl):S8-S19; Engelmann, et al., Exper. Eye Res., vol. 78, no. 3, pp. 573-578, 2004. A potential advantage to such an approach could be the expansion of HCECs ex vivo before implantation into patients, thereby overcoming the limited tissue availability. HCECs can be expanded in defined tissue culture media for at least 5 passages, greatly expanding the number of cells derived from a single donor.

One of the main problems with such a technique is that the lack of defined surface markers specific for HCECs makes it difficult to confirm the identity of HCECs after several passages, or to select HCECs away from contaminating cells, or to identify the subset of HCECs that are likely to have the highest clinical efficacy from among the full population of HCECs, as current identification criteria are limited to cell morphology and the expression of functional genes, such as ATP1A1 (see, e.g., Kaye and Tice, *Invest Ophthalmol* 1966; 522-32; Leuenberger and Novikoff, *J Cell Biol.* 1974; 60721-731; McCartney et al., *Curr Eye Res,* 1987; 61479-1486) or the tight junction marker zonula occludens-1(ZO-1) (see, e.g., Petroll et al., *Curr Eye Res.* 1999 January; 18(1):10-9), neither of which are specific to HCECs. It is also difficult to isolate HCECs from contaminant fibroblasts in culture, from neighboring cells in whole corneas, or from residual corneas from DSAEK.

In this regard, the current isolation method for obtaining HCECs from intact corneas comprises a peel-off step, where the endothelium and its basement membrane (Descemet's membrane) are peeled off the stroma and collected. See, e.g., Ko-Hua Chen et al., "Transplantation of Adult Human Corneal Endothelium Ex Vivo: A Morphologic Study," *Cornea* 20(7): 731-737, 2001. The tissue collected thus contains HCECs, but it may also contain corneal keratocytes (specialized fibroblasts residing the stroma). Corneal keratocytes (also referred to herein simply as "keratocytes") are undesirable contaminants in the HCECs culture, as they grow faster than the latter cells and they can take over the culture dish, thus making the final product essentially useless. In addition to residual stromal tissue, keratocytes may also arise from human endothelial cells which transform spontaneously into other types of cells such as keratocytes (see, e.g., G S. L. Peh et al., "Optimization of Human Corneal Endothelial Cells for Culture: The Removal of Corneal Stromal Fibroblast Contamination Using Magnetic Cell Separation," *International Journal of Biomaterials*, Volume 2012 (2012), Article ID 601302, 8 pages.)

SUMMARY OF THE INVENTION

Some aspects of the invention are directed to methods for the identification, enrichment and/or isolation of human corneal endothelial cells (HCECs).

In some embodiments, the method comprises a positive selection process in which a cell population containing human corneal cells is contacted with a positive affinity reagent that selectively binds to HCECs relative to cells other than HCECs. The cells to which the positive affinity reagent is bound are then selected, with the result being that selected cells are enriched with HCECs. In some embodiments, two or more differing positive affinity reagents which bind to HCECs but which do not bind to cells other than HCECs are employed.

As defined herein "cells other than human corneal endothelial cells" (or "cells other than HCECs") include corneal keratocytes as well as HCECs of lower utility (e.g., HCECs that have undergone fibroblastic or mesenchymal transformation, etc.).

In other embodiments, the method comprises a negative selection process in which a cell population containing human corneal cells is contacted with a negative affinity reagent that selectively binds to cells other than HCECs (e.g., corneal keratocytes, etc.) relative to HCECs. The cells to which the negative affinity reagent is bound are then removed, with the result being that the cells that are not removed are enriched with HCECs. In some embodiments, two or more differing negative affinity reagents which bind to cells other than HCECs (e.g., corneal keratocytes, etc.) but which do not bind to HCECs are employed.

In some embodiments, the method comprises both (a) positive selection using one or more affinity reagents agents and (b) negative selection using one or more negative affinity reagents.

Other aspects of the invention are directed to affinity reagents and kits useful for the identification, enrichment and/or isolation of HCECs.

Still other aspects of the invention are direct to isolated and/or enriched cell populations that contain HCECs. In some embodiments, such enriched cell populations may contain affinity reagents for the purification of HCECs.

Further aspects of the invention a set forth in the following paragraphs:

Aspect 1. A method of forming a composition enriched with human corneal endothelial cells comprising: (a) contacting a cell population containing human corneal cells with a first positive affinity reagent that selectively binds to human corneal endothelial cells relative to cells other than human corneal endothelial cells and (b) selecting cells to which the first positive affinity reagent is bound.

Aspect 2. The method of aspect 1, wherein the first positive affinity reagent selectively binds to human corneal endothelial cells relative to corneal keratocytes, human corneal endothelial cells of lower utility, or both.

Aspect 3. The method of aspect 1, wherein the first positive affinity reagent selectively binds to a corneal protein selected from protein products of genes X1 through X26 of Table 2, and may comprise, for example, an antibody or aptamer that binds to a corneal protein selected from protein products of genes X1 through X26 of Table 2, including an antibody or aptamer that binds to one or more proteins selected from SEQ ID NO (1) through SEQ ID NO (58) of Table 2.

Aspect 4. The method of aspect 1, wherein the first positive affinity reagent comprises an antibody or aptamer that binds to a protein product of gene X5 of Table 2, an antibody or aptamer that binds to a protein product of gene X15 of Table 2, or an antibody or aptamer that binds to a protein product of X25 of Table 2.

Aspect 5. The method of aspect 1, wherein the first positive affinity reagent comprises (a) an antibody or aptamer that binds to SEQ ID NO (8), (b) an antibody or aptamer that binds to one or more of SEQ ID NO (27), SEQ ID NO (28), SEQ ID NO (29), SEQ ID NO (30) or SEQ ID NO (31), or (c) an antibody or aptamer that binds to one or more of SEQ ID NO (53), SEQ ID NO (54), SEQ ID NO (55), SEQ ID NO (56) or SEQ ID NO (57).

Aspect 6. The method of any of aspects 1-5, wherein the first positive affinity reagent comprises an antibody or aptamer that is coupled to a solid matrix.

Aspect 7. The method of any of aspects 1-6, wherein the first positive affinity reagent comprises an antibody or aptamer that is coupled to a label.

Aspect 8. The method of aspect 7, wherein the label is selected from a magnetic label, a hapten (e.g., biotin) and a fluorescent label.

Aspect 9. The method of any of aspects 1-8, further comprising (a) contacting said cell population containing human corneal cells with a second positive affinity reagent that selectively binds to human corneal endothelial cells relative to cells other than human corneal endothelial cells and (b) selecting cells to which the second positive affinity reagent is bound, wherein the second positive affinity reagent differs from the first positive affinity reagent.

Aspect 10. The method of aspect 9, wherein the second positive affinity reagent selectively binds to a corneal protein selected from protein products of genes X1 through X26 of Table 2, and may comprise, for example, an antibody or aptamer that binds to a corneal protein selected from protein products of genes X1 through X26 of Table 2, including an antibody or aptamer that binds to one or more proteins selected from SEQ ID NO (1) through SEQ ID NO (58) of Table 2.

Aspect 11. The method of aspect 9, wherein the second positive affinity reagent comprises an antibody or aptamer that binds to a protein product of gene X5 of Table 2, an antibody or aptamer that binds to a protein product of gene X15 of Table 2, or an antibody or aptamer that binds to a protein product of X25 of Table 2.

Aspect 12. The method of aspect 9, wherein the second positive affinity reagent comprises (a) an antibody or aptamer that binds to SEQ ID NO (8), (b) an antibody or aptamer that binds to one or more of SEQ ID NO (27), SEQ ID NO (28), SEQ ID NO (29), SEQ ID NO (30) or SEQ ID NO (31), or (c) an antibody or aptamer that binds to one or more of SEQ ID NO (53), SEQ ID NO (54), SEQ ID NO (55), SEQ ID NO (56) or SEQ ID NO (57).

Aspect 13. The method of any of aspects 9-12, wherein the second positive affinity reagent comprises an antibody or aptamer that is coupled to a solid matrix or a label.

Aspect 14. The method of any of aspects 1-13, further comprising (a) contacting said cell population containing human corneal cells with a first negative affinity reagent that selectively binds to cells other than human corneal endothelial cells relative to human corneal endothelial cells and (b) removing the cells to which the first negative affinity reagent is bound.

Aspect 15. The method of aspect 14, wherein the first negative affinity reagent selectively binds to corneal keratocytes, human corneal endothelial cells of lower utility, or both, relative to human corneal endothelial cells.

Aspect 16. The method of aspect 14, wherein the first negative affinity reagent selectively binds to a corneal protein selected from protein products of genes Y1 through Y23 of Table 2, and may comprise, for example, an antibody or aptamer that binds to a corneal protein selected from protein products of genes Y1 through Y23 of Table 2, including an antibody or aptamer that binds to one or more proteins selected from SEQ ID NO (59) through SEQ ID NO (96) of Table 2, or wherein the first negative affinity reagent selectively binds to a corneal protein selected from protein products of genes Z1 through Z8 of Table 2, and may comprise, for example, an antibody or aptamer that binds to a corneal protein selected from protein products of genes Z1 through Z8 of Table 2, including an antibody or aptamer that binds to one or more proteins selected from SEQ ID NO (97) through SEQ ID NO (109) of Table 2.

Aspect 17. The method of aspect 14, wherein the first negative affinity reagent comprises an antibody or aptamer that binds to a protein product of gene Y6 of Table 2.

Aspect 18. The method of aspect 14, wherein the first negative affinity reagent comprises an antibody or aptamer that binds to one or more of SEQ ID NO (66), SEQ ID NO (67) or SEQ ID NO (68).

Aspect 19. The method of any of aspects 14-18, wherein the first negative affinity reagent comprises an antibody or aptamer that is coupled to a solid matrix or a label.

Aspect 20. A composition enriched with human corneal endothelial cells that is made by the method of any of aspects 1-19.

Aspect 21. A kit comprising (a) a positive affinity reagent that selectively binds to human corneal endothelial cells relative to cells other than human corneal endothelial cells and (b) a negative affinity reagent that selectively binds to cells other than human corneal endothelial cells relative to human corneal endothelial cells.

Aspect 22. The kit of aspect 21, wherein the positive affinity reagent selectively binds to a corneal protein selected from protein products of genes X1 through X26 of Table 2, and may comprise, for example, an antibody or aptamer that binds to a corneal protein selected from protein products of genes X1 through X26 of Table 2, including an antibody or aptamer that binds to one or more proteins selected from SEQ ID NO (1) through SEQ ID NO (58) of Table 2.

Aspect 23. The kit of aspect 21, wherein the first positive affinity reagent comprises an antibody or aptamer that binds to a protein product of gene X5 of Table 2, an antibody or aptamer that binds to a protein product of gene X15 of Table 2, or an antibody or aptamer that binds to a protein product of X25 of Table 2.

Aspect 24. The kit of aspect 21, wherein the first positive affinity reagent comprises (a) an antibody or aptamer that binds to SEQ ID NO (8), (b) an antibody or aptamer that binds to one or more of SEQ ID NO (27), SEQ ID NO (28), SEQ ID NO (29), SEQ ID NO (30) or SEQ ID NO (31), or (c) an antibody or aptamer that binds to one or more of SEQ ID NO (53), SEQ ID NO (54), SEQ ID NO (55), SEQ ID NO (56) or SEQ ID NO (57).

Aspect 25. The kit of any of aspects 21-24, wherein the positive affinity reagent comprises an antibody or aptamer that is coupled to a solid matrix or a label.

Aspect 26. The kit of any of aspects 21-25, wherein the negative affinity reagent selectively binds to a corneal protein selected from protein products of genes Y1 through Y23 of Table 2, and may comprise, for example, an antibody or aptamer that binds to a corneal protein selected from protein products of genes Y1 through Y23 of Table 2, including an antibody or aptamer that binds to one or more proteins selected from SEQ ID NO (59) through SEQ ID NO (96) of Table 2, or wherein the negative affinity reagent selectively binds to a corneal protein selected from protein products of genes Z1 through Z8 of Table 2, and may comprise, for example, an antibody or aptamer that binds to a corneal protein selected from protein products of genes Z1 through Z8 of Table 2, including an antibody or aptamer that binds to one or more proteins selected from SEQ ID NO (97) through SEQ ID NO (109) of Table 2.

Aspect 27. The kit of any of aspects 21-25, wherein the negative affinity reagent comprises an antibody or aptamer that binds to a protein product of gene Y6 of Table 2.

Aspect 28. The kit of any of aspects 21-25, wherein the first negative affinity reagent comprises an antibody or aptamer that binds to one or more of SEQ ID NO (66), SEQ ID NO (67) or SEQ ID NO (68).

Aspect 29. The kit of any of aspects 21-28, wherein the negative affinity reagent comprises an antibody or aptamer that is coupled to a solid matrix or a label.

Aspect 30. An affinity reagent selected from (a) a solid matrix or a label coupled to an antibody or aptamer that binds to a corneal protein selected from protein products of genes X1 through X26 of Table 2, including an antibody or aptamer that binds to one or more proteins selected from SEQ ID NO (1) through SEQ ID NO (58) of Table 2, and (b) a solid matrix or a label coupled to an antibody or aptamer that binds to a corneal protein selected from protein products of genes Y1 through Y23 of Table 2, including an antibody or aptamer that binds to one or more proteins selected from SEQ ID NO (59) through SEQ ID NO (96) of Table 2, and protein products of genes Z1 through Z8 of Table 2, including an antibody or aptamer that binds to one or more proteins selected from SEQ ID NO (97) through SEQ ID NO (109) of Table 2.

Aspect 31. A composition enriched with human corneal endothelial cells comprising: (a) human corneal cells and (b) a first positive affinity reagent that selectively binds to human corneal endothelial cells relative to cells other than human corneal endothelial cells.

Aspect 32. The composition of aspect 31, comprising human corneal endothelial cells to which the first positive affinity reagent is bound.

Aspect 33. The composition of any of aspects 31-32, wherein the first positive affinity reagent selectively binds to human corneal endothelial cells relative to corneal keratocytes, human corneal endothelial cells of lower utility, or both.

Aspect 34. The composition of any of aspects 31-33, wherein the first positive affinity reagent selectively binds to a corneal protein selected from protein products of genes X1 through X26 of Table 2, and may comprise, for example, an antibody or aptamer that binds to a corneal protein selected from protein products of genes X1 through X26 of Table 2, including an antibody or aptamer that binds to one or more proteins selected from SEQ ID NO (1) through SEQ ID NO (58) of Table 2.

Aspect 35. The composition of any of aspects 31-33, wherein the first positive affinity reagent comprises an antibody or aptamer that binds to a protein product of gene X5 of Table 2, an antibody or aptamer that binds to a protein product of gene X15 of Table 2, or an antibody or aptamer that binds to a protein product of X25 of Table 2.

Aspect 36. The composition of any of aspects 31-33, wherein the first positive affinity reagent comprises (a) an antibody or aptamer that binds to SEQ ID NO (8), (b) an antibody or aptamer that binds to one or more of SEQ ID NO (27), SEQ ID NO (28), SEQ ID NO (29), SEQ ID NO (30) or SEQ ID NO (31), or (c) an antibody or aptamer that binds to one or more of SEQ ID NO (53), SEQ ID NO (54), SEQ ID NO (55), SEQ ID NO (56) or SEQ ID NO (57).

Aspect 37. The composition of any of aspects 31-36, wherein the first positive affinity reagent comprises an antibody or aptamer that is coupled to a label.

Aspect 38. The composition of aspect 37, wherein the label is selected from a magnetic label, a hapten (e.g., biotin) and a fluorescent label.

Aspect 39. The composition of any of aspects 31-38, further comprising a second positive affinity reagent that selectively binds to human corneal endothelial cells relative to cells other than human corneal endothelial cells, wherein the second positive affinity reagent differs from the first positive affinity reagent.

Aspect 40. The composition of aspect 39, comprising human corneal endothelial cells to which the second positive affinity reagent is bound.

Aspect 41. The composition of any of aspects 39-40, wherein the second positive affinity reagent selectively binds to a corneal protein selected from protein products of genes X1 through X26 of Table 2, and may comprise, for example, an antibody or aptamer that binds to a corneal protein selected from protein products of genes X1 through X26 of Table 2, including an antibody or aptamer that binds to one or more proteins selected from SEQ ID NO (1) through SEQ ID NO (58) of Table 2.

Aspect 42. The composition of any of aspects 39-40, wherein the second positive affinity reagent comprises an antibody or aptamer that binds to a protein product of gene X5 of Table 2, an antibody or aptamer that binds to a protein product of gene X15 of Table 2, or an antibody or aptamer that binds to a protein product of X25 of Table 2.

Aspect 43. The composition of any of aspects 39-40, wherein the second positive affinity reagent comprises (a) an antibody or aptamer that binds to SEQ ID NO (8), (b) an antibody or aptamer that binds to one or more of SEQ ID NO (27), SEQ ID NO (28), SEQ ID NO (29), SEQ ID NO (30) or SEQ ID NO (31), or (c) an antibody or aptamer that binds to one or more of SEQ ID NO (53), SEQ ID NO (54), SEQ ID NO (55), SEQ ID NO (56) or SEQ ID NO (57).

Aspect 44. The composition of any of aspects 39-43, wherein the second positive affinity reagent comprises a label.

Aspect 45. The composition of any of aspects 31-44, comprising a measurable amount of one or more negative affinity reagents that selectively binds to cells other than human corneal endothelial cells relative to human corneal endothelial cells.

Aspect 46. The composition of aspect 45, wherein the one or more negative affinity reagents selectively binds to corneal keratocytes, human corneal endothelial cells of lower utility, or both, relative to human corneal endothelial cells.

Aspect 47. The composition of any of aspects 45-46, wherein the one or more negative affinity reagents selectively bind to a corneal protein selected from protein products of genes Y1 through Y23 of Table 2, and may comprise, for example, one or more antibodies that bind to one or more corneal proteins selected from protein products of genes Y1 through Y23 of Table 2, including one or more antibodies or aptamers that bind to one or more proteins selected from SEQ ID NO (59) through SEQ ID NO (96) of Table 2, or the one or more negative affinity reagents selectively bind to a corneal protein selected from protein products of genes Z1 through Z8 of Table 2, and may comprise, for example, one or more antibodies or aptamers that bind to one or more corneal proteins selected from protein products of genes Z1 through Z8 of Table 2, including one or more antibodies or aptamers that bind to one or more proteins selected from SEQ ID NO (97) through SEQ ID NO (109) of Table 2.

Aspect 48. The composition of any of aspects 45-46, wherein the one or more negative affinity reagents comprise an antibody or aptamer that binds to a protein product of gene Y6 of Table 2.

Aspect 49. The composition of any of aspects 45-46, wherein the one or more negative affinity reagents comprise an antibody or aptamer that binds to one or more of SEQ ID NO (66), SEQ ID NO (67) or SEQ ID NO (68).

Aspect 50. The composition of any of aspects 45-49, wherein the one or more negative affinity reagents comprise an antibody or aptamer that is coupled to a label.

These and various other aspects and embodiments and as well as various advantages of the present invention will become immediately apparent to those of ordinary skill in the art upon review of the Detailed Description and appended claims to follow.

BRIEF DESCRIPTION OF THE DRAWINGS

FIGS. 1A-1C are bright field micrographs of HCECs and keratocytes in culture, with FIG. 1A illustrating a HCEC culture having preserved a typical cobblestone morphology (P2-HCEC-Good), FIG. 1B illustrating a HCEC culture having become fibroblastic (P3-HCEC-Fibroblastic), and FIG. 1C illustrating a human corneal keratocyte culture (P2-HCEC-Keratocytes).

FIG. 2 illustrates in bar graph form expression of four surface markers in different corneal cell populations analyzed by flow cytometry.

FIGS. 6A-6C illustrates dual-color fluorescence histograms for various pairs of surface markers, specifically, CD56:CD248 (FIG. 6A), CD56:CD109 (FIG. 6B) and CD56:CAR (FIG. 6C) in three different HCEC populations, specifically, canonical HCECs, mixed HCECs and fibroblastic HCECs.

FIG. 7 illustrates trans-endothelial electrical resistance (TEER) as a function of time for cell cultures of three different HCEC populations.

DETAILED DESCRIPTION

Figure 3A:
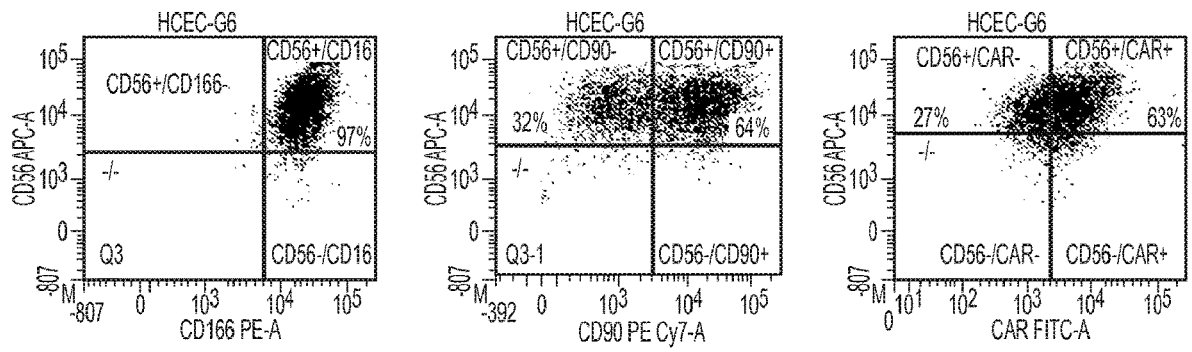
FIGS. 3A-3C are dual-color fluorescence histograms of HCECs and keratocytes. These dot plots show the differential expression of two surface markers (CD56:CD166, CD56:CD90 and CD56:CAR) in each cell population, with FIG. 3A corresponding to the P2-HCEC-Good culture shown in FIG. 1A, FIG. 3B corresponding to the P3-HCEC-Fibroblastic culture shown in FIG. 1B, and FIG. 3C corresponding to the P2-HCEC-Keratocytes culture shown in FIG. 1C.

A more complete understanding of the present invention is available by reference to the following detailed description of numerous aspects and embodiments of the invention. The detailed description of the invention which follows is intended to illustrate but not limit the invention.

As noted above, in some aspects, the present disclosure pertains to positive selection processes in which cell populations containing human corneal cells are contacted with one or more positive affinity reagents that selectively bind to HCECs relative to cells other than HCECs (e.g., corneal keratocytes, etc.), including positive affinity reagents that selectively bind to HCECs that are likely to have a higher clinical efficacy relative to the general HCEC population In other aspects, the present disclosure pertains to negative selection processes in which cell populations containing human corneal cells are contacted with one or more negative affinity reagents that bind selectively bind to cells other than HCECs (e.g., corneal keratocytes, etc.) relative to HCECs.

These negative and positive selection methods may be used independently or in combination with one another, for example, to identifying HCECs, to isolate HCECs and/or to enrich cell populations with HCECs, among other uses.

Cell populations suitable for HCEC enrichment or isolation include those obtained from intact or residual human corneas, which may come, for instance, from embryonic, fetal, pediatric or adult tissue. For example, intact corneas may be subjected to a peel-off step in which the endothelium and its basement membrane (Descemet's membrane) are peeled off the stroma and collected. See Ko-Hua Chen et al., "Transplantation of Adult Human Corneal Endothelium Ex Vivo: A Morphologic Study," *Cornea* 20(7): 731-737, 2001. In other embodiments, cell populations may be obtained from residual corneas (e.g., eye tissue remaining after a corneal button has been used for DSAEK).

Tissue from intact and residual corneas may be separated into individual cells by processes such as enzymatic and/or mechanical dissociation. At this step, cells are incubated for a period of time at room temperature or at 37° C. with a single enzyme or a combination of enzymes including some of the following: collagenase, papain, dispase, elastase, trypsin/EDTA, and/or DNAse. Later the tissues are mechanically dissociated using a conventional pipette or a glass pipette to obtain individual cells or cell clumps than can be then expanded in culture. See, e.g., Li W. et al., *Invest Ophthalmol Vis Sci* 2007; 48: 614; Ishino Y. et al., *Invest Ophthalmol Vis Sci* 2004; 45: 800; Chen K. H. et al., *Cornea* 2001; 20: 731.

The medium in which the cells may be suspended will be any medium which maintains the viability of HCECs. Various media are commercially available and may be used including Minimal Essential Medium (MEM), Dulbecco's Modified Eagle Medium (DMEM), Opti-MEMO, Media 199 or M199, Dulbecco's Modified Eagle Medium with Nutrient Mixture F-12 (DMEM/F-12), F99 Ham's F12, SHEM Ham's F12, EGM-2 endothelial growth medium frequently supplemented with serum of human or animal origin, BSA, HSA, growth factors, antioxidants, antibiotics, antimicotic agents, hormones, amino acids, and peptides. Specific examples of media are shown in Table 1 to follow.

TABLE 1

| Base Medium | Serum | Growth Factors & Supplements |
| --- | --- | --- |
| [M1] DMEM | 10% | 2 ng/ml bFGF<br>50 U/ml penicillin<br>50 µg/ml streptomycin |
| [M2] Opti-MEM-I | 8% | 20 ng/ml NGF<br>5 ng/ml EGF<br>20 µg/ml ascorbic acid<br>200 mg/L calcium chloride<br>100 µg/ml pituitary extract<br>50 µg/ml gentamicin<br>1x antibiotic/antimycotic<br>0.08% chondroitin sulphate |
| [M3] SHEM Ham's F12 & DMEM (1:1 ratio) | 5% | 0.5% DMSO<br>2 ng/ml EGF<br>5 µg/ml insulin<br>5 µg/ml transferrin<br>5 ng/ml selenium<br>0.5 µg/ml hydrocortisone<br>1 nM cholera toxin<br>50 µg/ml gentamicin<br>1.25 µg/ml amphotericin B |
| [M4] F99 Ham's F 12 & M100 (1:1 ratio) | 5% | 20 µg/ml ascorbic acid<br>20 µg/ml bovine insulin<br>2.5 µg/mol transferrin<br>0.6 ng/ml sodium selentite<br>10 ng/ml bFGF |

Cell cultures from intact and residual corneas contain unwanted contaminant cells which arise from residual non-endothelial tissue (e.g., stroma, epithelium, etc.) that may be present in the sample. In a culture of HCECs, HCECs that are of low cell transplant utility compared to other HCECs of high cell transplant utility may also be considered, in some fashion, "contaminants".

Cell populations suitable for HCEC enrichment or isolation also include HCEC cultures in which contaminant cells have out-multiplied HCECs or in which HCECs have transformed spontaneously into other types of cells (e.g., keratocytes, etc.). As previously noted, contaminant cells such as keratocytes are particularly undesirable where it is desired to expand an HCEC culture ex vivo, because such cells grow faster than HCECs and can thus take over a cell culture.

Consequently, various aspects of the invention pertain to methods, reagents and kits for separation of HCECs from other cells, particularly, keratocytes and/or HCECs of lower utility. The HCECs are separated from mixtures of cells by techniques that select cells having particular characteristics.

Human corneal endothelial cells may identified or selected (a) through positive cell markers, which are cell markers that are found on the surfaces of HCECs but which are not found on the surfaces of contaminant cells which may be intermixed with HCECs (e.g., positive selection), (b) through negative cell markers, which are cell markers that are found on surfaces of contaminant cells that are intermixed with HCECs and but which are not found on the surfaces of HCECs (e.g., negative selection), and through a combination of positive and negative cell markers.

For example, in the case where whole human corneas are used as a source of endothelial cells, positive cell markers may be selected from corneal proteins which are found in the endothelium (which is formed from HCECs) but which are not found in other corneal tissue (i.e., the stroma and/or the epithelium). Conversely, negative cell markers may be selected from corneal proteins which are found in corneal tissue other than endothelium tissue (i.e., the stroma and/or the epithelium) but which are not present in corneal endothelium.

As another example, in the case where the source of endothelial cells is an endothelium and basement membrane that have been separated from the stroma and epithelium of an intact cornea, positive cell markers may be selected from corneal cell proteins which are found in the endothelium but which are not found in the stroma, while negative cell markers may be selected from corneal cell proteins which are found in the stroma but which are not found in corneal endothelium.

Corneal proteins which may be useful as cell markers in conjunction with the present invention include the suitable proteins selected from those presented in the Table 2 set forth in Appendix A.

Positive cell markers include suitable corneal proteins selected from protein products of genes X1-X26 in Table 2 (e.g., SEQ ID NO (1) through SEQ ID NO (58)) which are present in the corneal endothelium but are not present in the stroma or the epithelium.

Negative cell markers include (a) suitable corneal proteins selected from protein products of genes Y1-Y23 in Table 2 (e.g., SEQ ID NO (59) through SEQ ID NO (96)), which are present in the stroma and in epithelium but are not present in the endothelium and (b) suitable corneal proteins selected from protein products of genes Z1-Z8 in Table 2 (e.g., SEQ ID NO (97) through SEQ ID NO (109)), which are present in the stroma but are not present in the corneal endothelium (or epithelium).

As previously noted, in some aspects, the present disclosure pertains to (a) positive selection processes in which cell populations containing human corneal cells are contacted with one, two, three, four or more positive affinity reagents that selectively bind to HCECs relative to cells other than HCECs (e.g., corneal keratocytes, etc.), (b) negative selection processes in which cell populations containing human corneal cells are contacted with one, two, three, four or more negative affinity reagents that selectively bind to cells other than HCECs (e.g., corneal keratocytes, etc.) relative to HCECs, and (c) combinations of (a) and (b).

For this purpose, affinity reagents are employed which preferentially bind to various corneal proteins. Positive affinity reagents are those that preferentially bind to positive cell markers associated with HCECs while negative affinity reagents are those that preferably bind to negative cell markers associated with contaminant cells other than HCECs.

Various positive cell markers are described above and include corneal proteins which are found in the endothelium (which is formed from HCECs) but which are not found in other corneal tissue (i.e., the stroma and/or the epithelium). Various negative cell markers are also described above and include corneal proteins which are found in corneal tissue other than endothelium (i.e., the stroma and/or the epithelium) but which are not found in corneal endothelium.

Those skilled in the art will recognize that suitable negative and positive affinity reagents can be employed in any order and/or in any combination.

Affinity reagents suitable for use in the present disclosure may comprise any species which selectively binds to a given surface marker, including positive affinity reagents which selectively bind to positive cell markers and negative affinity reagents which selectively bind to negative cell markers.

Especially useful affinity reagents for the practice of the invention are antibodies (also referred to herein as "affinity antibodies"), nucleic acid aptamers and other engineered forms of protein scaffolds. Antibodies include whole antibodies and antibody fragments, e.g. Fab, F(ab')2, light or heavy chain fragments, etc.

Affinity antibodies selected for use will have a low level of non-specific interactions.

Affinity antibodies may be polyclonal or monoclonal and, where not commercially available, may be readily produced by techniques known to those skilled in the art.

For instance, affinity antibodies to a given corneal protein may be obtained by immunizing a xenogeneic immunocompetent mammalian host (including murine, rodentia, lagomorpha, ovine, porcine, bovine, etc.) with the corneal protein of interest. Immunizations are performed in accordance with conventional techniques, where the corneal proteins may be injected subcutaneously, intramuscularly, intraperitoneally, intravascularly, etc., over a course of one or more injections. After completion of the immunization schedule, the antiserum may be harvested in accordance with conventional methods to provide polygonal antisera specific for the corneal protein of interest. Lymphocytes may also be harvested from the appropriate lymphoid tissue, e.g. spleen, draining lymph node, etc., and fused with an appropriate fusion partner, for example, a myeloma line, producing a hybridoma secreting a specific monoclonal antibody. Screening clones of hybridomas for the antigenic specificity of interest is performed in accordance with conventional methods.

In numerous embodiments, affinity antibodies are coupled to a suitable substrate, for example, a label or a solid matrix. Labels include magnetic labels such as magnetic beads or micro or nanoparticles including superparamagnetic nanoparticles, which allow for ease of separation. Labels also include biotin, which binds with high affinity to avidin or streptavidin. Labels further include fluorochromes, which can be used with flow cytometry, e.g., fluorescence activated cell sorting (FACS), or the like, to allow for ease of separation of a particular cell type. Fluorescence activated cell sorters have varying degrees of sophistication, such as multiple color channels, low angle and obtuse light scattering detecting channels, impedance channels, etc. Fluorochromes include phycobiliproteins, e.g., phycoerythrin and allophycocyanins, fluorescein and Texas red, cy7 and cy5, among others. Multiple antibodies each with an affinity to a particular corneal protein may each be labeled with a different fluorochrome, to permit independent sorting (multicolor analyses) for each associated cell protein.

Cell selection may also be achieved by "panning" with an affinity antibody attached to a solid matrix, e.g. a plate, an immobilized bead, and so forth. For example, an affinity antibody that has specificity for a particular corneal protein may be bound to a solid matrix and corneal cells displaying that particular corneal protein can be captured by the immobilized antibody while the other cells remain in suspension and can be removed.

Any sorting technique may be employed which is not unduly detrimental to the viability of the selected cells. Combinations of the above techniques may be used.

The precise method for coupling an antibody to a given substrate (e.g., a label, solid matrix, etc.) is not critical to the practice of the present disclosure, and a number of alternatives are known in the art. For example, affinity antibodies may directly or indirectly be coupled to a substrate. Direct coupling to a substrate can be achieved by use of various chemical linking groups, as known in the art. For example, an antibody can be coupled to a substrate through side chain amino or sulfhydryl groups and heterofunctional cross-linking reagents. Many heterofunctional compounds are available for linking to various entities. Specific examples include 3-(2-pyridyldithio)propionic acid N-hydroxysuccinimide ester (SPDP) or 4-(N-maleimidomethyl)-cyclohexane-1-carboxylic acid N-hydroxysuccinimide ester (SMCC), which can react with a reactive sulfhydryl group on the antibody and a reactive amino group on the substrate.

Alternatively, affinity antibodies can be indirectly coupled to a substrate via a hapten or a secondary antibody. For instance, the antibody may be directly conjugated to a hapten, and hapten-specific binding species may be conjugated to the substrate. Suitable haptens include digoxin, digoxigenin, FITC, dinitrophenyl, nitrophenyl, avidin, streptavidin, biotin, etc. For example, an antibody may be coupled to one member of a high affinity binding system (e.g., biotin) and another member of the high affinity binding system (e.g., avidin) attached to a substrate. Methods for conjugation of a hapten to a protein are known in the art, and kits for such conjugations are commercially available. The secondary antibody may be directly or indirectly bound to the substrate.

During cell separation, coupled antibodies may be combined with a suspension of cells and incubated for a period of time sufficient for the antibodies to bind to proteins on the cells. The amount of antibody necessary to bind a particular cell subset may be empirically determined by performing a test separation and analysis. The cells and antibodies are incubated for a period of time sufficient for binding to occur.

The medium in which the cells are separated will be any medium which maintains the viability of the cells. Various media are commercially available and include those listed above.

Coupled affinity antibodies include coupled positive affinity antibodies specific for the corneal proteins which are present on human corneal endothelial cells and which are not present on contaminant cells such as stromal and/or epithelial cells (for positive selection) and coupled negative affinity antibodies specific for corneal proteins which are present on contaminant cells such as stromal and/or epithelial cells and which are not present on human corneal endothelial cells (negative selection).

Once the antibody is bound to the cell, the bound cells are separated in accordance with the specific antibody preparation. For example, FACS separation may be used with fluorochrome labeled antibodies, immunomagnetic selection may be used with magnetic-labeled antibodies, "panning" may be employed with immobilized antibodies, and so forth.

Cells may be separated from affinity antibodies using known techniques, as desired. As a specific example, where an antibody in an immunopanning process is a positive selection antibody, the matrix with attached endothelial cells may be washed to remove unbound cells and the endothelial cells released using a suitable technique (e.g., trypsin digest).

While various specific embodiments employing antibodies as affinity reagents are specifically described herein, it is to be understood that other affinity reagents for binding positive or negative cell markers can be used in the same fashion, including nucleic acid aptamers and other engineered forms of protein scaffolds. Aptamers are synthetic oligonucleotides selected from pools of random-sequence oligonucleotides which bind to a wide range of biomolecular targets with high affinity and specificity. See, e.g., J. Wang and G. Li, "Aptamers against cell surface receptors: selection, modification and application," Curr Med Chem. 2011; 18(27):4107-16.

The separated cells may be collected in any appropriate medium that maintains the viability of the cells.

Cell populations enriched with HCECs may thus be achieved in this manner. The HCEC population may constitute 50% or more of the cells in the cell composition, preferably at 75% or more of the cells in the cell composition, more preferably at 90% or more of the cells in the cell composition, and may be as many as 95% or more (e.g. substantially pure) of the cells in the cell population. Conversely, the cell populations may contain up to 50% of cells other than HCECs (e.g., corneal keratocytes, etc.), for instance 50% or less of such cells, preferably 25% or less of such cells, more preferably 10% or less of such cells, and may be as few as 5% or less of such cells.

The enriched cell population may be used immediately or stored. For example, at room temperature, at 4° C., at 37° C. or the cells may be frozen at liquid nitrogen temperatures and stored for long periods of time.

In certain embodiments, the enriched cells may be further expanded in vitro by adding culture media as described widely in the literature. See, e.g., Li W et al., *Invest Ophthalmol Vis Sci* 2007; 48: 614; Ishino Y et al., *Invest Ophthalmol Vis Sci* 2004; 45: 800; Chen K H et al., *Cornea* 2001; 20: 731.

The enriched HCEC compositions thus obtained have a variety of uses in clinical therapy, research, development, and commercial purposes.

For example, for therapeutic purposes, human corneal endothelial cells may be ocularly administered to an eye of a patient in order to treat corneal endothelial cell loss or dysfunction.

Other aspects of the invention pertain to kits for conducting cell separations as described herein. Such kits may include any combination of the following, among other elements: (a) one, two, three or more positive affinity reagents, each of which may be, for example, in the form of a positive affinity antibody attached to a suitable substrate such as a solid matrix (e.g. a plate, immobilized bead, etc.) or label (e.g., magnetic label, fluorescent label, etc.), (b) one, two, three or more unlabeled positive affinity antibodies, which the end user could label using standard methods, choosing their preferred labels (e.g., fluorophores, haptens, etc.), (c) one, two, three or more negative affinity reagents, each of which may be, for example, in the form of a negative affinity antibody attached to a suitable substrate such as a solid matrix (e.g. a plate, immobilized bead, etc.) or label (e.g., magnetic label, fluorescent label, etc.), (d) or one, two, three or more unlabeled negative affinity antibodies, which the end user could label using standard methods, choosing their preferred labels (e.g., fluorophores, haptens, etc.); (e) a combination of (a) and (c); (f) a combination of (b) and (d); (g) packaging; (h) printed materials with one or more of the following: (i) storage information and (ii) instructions regarding how to use the materials contained in the kit (e.g., positive affinity reagents, negative affinity reagents, a combination of antibodies for sequential use, etc.).

Example 1

HCECs were isolated from cadaveric donor corneas (Tampa Lions Eye Bank) and cultured and expanded following the method described by Joyce and Zhu in *Cornea*. 2004 November; 23(8 Suppl):S8-S19. Briefly, the endothelium and Descemet's membrane were peeled off of the stroma and after overnight stabilization at 37° C. in Opti-MEM® media (Gibco, Life Technologies Corp, Carlsbad, Calif.), supplemented with 8% fetal bovine serum (FBS), they were incubated for 1 hr at 37° C. with ethylenediaminetetraacetic acid (EDTA) to loosen up the cell-cell interactions. Cells were then mechanically dissociated to obtain a single-cell suspension, they were seeded onto FNC-coated culture wells and labeled as "P0" (passage zero). After reaching confluency, they were trypsinized and further expanded into more wells to increase their number. After one or two rounds of expansion, cells were collected and incubated with different antibodies as indicated below. Keratocytes were also obtained from cadaveric donor corneas using the method described by Stramer et al. in "Monoclonal antibody (3G5)-defined ganglioside: cell surface marker of corneal keratocytes," *Invest. Ophthalmol. Vis. Sci.* 2004 vol. 45 no. 3 807-812. While one of the HCEC cultures preserved its typical cobblestone morphology at passage 2 (FIG. 1A), a second culture underwent endothelial-to-mesenchymal transition during passage 3 (P3) and the cells became fibroblastic (FIG. 1B). Such cells are generally referred to herein as human corneal endothelial cells of lower utility (e.g., HCECs that have undergone fibroblastic or mesenchymal transformation, etc.) The keratocyte culture exhibits the typical fibroblastic, elongated cell morphology (FIG. 1C).

HCECs from each culture and keratocytes were collected and incubated with one or more of the following labelled antibodies: (a) APC-CD56 which is a mouse monoclonal antibody against a protein product of gene X15 from Table 2 (referred herein to as CD56 surface protein) coupled to allophycocyanin (BD Biosciences, #555518), (b) PE-CD166, which is a mouse monoclonal antibody against a protein product of gene X1 from Table 2 (referred here to as CD166 surface protein) coupled to phycoerythin (BD Biosciences #559263), (c) FITC-CAR, which is a mouse monoclonal antibody against a protein product of gene X25 from Table 2 (referred to as CAR surface protein) coupled to fluorescein-5-Isothiocyanate (Santa Cruz Biotechnology, Santa Cruz, Calif., USA #sc-56892) and (d) PECy7-CD90, which is a mouse monoclonal antibody against a protein product of gene Z8 from Table 2 (referred to as CD90 surface protein) coupled to a tandem conjugate of PE (energy donor) which has an excitation wavelength of 565 nm and Cy7 (energy acceptor) which has an emission wavelength of 778 nm) (BD Biosciences #561558).

Expression of surface markers was analyzed using a BD LSR™II flow cytometry system (BD Biosciences, San Jose, Calif.). The data shown in FIG. 2 are representative from one experiment. Similar results were obtained upon repeated experimentation. Quantification of the % positive cells for each marker shows that in fibroblastic cultures there is a decreased expression of CD56 and CAR, indicating that antibodies to these proteins may be used in conjunction with positive affinity reagents for "good" HCECs. A significant difference in the expression of CD166 or CD90 was not detected using this particular antibody.

Figure 3B:
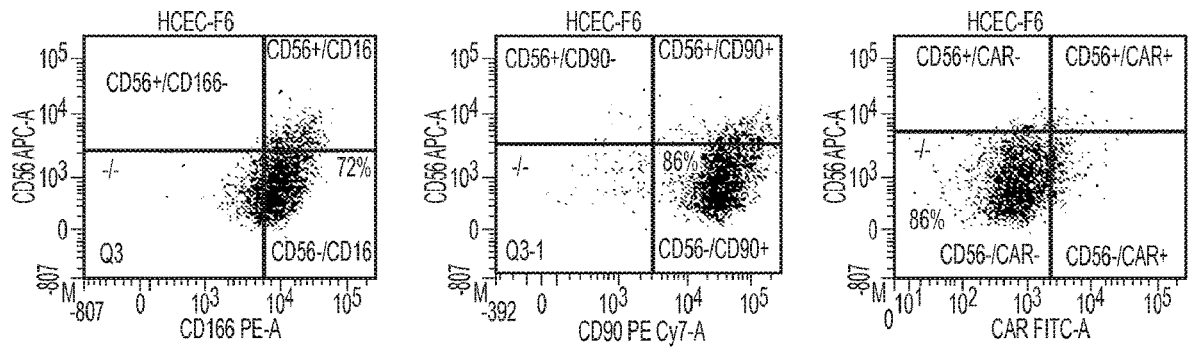
Figure 3C:
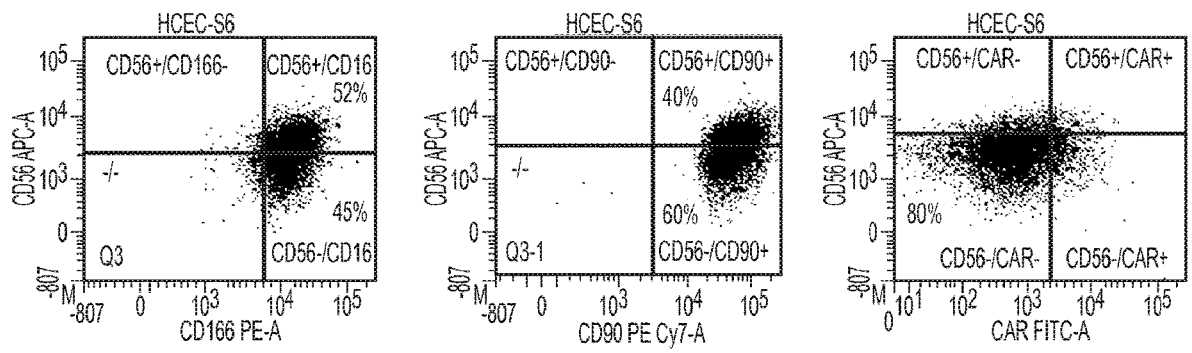
Figure 4A:
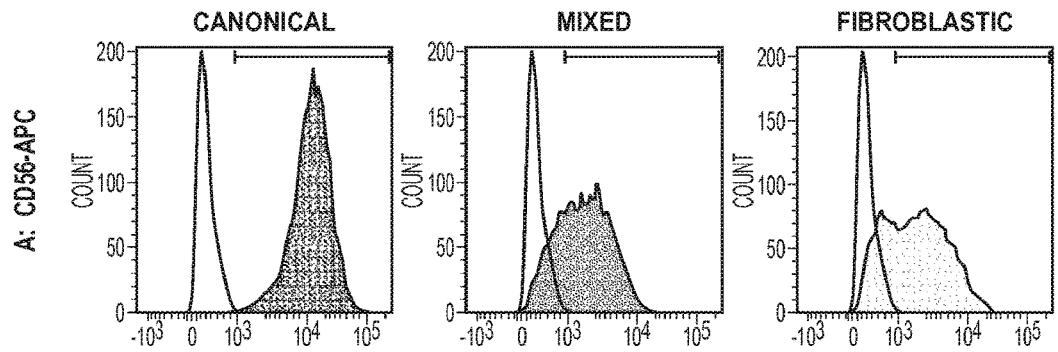
FIGS. 4A-4D present Fluorescence profiles illustrating expression of four surface markers, specifically, CD56 (FIG. 4A), CAR (FIG. 4B), CD109 (FIG. 4C) and CD248 (FIG. 4D) in three different HCEC populations, specifically, canonical (good) HCECs, mixed (canonical and fibroblastic) HCECs, and fibroblastic (HCECs), analyzed by flow cytometry.
Figure 4B:
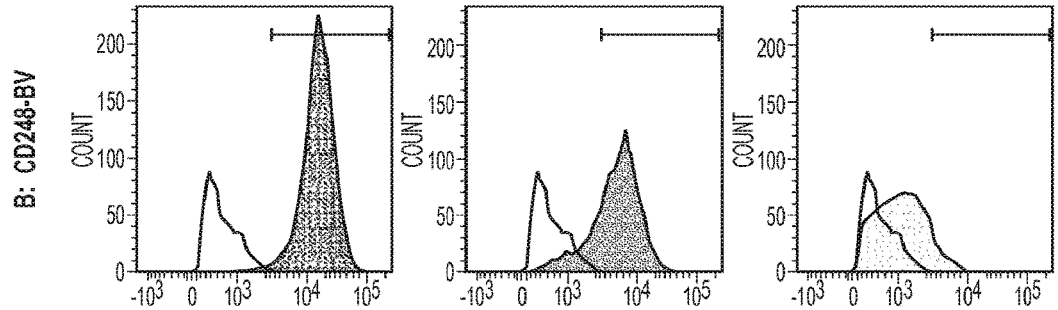
Figure 4C:
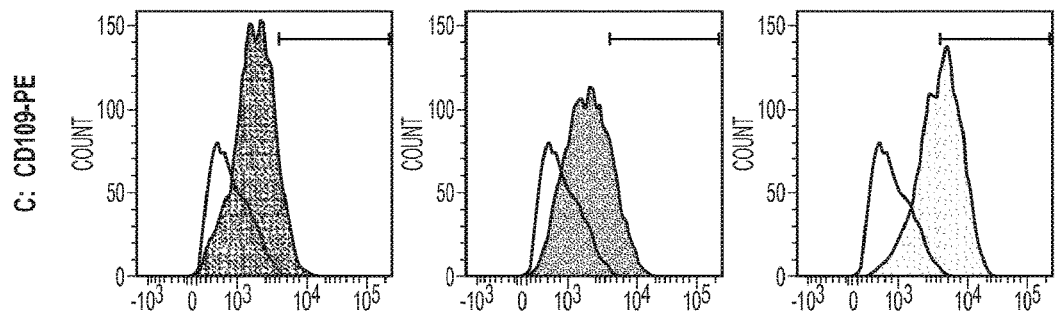
Figure 4D:
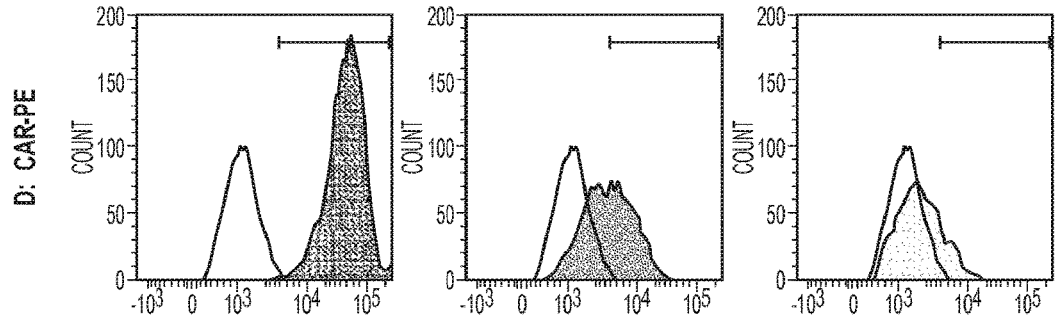

FIGS. 3A-3C are dual-color fluorescence dot plots of the HCECs and keratocytes. These dot plots show the differential expression of two surface markers in each cell population as labeled. The percent of cells positive for an individual marker is shown in FIG. 2.

Example 2

HCECs were isolated from cadaveric donor corneas as described in Example 1. Also as discussed in Example 1, HCEC cultures were obtained (a) which evidenced a typical cobblestone morphology (referred to in this Example 2 as a "canonical" cell culture), (b) where all the cells had undergone an endothelial-to-mesenchymal transition (referred to in this Example as a "fibroblastic" cell culture) and (c) where some HCECs had undergone endothelial-to-mesenchymal transition (referred to in this Example as a "mixed" cell culture).

HCEC surface markers were identified by microarray data, and several with high expression in the endothelium (cultured and freshly dissected) but low expression in stroma were selected to be tested by flow cytometry analysis. In addition to APC-CD56, PE-CD166, FITC-CAR and PECy7-CD90 described in Example 1, also tested were (e) CD109-PE, (i.e., mouse anti-CD109), which is a monoclonal antibody against a protein product of gene Y6 from Table 2 (referred to as CD109 antigen) conjugated to phycoerythrin (PE), BD Biosciences Cat #556040 and (f) CD 248-BV, (i.e., mouse anti-Endosialin), which is an unconjugated monoclonal antibody against a protein product of gene X5 from Table 2 (referred to as CD248 antigen or Endosialin), (Millipore, Temecula, Calif., USA, Cat #MAB2626), incubated with Goat polyclonal anti-Mouse IgG secondary antibody conjugated to Brilliant Violent 421 (Biolegend, Inc., San Diego, Calif., USA, Cat #405317).

Figure 5:
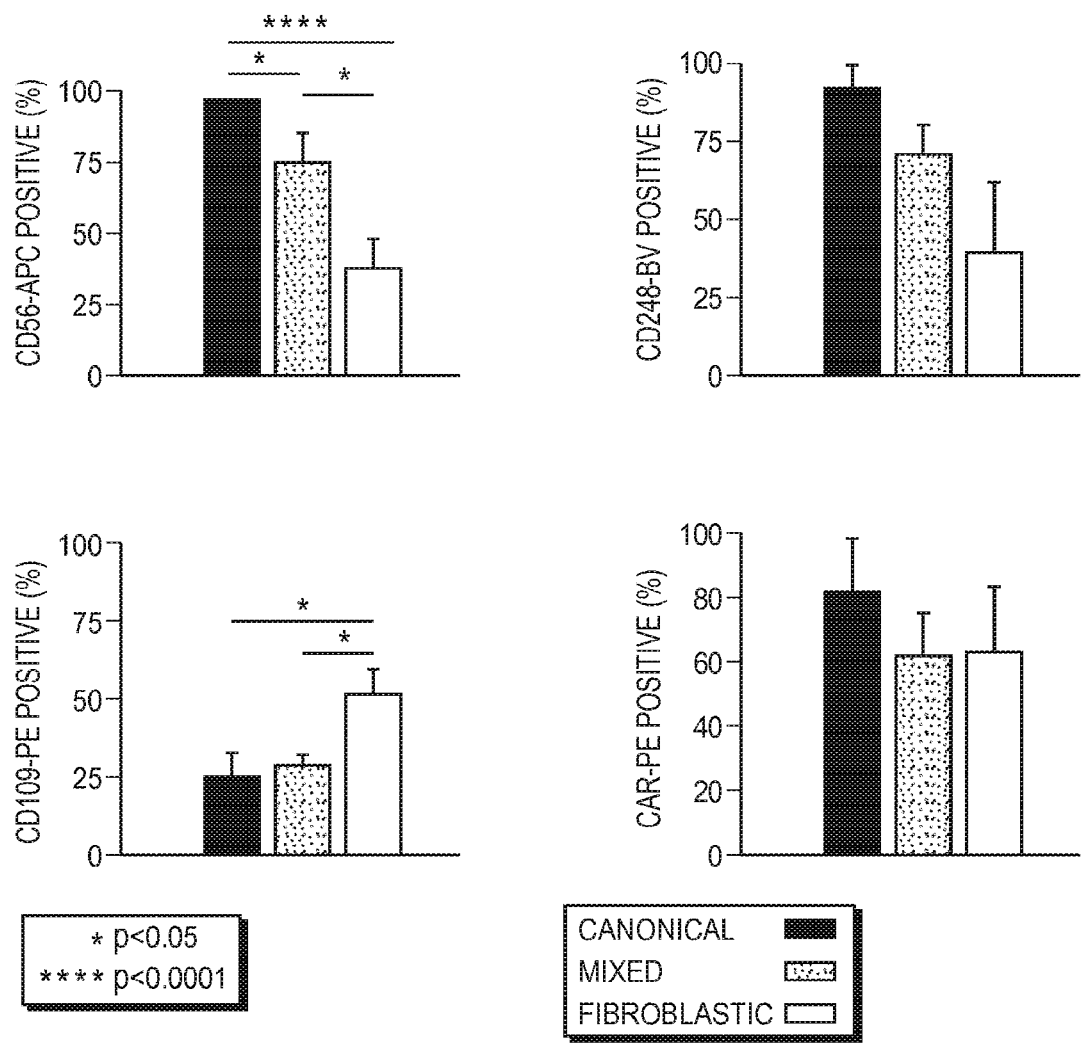
FIG. 5 illustrates in bar graph form expression of four surface markers in three different HCEC populations analyzed by flow cytometry.

To address whether the expression of those markers in HCECs were affected by the fibroblastic conversion described above, HCEC cultures demonstrating two different morphologies (canonical and fibroblastic) and a corneal keratocyte culture as a control were immunostained for the surface proteins CD90, CAR, CD56 and CD166 (See Example 1, FIG. 2). CD56, CAR, CD109 and CD248 expression was also compared between canonical (good), mixed, and fibroblastic HCECs (see FIGS. 4A-4D and 5). Analysis of the percentage of cells expressing any of the individual markers in canonical and fibroblastic cultures demonstrated that CD56, CAR and CD248 expression was reduced in the fibroblastic culture (see FIG. 5), while CD109 was elevated (see FIG. 5); CD90 and CD166 expression did not significantly change between good/canonical and fibroblastic cultures (see Example 1, FIG. 2). A comparable trend was observed in the keratocyte culture used as control for CD90, CAR, CD56 and CD166 expression (see Example 1, FIG. 2).

Dot plot dual histograms of canonical, mixed and fibroblastic cultures shown in FIGS. 6A-6C demonstrated that canonical HCECs are predominantly CD56, CD248 and CAR positive, and CD109 negative; CD56 and CD248 expression is lost and CD109 expression increases as the culture becomes fibroblastic.

Finally, trans-endothelial electrical resistance (TEER) of cell cultures was measured. HCECs (a) from "good" or "canonical" cultures that expressed high levels of CD56, (b) from mixed cultures and (c) from fibroblastic cultures were plated onto inserts with 0.4 mm pores in 24-well culture plates (Transwell, Corning Costar, Acton, Mass.) at a density of 20,000 cells/insert and incubated in growth media as described in Example 1. TEER was measured using an EVOM volt-ohm meter with STX2 Electrode (World Precision Instrument, Inc., Sarasota, Fla.) for up to 65 days after initial plating. TEER measures the apical and basal plasma membrane resistance and the paracellular resistance and is used as an index of monolayer confluence integrity of tight junctions. To calculate final resistance (Ω·cm2), the resistance of blank filters were subtracted from those of filters with cells. Four wells per condition were averaged. HCECs exhibiting a canonical morphology and being CD56-positive demonstrated a superior barrier formation ability measured by TEER (FIG. 7).

Thus, we have identified a panel of surface makers that can be used to characterize a canonical and functionally superior HCEC culture, and may be used as quality control criteria or to potentially separate the best HCEC subpopulations for expansion.

Although various embodiments are specifically illustrated and described herein, it will be appreciated that modifications and variations of the present invention are covered by the above teachings and are within the purview of any appended claims without departing from the spirit and intended scope of the invention.

APPENDIX A

TABLE 2

```
Gene ID:         X1
Gene symbol:     ALCAM
Gene description: activated leukocyte cell adhesion molecule
Unigene:         Hs.591293
Genbank:         DQ486139
Entrez Gene:     214
Refseq:          NM_001627
Protein sequence (SEQ ID NO (1)):
         1       meskgasscr  llfcllisat  vfrpglgwyt  vnsaygdtii  ipcrldvpqn  lmfgkwkyek
        61       pdgspvfiaf  rsstkksvqy  ddvpeykdrl  nlsenytlsi  snarisdekr  fvcmlvtedn
       121       vfeaptivkv  fkqpskpeiv  skalfleteq  lkklgdcise  dsypdgnitw  yrngkvlhpl
       181       egavviifkk  emdpvtqlyt  mtstleyktt  kadiqmpftc  svtyygpsgq  ktihseqavf
       241       diyypteqvt  iqvlppknai  kegdnitlkc  lgngnpppee  flfylpgqpe  girssntytl
       301       tdvrrnatgd  ykcslidkks  miastaitvh  yldlslnpsg  evtrqigdal  pvsctisasr
       361       natvvwmkdn  irlrsspsfs  slhyqdagny  vcetalqeve  glkkresltl  ivegkpqikm
       421       tkktdpsgls  ktiichvegf  pkpaiqwtit  gsgsvinqte  espyingryy  skiiispeen
       481       vtltctaenq  lertvnslnv  saisipehde  adeisdenre  kvndqakliv  givvglllaa
       541       lvagvvywly  mkksktaskh  vnkdlgnmee  nkkleennhk  tea
```

TABLE 2-continued

```
Gene ID:              X2
Gene symbol:          ATP1A1
Gene description:     sodium/potassium-transporting ATPase subunit alpha-1
Unigene:              Hs.371889
Genbank:              BC003077
Entrez Gene:          476
Refseq:               NM_000701 | NM_001160233 | NM_001160234
Protein sequence isoform a (SEQ ID NO (2)):
           1   mgkgvgrdky epaayseqgd kkgkkgkkdr dmdelkkevs mddhklslde lhrkygtdls
          61   rgltsaraae ilardgpnal tpppttpewi kfcrqlfggf smllwigail cflaysiqaa
         121   teeepqndnl ylgvvlsavv iitgcfsyyq eaksskimes fknmvpqqal virngekmsi
         181   naeevvvgdl vevkggdrip adlriisang ckvdnssltg esepqtrspd ftnenpletr
         241   niaffstncv egtargivvy tgdrtvmgri atlasglegg qtpiaaeieh fihiitgvav
         301   flgvsffils lileytwlea vifligiiva nvpegllatv tvcltltakr marknclvkn
         361   leavetlgst sticsdktgt ltqnrmtvah mwfdnqihea dttenqsgvs fdktsatwla
         421   lsriaglcnr avfqangenl pilkravagd asesallkci elccgsvkem reryakivei
         481   pfnstnkyql sihknpntse pqhllvmkga perildrcss illhgkeqpl deelkdafqn
         541   aylelgglge rvlgfchlfl pdeqfpegfq fdtddvnfpi dnlcfvglis midppraavp
         601   davgkcrsag ikvimvtgdh pitakaiakg vgiisegnet vediaarlni pvsqvnprda
         661   kacvvhgsdl kdmtseqldd ilkyhteivf artspqqkli ivegcqrqga ivavtgdgvn
         721   dspalkkadi gvamgiagsd vskqaadmil lddnfasivt gveegrlifd nlkksiaytl
         781   tsnipeitpf lifiianipl plgtvtilci dlgtdmvpai slayeqaesd imkrqprnpk
         841   tdklvnerli smaygqigmi qalggffty f vilaengflp ihllglrvdw ddrwindved
         901   sygqqwtyeq rkiveftcht affvsivvvq wadlvicktr rnsvfqqgmk nkilifglfe
         961   etalaaflsy cpgmgvalrm yplkptwwfc afpysllify ydevrkliir rrpggwveke
        1021   tyy Protein sequence isoform c (SEQ ID NO (3)):
           1   mafkvgrdky epaayseqgd kkgkkgkkdr dmdelkkevs mddhklslde lhrkygtdls
          61   rgltsaraae ilardgpnal tpppttpewi kfcrqlfggf smllwigail cflaysiqaa
         121   teeepqndnl ylgvvlsavv iitgcfsyyq eaksskimes fknmvpqqal virngekmsi
         181   naeevvvgdl vevkggdrip adlriisang ckvdnssltg esepqtrspd ftnenpletr
         241   niaffstncv egtargivvy tgdrtvmgri atlasglegg qtpiaaeieh fihiitgvav
         301   flgvsffils lileytwlea vifligiiva nvpegllatv tvcltltakr marknclvkn
         361   leavetlgst sticsdktgt ltqnrmtvah mwfdnqihea dttenqsgvs fdktsatwla
         421   lsriaglcnr avfqangenl pilkravagd asesallkci elccgsvkem reryakivei
         481   pfnstnkyql sihknpntse pqhllvmkga perildrcss illhgkeqpl deelkdafqn
         541   aylelgglge rvlgfchlfl pdeqfpegfq fdtddvnfpi dnlcfvglis midppraavp
         601   davgkcrsag ikvimvtgdh pitakaiakg vgiisegnet vediaarlni pvsqvnprda
         661   kacvvhgsdl kdmtseqldd ilkyhteivf artspqqkli ivegcqrqga ivavtgdgvn
         721   dspalkkadi gvamgiagsd vskqaadmil lddnfasivt gveegrlifd nlkksiaytl
         781   tsnipeitpf lifiianipl plgtvtilci dlgtdmvpai slayeqaesd imkrqprnpk
         841   tdklvnerli smaygqigmi qalggfftyf vilaengflp ihllglrvdw ddrwindved
         901   sygqqwtyeq rkiveftcht affvsivvvq wadlvicktr rnsvfqqgmk nkilifglfe
         961   etalaaflsy cpgmgvalrm yplkptwwfc afpysllify ydevrkliir rrpggwveke
        1021   tyy Protein sequence isoform d (SEQ ID NO (4)):
           1   mdelkkevsm ddhklslsdel hrkygtdlsr gltsaraaei lardgpnalt ppptttpewik
          61   fcrqlfggfs mllwigailc flaysiqaat eeepqndnly lgvvlsavvi itgcfsyyqe
         121   aksskimesf knmvpqqalv irngekmsin aeevvvgdlv evkggdripa dlriisangc
         181   kvdnssltge sepqtrspdf tnenpletrn iaffstncve gtargivvyt gdrtvmgria
         241   tlasgleggq tpiaaeiehf ihiitgvavf lgvsffilsl ileytwleav ifligiivan
         301   vpegllatvt vcltltakrm arknclvknl eavetlgsts ticsdktgtl tqnrmtvahm
         361   wfdnqihead ttenqsgvsf dktsatwlal sriaglcnra vfqangenlp ilkravagda
         421   sesallkcie lccgsvkemr eryakiveip fnstnkyqls ihknpntsep qhllvmkgap
         481   erildrcssi llhgkeqpld eelkdafqna ylelgglger vlgfchlflp deqfpegfqf
         541   dtddvnfpid nlcfvglism idppraavpd avgkcrsagi kvimvtgdhp itakaiakgv
         601   giisegnetv ediaarlnip vsqvnprdak acvvhgsdlk dmtseqlddi lkyhteivfa
         661   rtspqqklii vegcqrqgai vavtgdgvnd spalkkadig vamgiagsdv skqaadmill
         721   ddnfasivtg veegrlifdn lkksiaytlt snipeitpfl ifiianiplp lgtvtilcid
         781   lgtdmvpais layeqaesdi mkrqprnpkt dklvnerlis maygqigmiq alggfftyfv
         841   ilaengflpi hllglrvdwd drwindveds ygqqwtyeqr kiveftchta ffvsivvvqw
         901   adlvicktrr nsvfqqgmkn kilifglfee talaaflsyc pgmgvalrmy plkptwwfca
         961   fpysllifvy devrkliirr rpggwveket yy Gene ID:              X3
Gene symbol:          CD200
Gene description:     CD 200 molecule
Unigene:              Hs.79015
Genbank:              AK297194 | AF063591 | BC022522 | BC031103 | AY603771 | AK293399
Entrez Gene:          4345
Refseq:               NM_001004196 | NM_005944
Protein sequence isoform b (SEQ ID NO (5)):
           1   merltltrti ggplltatll gkttindyqv irmpfshlst yslvwvmaav vlctaqvqw
          61   tqdereqlyt paslkcslqn aqealivtwq kkkayspenm vtfsenhgvv iqpaykdkin
         121   itqlglqnst itfwnitled egcymclfnt fgfgkisgta cltvyvqpiv slhykfsedh
         181   lnitcsatar papmvfwkvp rsgienstvt lshpngttsv tsilhikdpk nqvgkevicq
         241   vlhlgtvtdf kqtvnkgywf svplllsivs lvillvlisi llywkrhrnq drep
```

TABLE 2-continued

```
Protein sequence isoform a (SEQ ID NO (6)):
         1    merlvirmpf shlstyslvw vmaavvlcta qvqvvtqder eqlytpaslk cslqnaqeal
        61    ivtwqkkkav spenmvtfse nhgvviqpay kdkinitqlg lqnstitfwn itledegcym
       121    clfnifgfgk isgtacltvy vqpivslhyk fsedhlnitc satarpapmv fwkvprsgie
       181    nstvtlshpn gttsvtsilh ikdpknqvgk evicqvlhlg tvtdfkqtvn kgywfsvpll
       241    lsivslvill vlisillywk rhrnqdrep
```

Gene ID:             X4
Gene symbol:         LAMB1
Gene description:    laminin, beta 1
Unigene:             Hs.650585
Genbank:             M61916
Entrez Gene:         3912
Refseq:              NM_002291
Protein sequence (SEQ ID NO (7)):
```
         1    mgllqllafs flalcrarvr aqepefsygc aegscypatg dlligraqkl svtstcglhk
        61    pepycivshl qedkkcficn sqdpyhetln pdshlienvv ttfapnrlki wwqsengven
       121    vtiqldleae fhfthlimtf ktfrpaamli erssdfgktw gvyryfaydc easfpgistg
       181    pmkkvddiic dsrysdieps tegevifral dpafkiedpy sprignlli tnlrikfvkl
       241    htlgdnllds rmeirekyyy avydmvvrgn cfcyghasec apvdgfneev egmvhghcmc
       301    rhntkglnce lcmdfyhdlp wrpaegrnsn ackkcncneh sischfdmav ylatgnvsgg
       361    vcddcqhntm grnceqckpf yyqhperdir dpnfcerctc dpagsqnegi cdsytdfstg
       421    liaggcrckl nvegehcdvc kegfydlsse dpfgckscac nplgtipggn pcdsetghcy
       481    ckrlvtgqhc dqclpehwgl sndldgcrpc dcdlggalnn scfaesgqcs crphmigrqc
       541    nevepgyyfa tldhylyeaa eanlgpgvsi verqyiqdri pswtgagfvr vpegayleff
       601    idnipysmey diliryepql pdhwekavit vqrpgripts srcgntipdd dnqvvslspg
       661    sryvvlprpv cfekgtnytv rlelpqytss dsdvespytl idslvlmpyc ksldiftvgg
       721    sgdgvvtnsa wetfqryrcl ensrsvvktp mtdvcrniif sisallhqtg lacecdpqgs
       781    lssvcdpngg qcqcrpnvvg rtcnrcapgt fgfgpsgckp cechlqgsvn afcnpvtggc
       841    hcfqgvyarq cdrclpghwg fpscqpcqcn ghaddcdpvt geclncqdyt mghncercla
       901    gyygdpiigs gdhcrpcpcp dgpdsgrqfa rscyqdpvtl qlacvcdpgy igsrcddcas
       961    gyfgnpsevg gscqpcqchn nidttdpeac dketgrclkc lyhtegehcq fcrfgtygda
      1021    lqqdcrkcvc nylgtvqehc ngsdcqcdka tgqclclpnv iggncdreap ntwqlasgtg
      1081    cdpcncnaah sfgpscneft gqcqcmpgfg grtcsecqel fwgdpdvecr acdcdprgie
      1141    tpqcdqstgq cvcvegvegp rcdkctrgys gvfpdctpch qcfalwdvii aeltnrthrf
      1201    lekakalkis gvigpyretv dsverkvsei kdilaqspaa eplknignlf eeaeklikdv
      1261    temmaqvevk lsdttsqsns takeldslqt easldntvk elaeqlefik nsdirgalds
      1321    itkyfqmsle aeervnastt epnstveqsa lmrdrvedvm meresqfkek qeeqarllde
      1381    lagklqsldl saaaemtcgt ppgascsete cggpncrtde gerkcggpgc gglvtvahna
      1441    wqkamdldqd vlsalaeveq lskmvseakl radeakqsae dillktnatk ekmdksneel
      1501    rnlikqirnf ltqdsadlds ieavanevlk mempstpqql qnltedirer veslsqvevi
      1561    lqhsaadiar aemlleeakr asksatdvkv tadmvkeale eaekaqvaae kaikqadedi
      1621    qgtqnlltsi esetaaseet lfnasqrise lernveelkr kaaqnsgeae yiekvvytvk
      1681    qsaedvkktl dgeldekykk venliakkte esadarrkae mlqneaktll aqansklqll
      1741    kdlerkyedn qryledkaqe larlegevrs llkdisqkva vystcl
```

Gene ID:             X5
Gene symbol:         CD248
Gene description:    endosialin
Unigene:             Hs.195727
Genbank:             AF279142
Entrez Gene:         57124
Refseq:              NM_020404
Protein sequence (SEQ ID NO (8)):
```
         1    mllrlllawa aagptlgqdp waaepraacg psscyalfpr rrtfleawra crelggdlat
        61    prtpeeaqrv dslvgagpas rllwiglqrq arqcqlqrpl rgftwttgdq dtaftnwaqp
       121    asggpcpaqr cvaleasgeh rwlegsctla vdgylcqfgf egacpalqde agqagpavyt
       181    tpfhlvstef ewlpfgsvaa vqcqagrgas llcvkqpegg vgwsragplc lgtgcspdng
       241    gcehecveev dghvscrcte gfrlaadgrs cedpcaqapc eqqcepggpq gyschcrlgf
       301    rpaeddphrc vdtdecqiag vcqqmcvnyv ggfecycseg headgisc spagamgaqa
       361    sqdlgdelld dgedeedede awkafnggwt empgilwmep tqppdfalay rpsfpedrep
       421    qipypeptwp pplsaprvpy hssvlsvtrp vvvsathptl psahqppvip athpalsrdh
       481    qipviaanyp dlpsayqpgi lsvshsaqpp ahqppmistk ypelfpahqs pmfpdtrvag
       541    tqttthlpgi ppnhaplvtt lgaqlppqap dalvlrtqat qlpiiptaqp slttsrspv
       601    spahqisvpa atqpaalptl lpsqsptnqt spispthphs kapqipredg pspklawlp
       661    spaptaapta lgeaglaehs qrddrwllva llvptcvflv vllalgivyc trcgphapnk
       721    ritdcyrwvi hagskstep mpprgsltgv qtcrtsv
```

Gene ID:             X6
Gene symbol:         COL4A6
Gene description:    collagen, type IV, alpha 6
Unigene:             Hs.145586
Genbank:             D21337
Entrez Gene:         1288
Refseq:              NM_033641 | NM_001847
Protein sequence isoform b (SEQ ID NO (9)):
```
         1    mhpglwlllv tlclteelaa ageksygkpc ggqdcsgscq cfpekgargr pgpigiqgpt
        61    gpqgftgstg lsglkgergf pgllgpygpk gdkgpmgvpg flgingipgh pgqpgprgpp
       121    gldgcngtqg avgfpgpdgy pgllgppglp gqkgskgdpv lapgsfkgmk gdpglpgldg
       181    itgpqgapgf pgavgpagpp glqgppgppg plgpdnmgl gfqgekgvkg dvglpgpagp
```

TABLE 2-continued

```
       241   ppstgelefm  gfpkgkkgsk  gepgpkgfpg  isgppgfpgl  gttgekgekg  ekgipglpgp
       301   rgpmgsegvq  gppgqqgkkg  tlgfpglngf  qgiegqkgdi  glpgpdvfid  idgavisgnp
       361   gdpgvpglpg  lkgdegiqgl  rgpsgvpglp  alsgvpgalg  pqgfpglkgd  qgnpgrttig
       421   aaglpgrdgl  pgppgppgpp  spefetetlh  nkesgfpglr  geqgpkgnlg  lkgikgdsgf
       481   cacdggvpnt  gppgepgppg  pwgligIlpgl kgargdrgsg  gaqgpagapg  lvgvplgpsgp
       541   kgkkgepils  tiqgmpgdrg  dsgsqgfrgv  igepgkdgvp  glpglpglpg  dggqgfpgek
       601   glpglpgekg  hpgppglpgn  glpglpgprg  lpgdkgkdgl  pggqqglpgsk  gitlpciipg
       661   sygpsgfpgt  pgfpgpkgsr  glpgtpgqpg  ssgskgepgs  pglvhlpelp  gfpgprgekg
       721   lpgfpglpgk  dglpgmigsp  glpgskgatg  difgaengap  geqglqgltg  hkgflgdsgl
       781   pglkgvhgkp  gllgpkgerg  spgtpgqvgq  pgtpgsssgpy gikgksglpg  apgfpgisgh
       841   pgkkgtrgkk  gppgsivkkg  lpglkglpgn  pglvglkgsp  gspgvaglpa  lsgpkgekgs
       901   vgfvgfpgip  glpgipgtrg  lkgipgstgk  mgpsgragtp  gekgdrgnpg  pvgipsprrp
       961   msnlwlkgdk  gsqgsagsng  fpgprgdkge  agrpgppglp  gapglpgiik  gvsgkpgppg
      1021   fmgirglpgl  kgssgitgfp  gmpgesgsqg  irgspglpga  sglpglkgdn  gqtveisgsp
      1081   gpkgqpgesg  fkgtkgrdgl  ignigfpgnk  gedgkvgvsg  dvglpgapgf  pgvagmrgep
      1141   glpgssghqg  aigplgspgl  igpkgfpgfp  glhglnglpg  tkgthgtpgp  sitgvpgpag
      1201   lpgpkgekgy  pgigigapgk  pglrgqkgdr  gfpglqgpag  lpgapgislp  sliagqpgdg
      1261   grpgldgerg  rpgpagppgp  pgpssnqgdt  gdpgfpgipg  pkgpkgdqgi  pgfsglpgel
      1321   glkgmrgepg  fmgtpgkvgp  pgdpgfpgmk  gkagprgssg  lqgdpgqtpt  aeavqvppgp
      1381   lglpgidgip  gltgdpgaqg  pvglqgskgl  pgipgkdgps  glpgppgalg  dpglpglqgp
      1441   pgfegapgqq  gpfgmpgmpg  qsmrvgytlv  khsqseqvpy  cpigmsqlwv  gysllfvegq
      1501   ekahnqdlgf  agsclprfst  mpfiycnine  vchyarrndk  sywlsttapi  pmmmpvsqtqi
      1561   pqyisrcsvc  eapsqaiavh  sqditipqcp  lgwrslwigy  sflmhtaaga  egggqslvsp
      1621   gscledfrat  pfiecsgarg  tchyfankys  fwlttveerq  qfgelpvset  lkagqlhtrv
      1681   srcqvcmksl
Protein sequence isoform a (SEQ ID NO (10)):
         1   mlinklwlll  vtlclteela  aagekysygkp cggqdcsgsc  qcfpekgarg  rpgpigiqgp
        61   tgpqgftgst  glsglkgerg  fpgllgpygp  kgdkgpmgvp  gflgingipg  hpgqpgrgp
       121   pgldgcngtq  gavgfpgpdg  vpgllgppgl  pgqkgskgdp  vlapgsfkgm  kgdpglpgld
       181   gitgpqgapg  fpgavgpagp  pglqgppgpp  gplpgdgnmg  lgfqgekgvk  gdvglpgpag
       241   pppstgelef  mgfpkgkkgs  kgepgpkgfp  gisgppgfpg  lgttgekgek  gekgipglpg
       301   prgpmgsegv  qgppgqqgkk  gtlgfpglng  fqgiegqkgd  iglpgpdvfi  didgavisgn
       361   pgdpgvpglp  glkgdegiqg  lrgpsgvpgl  palsgvpgal  gpqgfpglkg  dqgnpgrtti
       421   gaaglpgrdg  lpgppgppgp  pspefetetl  hnkesgfpgl  rgeqgpkgnl  glkgikgdsg
       481   fcacdggvpn  tgppgepgpp  gpwgliglpg  lkgargdrgs  ggaqgpagap  glvgplpgsg
       541   pkgkkgepil  stiqgmpgdr  gdsgsqgfrg  vigepgkdgv  pglpglpglp  gdggqgfpge
       601   kglpglpgek  ghpgppglpg  nglpglpgpr  glpgdkgkdg  lpgqqglpgs  kgitlpciip
       661   gsygpsgfpg  tpgfpgpkgs  rglpgtpgqp  gssgskgepg  spglvhlpel  pgfpgprgek
       721   glpgfpglpg  kdglpgmigs  pglpgskgat  gdifgaenga  pgeqglqglt  ghkgflgdsg
       781   lpglkgvhgk  pgllgpkger  gspgtpgqvg  qpgtpgssgp  ygikgksglp  gapgfpgisg
       841   hpgkkgtrgk  kgppgsivkk  glpglkglpg  npglvglkgs  pgspgvaglp  alsgpkgekg
       901   svgfvgfpgi  pglpgipgtr  glkgipgstg  kmgpsgragt  pgekgdrgnp  gpvgipsprr
       961   pmsnlwlkgd  kgsqgsagsn  gfpgprgdkg  eagrpgppgl  pgapglpgii  kgvsgkpgpp
      1021   gfmgirglpg  lkgssgitgf  pgmpgesgsq  girgspglpg  asglpglkgd  ngqtveisgs
      1081   pgpkgqpges  gfkgtkgrdg  lignigfpgn  kgedgkvgvs  gdvglpgapg  fpgvagmrge
      1141   pglpgssghq  gaigplgspg  ligpkgfpgf  pglhglnglp  gtkgthgtpg  psitgvpgpa
      1201   glpgpkgekg  ypgigigapg  kpglrgqkgd  rgfpglqgpa  glpgapgisl  psliagqpgd
      1261   pgrpgldger  grpgpagppg  pgpssnqgd   tgdpgfpgip  gpkgpkgdqg  ipgfsglpge
      1321   lglkgmrgep  gfmgtpgkvg  ppgdpgfpgm  gkagprgssg  lqgdpgqtpt  aeavqvppgp
      1381   plglpgidgi  pgltgdpgaq  gpvglqgskg  lpgipgkdgp  sglpgppgal  gdpglpglqg
      1441   ppgfegapgq  qgpfgmpgmp  gqsmrvgytl  vkhsqseqvp  cpigmsqlw  vgysllfveg
      1501   qekahnqdlg  fagsclprfs  tmpfiycnin  evchyarrnd  ksywlsttap  ipmmpvsqtq
      1561   ipqyisrcsv  ceapsqaiav  hsqditipqc  plgwrslwig  ysflmhtaag  aeggqslvs
      1621   pgscledfra  tpfiecsgar  gtchyfanky  sfwlttveer  qqfgelpvse  tlkagqlhtr
      1681   vsrcqvcmks  l
```

Gene ID:            X7
Gene symbol:        PCDH7
Gene description:   protocadherin 7
Unigene:            Hs.479439 | Hs.724529
Genbank:            AB006755
Entrez Gene:        5099
Refseq:             NM_032456 | NM_002589 | NM_032457 | NM_001173523
Protein sequence isoform b (SEQ ID NO (11)):

```
         1   mlrmrtagwa  rgwelgccll  lplslslaaa  kqllryrlae  egpadvrign  vasdlgivtg
        61   sgevtfsles  gseylkidnl  tgelstserr  mifdenecfl  dfevsvigps
       121   qswvdlfegq  vivldindnt  ptfspsvltl  tveenrpvgt  lyllptatdr  dfgrngiery
       181   ellqepgggg  sggesrraga  adsapypggg  gngasgggsg  gskrrldase  ggggtnpggr
       241   ssvfelqvad  tpdgekqpql  ivkgaldreq  rdsyeltlrv  rdggdpprss  qailrvlitd
       301   vndnsprfek  svyeadlaen  sapgtpilql  raadldvgvn  gqieyvfgaa  tesvrrllrl
       361   detsgwlsvl  hridreevnq  lrftvmardr  gqppktdkat  vvlnikdend  nvpsieirki
       421   griplkdgva  nvaedvlvdt  pialvqvsdr  dqgengvvtc  tvvgdvpfql  kpasdtegdq
       481   nkkkyflhts  tpldyeatre  fnvvivavds  gspslssnns  livkvgdtnd  nppmfgqsvv
       541   evyfpennip  gervatvlat  dadsgknaei  ayslssvmg  ifaidpdsgd  ilvntldre
       601   qtdryefkvn  akdkgipvlq  gsttvivqva  dkndndpkfm  qdvftfyvke  nlqpnspvgm
       661   vtvmdadkgr  naemslyiee  nnnifsiend  tgtiystmsf  drehqttytf  rvkavdggdp
       721   prsatatvsl  fvmdendnap  tvtlpknisy  tllppssnvr  tvvatvlatd  sddginadln
       781   ysivggnpfk  lfeidptsgv  vslvgkltqk  hyglhrlvvq  vndsgqpsqs  tttlvhvfvn
       841   esvsnataid  sqiarslhip  ltqdiagdps  yeiskqrlsi  vigvvagimt  viliilivvm
```

TABLE 2-continued

```
       901  arycrsknkn  gyeagkkdhe  dfftpqqhdk  skkpkkdkkn  kkskqplyss  ivtveaskpn
       961  gqrydsvnek  lsdspsmgry  rsvnggpgsp  dlarhyksss  plptvqlhpq  sptagkkhqa
      1021  vqdlppantf  vgagdnisig  sdhcseyscq  tnnkyskqvr  cipnifkypr  eg Protein sequence isoform a (SEQ ID NO (12)):
         1  mlrmrtagwa  rgwelgccll  lplslslaaa  kqllryrlae  egpadvrign  vasdlgivtg
        61  sgevtfsles  gseylkidnl  tgelstserr  idreklpqcq  mifdenecfl  dfevsvigps
       121  qsvwdlfegq  vivldindnt  ptfpspvltl  tveenrpvgt  lyllptatdr  dfgrngiery
       181  ellqepgggg  sggesrraga  adsapypggg  ngasgggsg  gskrrldase  ggggtnpggr
       241  ssvfelqvad  tpdgekqpql  ivkgaldreq  rdsyeltlrv  rdggdpprss  qailrvlitd
       301  vndnsprfek  svyeadlaen  sapgtpilql  raadldvgvn  gqieyvfgaa  tesvrrllrl
       361  detsgwlsvl  hridreevnq  lrftvmardr  gqppktdkat  vvlnikdend  nvpsieirki
       421  griplkdgva  nvaedvlvdt  pialvqvsdr  dqgengvvtc  tvvgdvpfql  kpasdtegdq
       481  nkkkyflhts  tpldyeatre  fnvvivavds  gspslssnns  livkvgdtnd  nppmfgqsvv
       541  evyfpennip  gervatvlat  dadsgknaei  aysldssvmg  ifaidpdsgd  ilvntvldre
       601  qtdryefkvn  akdkgipvlq  gsttvivqva  dkndndpkfm  qdvftfyvke  nlqpnspvgm
       661  vtvmdadkgr  naemslyiee  nnnifsiend  tgtiystmsf  drehqttytf  rvkavdggdp
       721  prsatatvsl  fvmdendnap  tvtlpknisy  tllppssnvr  tvvatvlatd  sddginadln
       781  ysivggnpfk  lfeidptsgv  vslvgkltqk  hyglhrlvvq  vndsgqpsqs  ttttlvhvfvn
       841  esysnataid  sqiarslhip  ltqdiagdps  yeiskqrlsi  vigvvagimt  viliilivvm
       901  arycrsknkn  gyeagkkdhe  dfftpqqhdk  skkpkkdkkn  kkskqplyss  ivtveaskpn
       961  gqrydsvnek  lsdspsmgry  rsvnggpgsp  dlarhyksss  plptvqlhpq  sptagkkhqa
      1021  vqdlppantf  vgagdnisig  sdhcseyscq  tnnkyskqmr  lhpyitvfg Protein sequence isoform c (SEQ ID NO (13)):
         1  mlrmrtagwa  rgwelgccll  lplslslaaa  kqllryrlae  egpadvrign  vasdlgivtg
        61  sgevtfsles  gseylkidnl  tgelstserr  idreklpqcq  mifdenecfl  dfevsvigps
       121  qswvdlfegq  vivldindnt  ptfpspvltl  tveenrpvgt  lyllptatdr  dfgrngiery
       181  ellqepgggg  sggesrraga  adsapypggg  ngasgggsg  gskrrldase  ggggtnpggr
       241  ssvfelqvad  tpdgekqpql  ivkgaldreq  rdsyeltlrv  rdggdpprss  qailrvlitd
       301  vndnsprfek  svyeadlaen  sapgtpilql  raadldvgvn  gqieyvfgaa  tesvrrllrl
       361  detsgwlsvl  hridreevnq  lrftvmardr  gqppktdkat  vvlnikdend  nvpsieirki
       421  griplkdgva  nvaedvlvdt  pialvqvsdr  dqgengvvtc  tvvgdvpfql  kpasdtegdq
       481  nkkkyflhts  tpldyeatre  fnvvivavds  gspslssnns  livkvgdtnd  nppmfgqsvv
       541  evyfpennip  gervatvlat  dadsgknaei  aysldssvmg  ifaidpdsgd  ilvntvldre
       601  qtdryefkvn  akdkgipvlq  gsttvivqva  dkndndpkfm  qdvftfyvke  nlqpnspvgm
       661  vtvmdadkgr  naemslyiee  nnnifsiend  tgtiystmsf  drehqttytf  rvkavdggdp
       721  prsatatvsl  fvmdendnap  tvtlpknisy  tllppssnvr  tvvatvlatd  sddginadln
       781  ysivggnpfk  lfeidptsgv  vslvgkltqk  hyglhrlvvq  vndsgqpsqs  ttttlvhvfvn
       841  esvsnataid  sqiarslhip  ltqdiagdps  yeiskqrlsi  vigvvagimt  viliilivvm
       901  arycrsknkn  gyeagkkdhe  dfftpqqhdk  skkpkkdkkn  kkskqplyss  ivtveaskpn
       961  gqrydsvnek  lsdspsmgry  rsvnggpgsp  dlarhyksss  plptvqlhpq  sptagkkhqa
      1021  vqdlppantf  vgagdnisig  sdhcseyscq  tnnkyskqpf  rrvtfsvvsq  pqdphqgslq
      1081  scydsglees  etpssksssg  prlgalplpe  dnyerttpdg  svdsrplpdv  altgkctrec
      1141  deyghsdscw  mpvrtsperk  ksqpklstfm  pvdergsqek  langeaaimg  drnrnllnkk
      1201  ltssyeffsa  asfskneean  pedipltktg  eykpspvntl  trrevyl Protein sequence isoform d (SEQ ID NO (14)):
         1  mlrmrtagwa  rgwclgccll  lplslslaaa  kqllryrlae  egpadvrign  vasdlgivtg
        61  sgevtfsles  gseylkidni  tgelstserr  idreklpqcq  mifdenecfl  dfevsvigps
       121  qswvdlfegq  vivldindnt  ptfpspvltl  tveenrpvgt  lyllptatdr  dfgrngiery
       181  ellqepgggg  sggesrraga  adsapypggg  ngasgggsg  gskrrldase  ggggtnpggr
       241  ssvfelqvad  tpdgekqpql  ivkgaldreq  rdsyeltlrv  rdggdpprss  qailrvlitd
       301  vndnsprfek  svyeadlaen  sapgtpilql  raadldvgvn  gqieyvfgaa  tesvrrllrl
       361  detsgwlsvl  hridreevnq  lrftvmardr  gqppktdkat  vvlnikdend  nvpsieirki
       421  griplkdgva  nvaedvlvdt  pialvqvsdr  dqgengvvtc  tvvgdvpfql  kpasdtegdq
       481  nkkkyflhts  tpldyeatre  fnvvivavds  gspslssnns  livkvgdtnd  nppmfgqsvv
       541  evyfpennip  gervatvlat  dadsgknaei  aysldssvmg  ifaidpdsgd  ilvntvldre
       601  qtdryefkvn  akdkgipvlq  gsttvivqva  dkndndpkfm  qdvftfyvke  nlqpnspvgm
       661  vtvmdadkgr  naemslyiee  nnnifsiend  tgtiystmsf  drehqttytf  rvkavdggdp
       721  prsatatvsl  fvmdendnap  tvtlpknisy  tllppssnvr  tvvatvlatd  sddginadln
       781  ysivggnpfk  lfeidptsgv  vslvgkltqk  hyglhrlvvq  vndsgqpsqs  ttttlvhvfvn
       841  esvsnataid  sqiarslhip  ltqdiagdps  yeiskqrlsi  vigvvagimt  viliilivvm
       901  arycrsknkn  gyeagkkdhe  dfftpqqhdk  skkpkkdkkn  kkskqplyss  ivtveaskpn
       961  gqrydsvnek  lsdspsmgry  rsvnggpgsp  dlarhyksss  plptvqlhpq  sptagkkhqa
      1021  vqdlppantf  vgagdnisig  sdhcseyscq  tnnkyskqpf  rrylfsvvsq  pqdphqgslq
      1081  scydsglees  etpssksssg  prlgalplpe  dnyerttpdg  svgeaehmen  dsrplpdval
      1141  tgkctrecde  yghsdscwmp  vrtsperkks  qpklstfmpv  dergsqekla  ngeaaimgdr
      1201  nrnllnkklt  ssyetfsaas  fskneeanpe  dipltktgey  kpspvntltr  revyl
```

Gene ID:         X8
Gene symbol:     NOG
Gene description: noggin
Unigene:         Hs.248201
Genbank:         BC034027
Entrez Gene:     9241
Refseq:          NM_005450
Protein sequence (SEQ ID NO(15)):

```
         1  mercpslgvt  lyalvvvlgl  ratpaggqhy  lhirpapsdn  lplvdliehp  dpifdpkekd
        61  lnetllrsll  gghydpgfma  tsppedrpgg  gggaaggaed  laeldqllrq  rpsgampsei
```

TABLE 2-continued

```
       121    kglefsegla qgkkqrlskk lrrklqmwlw sqtfcpvlya wndlgsrfwp ryvkvgscfs
       181    krscsvpegm vckpsksvhl tvlrwrcqrr ggqrcgwipi qypiiseckc sc Gene ID:                X9
Gene symbol:            SULF1
Gene description:       sulfatase 1
Unigene:                Hs.409602
Genbank:                AF545571
Entrez Gene:            23213
Refseq:                 NM_001128205 | NM_015170 | NM_001128206 | NM_001128204
Protein sequence (SEQ ID NO(16)):
         1    mkysccalvl avlgtellgs lcstvrsprf rgriqqerkn irpniilvlt ddqdvelgsl
        61    qvmnktrkim ehggatfina fvttpmccps rssmltgkyv hnhnvytnne ncsspswqam
       121    heprtfavyl nntgyrtaff gkylneyngs yippgwrewl gliknsrlyn ytvcrngike
       181    khgfdyakdy ftdlitnesi nyfkmskrmy phrpvmmvis haaphgpeds apqfsklypn
       241    asqhitpsyn yapnmdkhwi mqytgpmlpi hmeftnilqr krlqtlmsvd dsverlynml
       301    vetgelenty iiytadhgyh igqfglvkgk smpydfditd pffirgpsve pgsivpqivl
       361    nidlaptild iagldtppdv dgksvlklld pekpgnrfrt nkkakiwrdt flvergkflr
       421    kkeesskniq qsnhlpkyer vkelcqqary qtaceqpgqk wqciedtsgk lrihkckgps
       481    dlltvrqstr nlyargfhdk dkecscresg yrasrsqrks qrqflrnqgt pkykprfvht
       541    rqtrslsvef egeiydinle eeeelqvlqp rniakrhdeg hkgprdlqas sggnrgrmla
       601    dssnavgppt tvrvthkcfi lpndsihcer elyqsarawk dhkayidkei ealqdkiknl
       661    revrghlkrr kpeecscskq syynkekgvk kqeklkshlh pfkeaaqevd sklqlfkenn
       721    rrrkkerkek rrqrkgeecs lpgltcfthd nnhwqtapfw nlgsfcacts snnntywclr
       781    tvnethnflf cefatgfley fdmntdpyql tntvhtverg ilnqlhvqlm elrscqgykq
       841    cnprpknldv gnkdggsydl hrgqlwdgwe g Gene ID:                X10
Gene symbol:            SORT1
Gene description:       sortilin 1
Unigene:                Hs.485195
Genbank:                X98248
Entrez Gene:            6272
Refseq:                 NM_002959 | NM_001205228
Protein sequence isoform 1 (SEQ ID NO (17)):
         1    merpwgaadg lsrwphglgl llllqllpps tlsqdrldap pppaaplprw sgpigvswgl
        61    raaaaggafp rggrwrrsap gedeeecgrvr dfvaklannt hqhvfddlrg syslswvgds
       121    tgvilvlttf hvplvimtfg qsklyrsedy gknfkfdidl inntfirtef gmaigpensg
       181    kvvltaevsg gsrggrifts sdfaknfvqt dlpfhpltqm myspqnsdyl lalstenglw
       241    vsknfggkwe eihkavclak wgsdntifft tyangsckad lgalelwrts dlgksfktig
       301    vkiysfglgg rflfasvmad kdttrrihvs tdqgdtwsma qlpsvgqeqf ysilaanddm
       361    vfmhvdepgd tgfgtiftsd drgivysksl drhlytttgy etdftnvtsl rgvyitsvls
       421    ednsiqtmit fdqggrwthl rkpensecda taknknecsl hihasysisq klnvpmapls
       481    epnavgivia hgsvgdaisv mvpdvyisdd ggyswtkmle gphyytilds ggiivaiehs
       541    srpinvikfs tdeqgcwqty tftrdpiyft glasepgars mnisiwgfte sfltsqwvsy
       601    tidfkdiler nceekdytiw lahstdpedy edgcilgye qflrlrkssv cqngrdyvvt
       661    kqpsicicsl edflcdfgyy rpendskcve qpelkghdle fclygreehl ttngyrkipg
       721    dkcqggvnpv revkdlkkkc tsnflspekq nsksnsvpii laivglmlvt vvagvlivkk
       781    yvcggrflvh rysvlqqhae angvdgvdal dtashtnksg yhddsdedll e Protein sequence isoform 2 (SEQ ID NO (18)):
         1    mtfgqsklyr sedygknfkd itdlinntfi rtefgmaigp ensgkvvlta evsggsrggr
        61    ifrssdfakn fvqtdlpfhp ltqmmyspqn sdyllalste nglwvsknfg gkweeihkav
       121    clakwgsdnt iffttyangs ctdlgalelw rtsdlgksfk tigvkiysfg lggrflfasv
       181    madkdttrri hvstdqgdtw smaqlpsvgq eqfysilaan ddmvfmhvde pgdtgfgtif
       241    tsddrgivys ksldrhlytt tggetdftnv tslrgvyits vlsednsiqt mitfdqggrw
       301    thlrkpense cdataknkne cslhihasys isqklnvpma plsepnavgi viahgsvgda
       361    isvmvpdvyi sddggyswtk mlegphyyti ldsggiivai ehssrpinvi kfstdeqgcw
       421    qtytftrdpi yftglasepg arsmnisiwg ftesfltsqw vsytidfkdi lernceekdy
       481    tiwlahstdp edyedgcilg ykeqflrlrk ssvcqngrdy vvtkqpsicl csledflcdf
       541    gyyrpendsk cveqpelkgh dlefclygre ehlttngyrk ipgdkcqggv npvrevkdlk
       601    kkctsnflsp ekqnsksnsv piilaivglm lvtvvagvli vkkyvcggrf lvhrysvlqq
       661    haeangvdgv daldtashtn ksgyhddsde dlle Gene ID:                X11
Gene symbol:            ATP1B1
Gene description:       sodium/potassium-transporting ATPase subunit beta-1
Unigene:                Hs.291196
Genbank:                U16799
Entrez Gene:            481
Refseq:                 NM_001677
Protein sequence (SEQ ID NO (19)):
         1    margkakeeg swkkfiwnse kkeflgrtgg swfkillfyv ifygclagif igtiqvmllt
        61    isefkptyqd rvappgltqi pqiqkteisf rpndpksyea yvlnivrfle kykdsaqrdd
       121    mifedcgdvp sepkergdfn hergerkvcr fklewlgncs glndetygyk egkpciiikl
       181    nrvlgfkpkp pknesletyp vmkynpnvlp vqctgkrded kdkvgnveyf glgnspgfpl
       241    qyypyygkll qpkylqplla vqftnltmdt eirieckayg enigysekdr fqgrfdvkie
       301    vks
```

TABLE 2-continued

```
Gene ID:            X12
Gene symbol:        AGRN
Gene description:   Agrin
Unigene:            Hs.273330
Genbank:            AB191264
Entrez Gene:        375790
Refseq:             NM_198576
Protein sequence (SEQ ID NO (20)):
         1    magrshpgpl rpllpllvva acvlpgaggt cperalerre eeanvvltgt veeilnvdpv
        61    qhtysckvrv wrylkgkdlv areslldggn kvvisgfgdp licdnqvstg dtriffvnpa
       121    ppylwpahkn elmlnsslmr itlrnleeve fcvedkpgth ftpvvpptppd acrgmlcgfg
       181    avcepnaegp grascvckks pcpsvvapvc gsdastysne celqraqcsq qrrirllsrg
       241    pcgsrdpcsn vtcsfgstca rsadgltasc lcpatcrgap egtvcgsdga dypgecqllr
       301    racarqenvf kkfdgpcdpc qgalpdpsrs crvnprtrrp emllrpescp arqapvcgdd
       361    gvtyendcvm grsgaargll lqkvrsgqcq grdqcpeper fnavclsrrg rprcscdrvt
       421    cdgayrpvca qdgrtydsdc wrqqaecrqq raipskhqgp cdqapspclg vqcafgatca
       481    vkngqaacec lqacsslydp vcgsdgvtyg saceleatac tlgreiqvar kgpcdrcgqc
       541    rfgalceaet grcvcpsecv alaqpvcgsd ghtypsecml hvhacthqis lhvasagpce
       601    tcgdavcafg avcsagqcvc prcehpppgp vcgsdgvtyg sacelreaac lqqtqieear
       661    agpceqaecg sggsgsgedg dceqelcrqr ggiwdedsed gpcvcdfscq svpgspvcgs
       721    dgvtystece lkkarcesqr glyvaaqgac rgptfaplpp vaplhcaqtp ygccqdnita
       781    argvglagcp sacqcnphgs yggtcdpatg qcscrpgvgg lrcdrcepgf wnfrgivtdg
       841    rsgctpcscd pqgavrddce qmtglcsckp gvagpkcgqc pdgralgpag ceadasapat
       901    caemrcefga rcveesgsah cvcpmltcpe anatkvcgsd gvtygnecql ktiacrqglq
       961    isiqslgpcq eavapsthpt sasvtvttpg lllsqalpap pgalplapss tahsqttppp
      1021    ssrprttasv prttvwpvlt vpptapspap slvasafges gstdgssdee lsgdqeasgg
      1081    gsgglepleg ssvatpgppv erascynsal gccsdgktps ldaegsncpa tkvfqgvlel
      1141    egvegqelfy tpemadpkse lfgetarsie stlddlfrns dvkkdfrsvr lrdlgpgksv
      1201    raivdvhfdp ttafrapdva rallrqiqvs rrrslgvrrp lqehvrfmdf dwfpafitga
      1261    tsgaiaagat arattasrlp ssavtpraph pshtsqpvak ttaapttrrp pttapsrvpg
      1321    rrppapqqpp kpcdsqpcfh ggtcqdwalg ggftcscpag rggavcekvl gapvpafegr
      1381    sflafptlra yhtlrlalef ralepqglll yngnargkdf lalallldgrv qlrfdtgsgp
      1441    avltsavpve pgqwhrlels rhwrrgtlsv dgetpvlges psgtdglnld tdlfvggvpe
      1501    dqaavalert fvgaglrgci rlldvnnqrl elgigpgaat rgsgvgcgqd hpclpnpchg
      1561    gapcqnleag rfhcqcppgr vgptcadeks pcqpnpchga apcrvlpegg aqcecplgre
      1621    gtfcqtasgq dgsgpfladf ngfshlelrg lhtfardlge kmalevvfla rgpsglllyn
      1681    gqktdgkgdf vslalrdrrl efrydlgkga avirsrepvt lgawtrvsle rngrkgalrv
      1741    gdgprvlges pvphtvlnlk eplyvggapd fsklaraaav ssgfdgaiql vslgrqllt
      1801    pehvlrqvdv tsfaghpctr asghpclnga scvpreaayv clcpggfsgp hceklvleks
      1861    agdvdtlafd grtfveylna vtesekalqs nhfelsrlte atqglvlwsg kateradyva
      1921    laivdghlql synlgsqpvv lrstvpvntn rwlrvvahre qregslqvgn eapvtgsspl
      1981    gatqldtgga lwlgglpelp vgpalpkayg tgfvgclrdv vvgrhplhll edavtkpelr
      2041    pcptp Gene ID:            X13
Gene symbol:        APP
Gene description:   Amyloid beta A4 protein
Unigene:            Hs.434980
Genbank:
                    BC065529 | AF282245 | AK298861 | AK294534 | AK295621 | AK296229 | AK297412 |
                    AK297229 | AK295373 | BC004369 | M16765 | AK311717
Entrez Gene:        351
Refseq:             NM_000484 | NM_201413 | NM_001136130 | NM_201414 | NM_001136129
Protein sequence isoform a (SEQ ID NO (21)):
         1    mlpglalll1 aawtaralev ptdgnaglla epqiamfcgr lnmhmnvqng kwdsdpsgtk
        61    tcidtkegil qycqevypel qitnvveanq pvtiqnwckr grkqckthph fvipyrclvg
       121    efvsdallvp dkckflhqer mdvcethlhw htvaketcse kstnlhdygm llpcgidkfr
       181    gvefvccpla eesdnvdsad aeeddsdvww ggadtdyadg sedkvvevae eeevaeveee
       241    eadddedded gdeveeeaee pyeeatertt siattttttt esveevvrev cseqaetgpc
       301    ramisrwyfd vtegkcapff yggcggnrnn fdteeycmav cgsamsqsll kttqeplard
       361    pvklpttaas tpdavdkyle tpgdenehah fqkakerlea khrermsqvm reweeaerqa
       421    knlpkadkka viqhfqekve sleqeaaner qqlvethmar veamlndrrr lalenyital
       481    qavpprprhv fnmlkkyvra eqkdrqhtlk hfehvrmvdp kkaaqirsqv mthlrviyer
       541    mnqslsllyn vpavaeeiqd evdellqkeq nysddvlanm iseprisygn dalmpsltet
       601    kttvellpvn gefslddlqp whsfgadsvp antenevepv darpaadrgl ttrpgsgltn
       661    ikteeisevk mdaefrhdsg yevhhqklvf faedvgsnkg aiiglmvggv viatvivitl
       721    vmlkkkqyts ihhgvvevda avtpeerhls kmqqngyenp tykffeqmqn Protein sequence isoform b (SEQ ID NO (22)):
         1    mlpglalll1 aawtaralev ptdgnaglla epqiamfcgr lnmhmnvqng kwdsdpsgtk
        61    tcidtkegil qycqevypel qitnvveanq pvtiqnwckr grkqckthph fvipyrclvg
       121    efvsdallvp dkckflhqer mdvcethlhw htvaketcse kstnlhdygm llpcgidkfr
       181    gvefvccpla eesdnvdsad aeeddsdvww ggadtdyadg sedkvvevae eeevaeveee
       241    eadddedded gdeveeeaee pyeeatertt siattttttt esveevvrev cseqaetgpc
       301    ramisrwyfd vtegkcapff yggcggnrnn fdteeycmav cgsaipttaa stpdavdkyl
       361    etpgdeneha hfqkakerle akhrermsqv mreweeaerq aknlpkadkk aviqhfqekv
       421    esleqeaane rqqlvethma rveamlndrr rlalenyita lqavpprprh vfnmlkkyvr
       481    aeqkdrqhtl khfehvrmvd pkkaaqirsq vmthlrviye rmnqslslly nvpavaeeiq
       541    devdellqke qnysddvlan miseprisyg ndalmpslte tktttvellpv ngefslddlq
       601    pwhsfgadsv pantenevep vdarpaadrg lttrpgsglt nikteeisev kmdaefrhds
```

TABLE 2-continued

```
       661     gyevhhqklv ffaedvgsnk gaiiglmvgg vviatvivit lvmlkkkqyt sihhgvvevd
       721     aavtpeerhl skmqqngyen ptykffeqmq n Protein sequence isoform f (SEQ ID NO(23)):
         1     mlpglalllll aawtaralev ypelqitnvv eanqpvtiqn wckrgrkqck thphfvipyr
        61     clvgefvsda llvpdkckfl hqermdvcet hlhwhtvake tcseskstnlh dygmllpcgi
       121     dkfrgvefvc cplaeeesdnv dsadaeedds dvwwggadtd yadgsedkvv evaeeeevae
       181     veeeeaddde ddedgdevee eaeepyeeat erttsiattt ttttesveev vrevcseqae
       241     tgperamisr wyfdvtegkc apffyggcgg nrnnfdteey cmavcgsams qsllkttqep
       301     lardpvklpt taastpdavd kyletpgden ehahfqkake rleakhrerm sqvmreweea
       361     erqaknlpka dkkaviqhfq ekvesleqea anerqqlvet hmarveamln drrrlaleny
       421     italqavppr prhvfnmlkk yvraeqkdrq htlkhfehvr mvdpkkaaqi rsqvmthlrv
       481     iyermnqsls llynvpavae eiqdevdell qkeqnysddv lanmisepri sygndalmps
       541     ltetkttvel lpvngefsld dlqpwhsfga dsvpantene vepvdarpaa drglttrpgs
       601     gltnikteei sevkmdaefr hdsgyevhhq klvffaedvg snkgaiiglm vggvviatvi
       661     vitlvmlkkk qytsihhgvv evdaavtpee rhlskmqqng yenptykffe qmqn Protein sequence isoform c (SEQ ID NO (24)):
         1     mlpglalllll aawtaralev ptdgnaglla epqiamfcgr lnmhmnvqng kwdsdpsgtk
        61     tcidtkegil qycqevypel qitnvveanq pvtiqnwckr grkqckthph fvipyrclvg
       121     efvsdallvp dkckflhqer mdvcethlhw htvaketcse kstnlhdygm llpcgidkfr
       181     gvefvccpla eesdnvdsad aeeddsdvww ggadtdyadg sedkvvevae eeevaeveee
       241     eaddddedded gdeveeeaee pyeeatertt siattttttt esveevvrvp ttaastpdav
       301     dkyletpgde nehahfqkak erleakhrer msqvmrewee aerqaknlpk adkkaviqhf
       361     qekvesleqe aanerqqlve thmarveaml ndrrrlalen yitalqavpp rprhvfnmlk
       421     kyvraeqkdr qhtlkhfehv rmvdpkkaaq irsqvmthlr viyermnqsl sllynvpava
       481     eeiqdevdel lqkeqnysdd vlanmisepr isygndalmp sltetkttve llpvngefsl
       541     ddlqpwhsfg adsvpanten evepvdarpa adrglttrpg sgltniktee isevkmdaef
       601     rhdsgyevhh qklvffaedv gsnkgaiigl mvggvviatv ivitivmlkk kqytsihhgv
       661     vevdaavtpe erhlskmqqn gyenptykff eqmqn Protein sequence isoform e (SEQ ID NO (25)):
         1     mlpglalllll aawtaralev ypelqitnvv eanqpvtiqn wckrgrkqck thphfvipyr
        61     clvgefvsda llvpdkckfl hqermdvcet hlhwhtvake tcseskstnlh dygmllpcgi
       121     dkfrgvefvc cplaeeesdnv dsadaeedds dvwwggadtd yadgsedkvv evaeeeevae
       181     veeeeaddde ddedgdevee eaeepyeeat erttsiattt ttttesveev vrvpttaast
       241     pdavdkylet pgdenehahf qkakerleak hrermsqvmr eweeaerqak nlpkadkkav
       301     iqhfqekves leqaanerq qlvethmarv eamlndrrrl alenyitalq avpprprhvf
       361     nmlkkyvrae qkdrqhtlkh fehvrmvdpk kaaqirsqvm thlrviyerm nqslsllynv
       421     pavaeeiqde vdellqkeqn ysddvlanmi seprisygnd almpsltetk ttvellpvng
       481     efslddlqpw hsfgadsvpa ntenevepvd arpaadrglt trpgsgltni kteeisevkm
       541     daefrhdsgy evhhqklvff aedvgsnkga iiglmvggvv iatvivitlv mlkkkqytsi
       601     hhgvvevdaa vtpeerhlsk mqqngyenpt ykffeqmqn Gene ID:         X14
Gene symbol:     COLEC12
Gene description: Collectin sub-family member 12
Unigene:         Hs.464422
Genbank:         AB038518
Entrez Gene:     81035
Refseq:          NM_130386
Protein sequence (SEQ ID NO (26)):
         1     mkddfaeeee vqsfgykrfg iqegtqctkc knnwalkfsi illyilcall titvailgyk
        61     vvekmdnvtg gmetsrqtyd dkltavesdl kklgdqtgkk aistnselst frsdildlrq
       121     qlreitekts knkdtleklq asgdalvdrq sqlketlenn sflittvnkt lqayngyvtn
       181     lqqdtsvlqg nlqnqmyshn vvimnlnnln ltqvqqrnli tnlqrsvddt sqaiqrikd
       241     fqnlqqvflq akkdtdwlke kvqslqtlaa nnsalakann dtledmnsql nsftgqmeni
       301     ttisqaneqn lkdlqdlhkd aenrtaikfn qleerfqlfe tdivniisni sytahhlrtl
       361     tsnlnevrtt ctdtltkhtd dltslnntla mqqdlmkrsl dtevanlsvi
       421     meemklvdsk hgqliknfti lqgppgpgrp rdgrgsqgpp gptgnkgqkg ekgepgppgp
       481     agergpigpa gppgperggkg skgsqgpkgs rgspgkpgpq gpsgdpgppg ppgkeglpgp
       541     qgppgfqglq gtvgepgvpg prglpglpgv pgmpgpkgpp gppgpsgavv plalqneptp
       601     apedngcpph wknftdkcyy fsvekeifed aklfcedkss hlvfintree qqwikkqmvg
       661     reshwigltd serenewkwl dgtspdyknw kagqpdnwgh ghgpgedcag liyagqwndf
       721     qcedvnnfic ekdretvlss al Gene ID:         X15
Gene symbol:     NCAM1
Gene description: Neural cell adhesion molecule 1
Unigene:         Hs.503878
Genbank:         BC047244
Entrez Gene:     4684
Refseq:          NM_000615 | NM_001076682 | NM_181351 | NM_001242608 l
                 NM_001242607
Protein sequence isoform 1 (SEQ ID NO (27)):
         1     mlqtkdliwt lfflgtavsl qvdivpsqge isvgeskffl cqvagdakdk diswfspnge
        61     kltpnqqris vvwnddssst ltiynanidd agiykcvvtg edgeseatv nvkifqklmf
       121     knaptpqefr egedavivcd vvsslpptii wkhkgrdvil kkdvrfivls nnylqirgik
       181     ktdegtyrce grilargein fkdiqvivnv pptiqarqni vnatanlgqs vtlvcdaegf
       241     peptmswtkd geqieqeedd ekyifsddss qltikkvdkn deayeiciae nkageqdati
```

TABLE 2-continued

```
       301    hlkvfakpki  tyvenqtame  leeqvtltce  asgdpipsit  wrtstrniss  eektldghmv
       361    vrsharvssl  tlksiqytda  geyictasnt  igqdsqsmyl  evqyapklqg  pvavytwegn
       421    qvnitcevfa  ypsatiswfr  dgqllpssny  snikiyntps  asylevtpds  endfgnynct
       481    avnrigqesl  efilvqadtp  sspsidqvep  ysstaqvqfd  epeatggvpi  lkykaewrav
       541    geevvhskwy  dakeasmegi  vtivglkpet  tyavrlaaln  gkglgeisaa  sefktqpvqg
       601    epsapklegg  mgedgnsikv  nlikqddggs  pirhylvryr  alssewkpei  rlpsgsdhvm
       661    lksldwnaey  evyvvaenqg  gkskaahfvf  rtsaqptaip  angsptsgls  tgaivgiliv
       721    ifvlllvvvd  itcyflnkcg  lfmciavnlc  gkagpgakgk  dmeegkaafs  kdeskepive
       781    vrteeeertpn  hdggkhtepn  ettpltepek  gpveakpecq  etetkpapae  vktvpndatq
       841    tkeneska Protein sequence isoform 3 (SEQ ID NO (28)):
         1    mlqtkdliwt  lfflgtavsl  qvdivpsqge  isvgeskffl  cqvagdakdk  diswfspnge
        61    kltpnqqris  vvwnddssst  ltiynanidd  agiykcvvtg  edgseseatv  nvkifqklmf
       121    knaptpqefr  egedavivcd  vvsslpptii  wkhkgrdvil  kkdvrfivls  nnylqirgik
       181    ktdegtyrce  grilargein  fkdiqvivnv  pptiqarqni  vnatanlgqs  vtlvcdaegf
       241    peptmswtkd  geqieqeedd  ekyifsddss  qltikkvdkn  deaeyiciae  nkageqdati
       301    hlkvfakpki  tyvenqtame  leeqvtltce  asgdpipsit  wrtstrniss  eektldghmv
       361    vrsharvssl  tlksiqytda  geyictasnt  igqdsqsmyl  evqyapklqg  pvavytwegn
       421    qvnitcevfa  ypsatiswfr  dgqllpssny  snikiyntps  asylevtpds  endfgnynct
       481    avnrigqesl  efilvqadtp  sspsidqvep  ysstaqvqfd  epeatggvpi  lkykaewrav
       541    geevvhskwy  dakeasmegi  vtivglkpet  tyavrlaaln  gkglgeisaa  sefktqpvhs
       601    ppppasasss  tpvplsppdt  twplpalatt  epakgepsap  klegqmgedg  nsikvnlikq
       661    ddggspirhy  lvryralsse  wkpeirlpsg  sdhvmlksld  wnaeyeyvvv  aenqqgkska
       721    ahfvfrtsaq  ptaipatlgg  nsasyffvsl  lfsavtllll  c Protein sequence isoform 2 (SEQ ID NO (29)):
         1    mlqtkdliwt  lfflgtavsl  qvdivpsqge  isvgeskffl  cqvagdakdk  diswfspnge
        61    kltpnqqris  vvwnddssst  ltiynanidd  agiykcvvtg  edgseseatv  nvkifqklmf
       121    knaptpqefr  egedavivcd  vvsslpptii  wkhkgrdvil  kkdvrfivls  nnylqirgik
       181    ktdegtyrce  grilargein  fkdiqvivnv  pptiqarqni  vnatanlgqs  vtlvcdaegf
       241    peptmswtkd  geqieqeedd  ekyifsddss  qltikkvdkn  deaeyiciae  nkageqdati
       301    hlkvfakpki  tyvenqtame  leeqvtltce  asgdpipsit  wrtstrniss  eekaswtrpe
       361    kqetldghmv  vrsharvssl  tlksiqytda  geyictasnt  igqdsqsmyl  evqyapklqg
       421    pvavytwegn  qvnitcevfa  ypsatiswfr  dgqllpssny  snikiyntps  asylevtpds
       481    endfgnynct  avnrigqesl  efilvqadtp  sspsidqvep  ysstaqvqfd  epeatggvpi
       541    lkykaewrav  geevvhskwy  dakeasmegi  vtivglkpet  tyavrlaaln  gkglgeisaa
       601    sefktqpvqg  epsapklegg  mgedgnsikv  nlikqddggs  pirhylvryr  alssewkpei
       661    rlpsgsdhvm  lksldwnaey  evyvvaenqq  gkskaahfvf  rtsaqptaip  angsptsgls
       721    tgaivgiliv  ifvlllvvvd  itcyflnkcg  lfmciavnlc  gkagpgakgk  dmeegkaafs
       781    kdeskepive  vrteeeertpn  hdggkhtepn  ettpltepek  gpveakpecq  etetkpapae
       841    vktvpndatq  tkeneska Protein sequence isoform 4 (SEQ ID NO(30)):
         1    mlqtkdliwt  lfflgtavsl  qvdivpsqge  isvgeskffl  cqvagdakdk  diswfspnge
        61    kltpnqqris  vvwnddssst  ltiynanidd  agiykcvvtg  edgseseatv  nvkifqklmf
       121    knaptpqefr  egedavivcd  vvsslpptii  wkhkgrdvil  kkdvrfivls  nnylqirgik
       181    ktdegtyrce  grilargein  fkdiqvivnv  pptiqarqni  vnatanlgqs  vtlvcdaegf
       241    peptmswtkd  geqieqeedd  ekyifsddss  qltikkvdkn  deaeyiciae  nkageqdati
       301    hlkvfakpki  tyvenqtame  leeqvtltce  asgdpipsit  wrtstrniss  eektldghmv
       361    vrsharvssl  tlksiqytda  geyictasnt  igqdsqsmyl  evqyapklqg  pvavytwegn
       421    qvnitcevfa  ypsatiswfr  dgqllpssny  snikiyntps  asylevtpds  endfgnynct
       481    avnrigqesl  efilvqadtp  sspsidqvep  ysstaqvqfd  epeatggvpi  lkykaewrav
       541    geevvhskwy  dakeasmegi  vtivglkpet  tyavrlaaln  gkglgeisaa  sefktqpvqg
       601    epsapklegg  mgedgnsikv  nlikqddggs  pirhylvryr  alssewkpei  rlpsgsdhvm
       661    lksldwnaey  evyvvaenqq  gkskaahfvf  rtsaqptaip  atlggnsasy  tfvsllfsav
       721    tllllc Protein sequence isoform 5 (SEQ ID NO (31)):
         1    mlqtkdliwt  lfflgtavsl  qvdivpsqge  isvgeskffl  cqvagdakdk  diswfspnge
        61    kltpnqqris  vvwnddssst  ltiynanidd  agiykcvvtg  edgseseatv  nvkifqklmf
       121    knaptpqefr  egedavivcd  vvsslpptii  wkhkgrdvil  kkdvrfivls  nnylqirgik
       181    ktdegtyrce  grilargein  fkdiqvivnv  pptiqarqni  vnatanlgqs  vtlvcdaegf
       241    peptmswtkd  geqieqeedd  ekyifsddss  qltikkvdkn  deaeyiciae  nkageqdati
       301    hlkvfakpki  tyvenqtame  leeqvtltce  asgdpipsit  wrtstrniss  eekaswtrpe
       361    kqevhapwnw  qvgrqkgqag  sagfpgshet  ldghmvvrsh  arvssltlks  iqytdageyi
       421    ctasntigqd  sqsmylevqy  apklqgpvav  ytwegnqvni  tcevfaypsa  tiswfrdgql
       481    lpssnysnik  iyntpsasyl  evtpdsendf  gnynctavnr  igqeslefil  vqadtpssps
       541    idqvepysst  aqvqfdepea  tggvpilkyk  aewravgeev  vhskwydake  asmegivtiv
       601    glkpettyav  rlaalngkgl  geisaasefk  tqpvqgepsa  pkleggmged  gnsikvnlik
       661    qddggspirh  ylvryralss  ewkpeirlps  gsdhvmlksl  dwnaeyevyv  vaenqqgksk
       721    aahfvfrtsa  qptaipangs  ptsglstgai  vgilivifvl  llvvvditcy  flnkcglfmc
       781    iavnlcgkag  pgakgkdmee  gkaafskdes  kepivevrte  eertpnhdgg  khtepnettp
       841    ltepekgpve  akpecqetet  kpapaevktv  pndatqtken  eska
```

TABLE 2-continued

```
Gene ID:             X16
Gene symbol:         NRP2
Gene description:    Neuropilin-2
Unigene:             Hs.471200
Genbank:             BX537423 | AF016098 | BC101525 | BC104770 |BC117413 | BC143238 | BC143608 |
                     AF022860 | AF280545 | AF280544 | AF022859 | AK290934 | AF280546 |
                     BC009222 | AL833606 | BX648292 | AK130198 | BC018631
Entrez Gene:         8828
Refseq:
                     NM_201266 | NM_003872 | NM_201279 | NM_0185341NM_201267 | NM_201264
Protein sequence isoform 1 (SEQ ID NO (32)):
        1       mdmfpltwvf lalyfsrhqv rgqpdppcgg rlnskdagyi tspgypqdyp shqncewivy
       61       apepnqkivl nfnphfeiek hdckydfiei rdgdsesadl lgkhcgniap ptiissgsml
      121       yikftsdyar qgagfslrye ifktgsedcs knftspngti espgfpekyp hnldctftil
      181       akpkmeiilq flifdlehdp lqvgegdcky dwldiwdgip hvgpligkyc gtktpselrs
      241       stgilsltfh tdmavakdgf saryylvhqe plenfqcnvp lgmesgrian eqisasstys
      301       dgrwtpqqsr lhgddngwtp nldsnkeylq vdlrfltmlt aiatqgaisr etqngyyvks
      361       yklevstnge dwmvyrhgkn hkvfqannda tevvlnklha plltrfvrir pqtwhsgial
      421       rlelfgcrvt dapcsnmlgm lsgliadsqi sasstqeylw spsaarlvss rsgwfpripq
      481       aqpgeewlqv dlgtpktvkg viiqgarggd sitavearaf vrkfkvsysl ngkdweyiqd
      541       prtqqpklfe gnmhydtpdi rrfdpipaqy vrvyperwsp agigmrlevl gcdwtdskpt
      601       vetlgptvks eetttpypte eeatecgenc sfeddkdlql psgfncndf leepcgwmyd
      661       hakwlrttwa sssspndrtf pddrnflrlq sdsqregqya rlisppvhlp rspvcmefqy
      721       qatggrgval qvvreasqes kllwviredq ggewkhgrii lpsydmeyqi vfegvigkgr
      781       sgeiaiddir litdvplenc mepisafage nfkvdipeih eregyedeid deyevdwsns
      841       ssatsgsgap stdkekswly tldpilitii amsslgvllg atcaglllyc tcsysglssr
      901       scttlenynf elydglkhkv kmnhqkccse a Protein sequence isoform 2 (SEQ ID NO (33)):
        1       mdmfpltwvf lalyfsrhqv rgqpdppcgg rlnskdagyi tspgypqdyp shqncewivy
       61       apepnqkivl nfnphfeiek hdckydfiei rdgdsesadl lgkhcgniap ptiissgsml
      121       yikftsdyar qgagfslrye ifktgsedcs knftspngti espgfpekyp hnldctftil
      181       akpkmeiilq flifdlehdp lqvgegdcky dwldiwdgip hvgpligkyc gtktpselrs
      241       stgilsltfh tdmavakdgf saryylvhqe plenfqcnvp lgmesgrian eqisasstys
      301       dgrwtpqqsr lhgddngwtp nldsnkeylq vdlrfltmlt aiatqgaisr etqngyyvks
      361       yklevstnge dwmvyrhgkn hkvfqannda tevvlnklha plltrfvrir pqtwhsgial
      421       rlelfgcrvt dapcsnmlgm lsgliadsqi sasstqeylw spsaarlvss rsgwfpripq
      481       aqpgeewlqv dlgtpktvkg viiqgarggd sitavearaf vrkfkvsysl ngkdweyiqd
      541       prtqqpklfe gnmhydtpdi rrfdpipaqy vrvyperwsp agigmrlevl gcdwtdskpt
      601       vetlgptvks eetttpypte eeatecgenc sfeddkdlql psgfncndf leepcgwmyd
      661       hakwlrttwa sssspndrtf pddrnflrlq sdsqregqya rlisppvhlp rspvcmefqy
      721       qatggrgval qvvreasqes kllwviredq ggewkhgrii lpsydmeyqi vfegvigkgr
      781       sgeiaiddir istdvplenc mepisafavd ipeiheregy edeiddeyev dwsnsssats
      841       gsgapstdke kswlytldpi litiiamssl gvllgatcag lllyctcsys glssrscttl
      901       enynfelydg lkhkvkmnhq kccsea Protein sequence isoform 3 (SEQ ID NO (34)):
        1       mdmfpltwvf lalyfsrhqv rgqpdppcgg rlnskdagyi tspgypqdyp shqncewivy
       61       apepnqkivl nfnphfeiek hdckydfiei rdgdsesadl lgkhcgniap ptiissgsml
      121       yikftsdyar qgagfslrye ifktgsedcs knftspngti espgfpekyp hnldctftil
      181       akpkmeiilq flifdlehdp lqvgegdcky dwldiwdgip hvgpligkyc gtktpselrs
      241       stgilsltfh tdmavakdgf saryylvhqe plenfqcnvp lgmesgrian eqisasstys
      301       dgrwtpqqsr lhgddngwtp nldsnkeylq vdlrfltmlt aiatqgaisr etqngyyvks
      361       yklevstnge dwmvyrhgkn hkvfqannda tevvlnklha plltrfvrir pqtwhsgial
      421       rlelfgcrvt dapcsnmlgm lsgliadsqi sasstqeylw spsaarlvss rsgwfpripq
      481       aqpgeewlqv dlgtpktvkg viiqgarggd sitavearaf vrkfkvsysl ngkdweyiqd
      541       prtqqpklfe gnmhydtpdi rrfdpipaqy vrvyperwsp agigmrlevl gcdwtdskpt
      601       vetlgptvks eetttpypte eeatecgenc sfeddkdlql psgfncndf leepcgwmyd
      661       hakwlrttwa sssspndrtf pddrnflrlq sdsqregqya rlisppvhlp rspvcmefqy
      721       qatggrgval qvvreasqes kllwviredq ggewkhgrii lpsydmeyqi vfegvigkgr
      781       sgeiaiddir istdvplenc mepisafade yevdwsnsss atsgsgapst dkekswlytl
      841       dpilitiiam sslgvllgat caglllyctc sysglssrsc ttlenynfel ydglkhkvkm
      901       nhqkccsea Protein sequence isoform 4 (SEQ ID NO (35)):
        1       mdmfpltwvf lalyfsrhqv rgqpdppcgg rlnskdagyi tspgypqdyp shqncewivy
       61       apepnqkivl nfnphfeiek hdckydfiei rdgdsesadl lgkhcgniap ptiissgsml
      121       yikftsdyar qgagfslrye ifktgsedcs knftspngti espgfpekyp hnldctftil
      181       akpkmeiilq flifdlehdp lqvgegdcky dwldiwdgip hvgpligkyc gtktpselrs
      241       stgilsltfh tdmavakdgf saryylvhqe plenfqcnvp lgmesgrian eqisasstys
      301       dgrwtpqqsr lhgddngwtp nldsnkeylq vdlrfltmlt aiatqgaisr etqngyyvks
      361       yklevstnge dwmvyrhgkn hkvfqannda tevvlnklha plltrfvrir pqtwhsgial
      421       rlelfgcrvt dapcsnmlgm lsgliadsqi sasstqeylw spsaarlvss rsgwfpripq
      481       aqpgeewlqv dlgtpktvkg viiqgarggd sitavearaf vrkfkvsysl ngkdweyiqd
      541       prtqqpklfe gnmhydtpdi rrfdpipaqy vrvyperwsp agigmrlevl gcdwtdskpt
      601       vetlgptvks eetttpypte eeatecgenc sfeddkdlql psgfncndf leepcgwmyd
```

TABLE 2-continued

```
       661    hakwlrttwa  ssspndrtf   pddrnflrlq  sdsqregqya  rlisppvhlp  rspvcmefqy
       721    qatggrgval  qvvreasqes  kllwviredq  ggewkhgrii  lpsydmeyqi  vfegvigkgr
       781    sgeiaiddir  istdvplenc  mepisafage  nfkggtllpg  teptvdtvpm  qpipaywyyv
       841    maaggavlvl  vsvalalvlh  yhrfryaakk  tdhsitykts  hytngaplav  eptltikleq
       901    drgshc Protein sequence isoform 5 (SEQ ID NO (36)):
         1    mdmfpltwvf  lalyfsrhqv  rgqpdppcgg  rlnskdagyi  tspgypqdyp  shqncewivy
        61    apepnqkivl  nfnphfeiek  hdckydfiei  rdgdsesadl  lgkhcgniap  ptiissgsml
       121    yikftsdyar  qgagfslrye  ifktgsedcs  knftspngti  espgfpekyp  hnldctftil
       181    akpkmeiilq  flifdlehdp  lqvgegdcky  dwldiwdgip  hvgpligkyc  gtktpselrs
       241    stgilsltfh  tdmavakdgf  saryylvhqe  plenfqcnvp  lgmesgrian  eqisasstys
       301    dgrwtpqqsr  lhgddngwtp  nldsnkeylq  vdlrfltmlt  aiatqgaisr  etqngyyvks
       361    yklevstnge  dwmvyrhgkn  hkvfqannda  tevvlnklha  plltrfvrir  pqtwhsgial
       421    rlelfgcrvt  dapcsnmlgm  lsgliadsqi  sasstqeylw  spsaarlvss  rsgwfpripq
       481    aqpgeewlqv  dlgtpktvkg  viiqgarggd  sitavearaf  vrkfkvsysl  ngkdweyiqd
       541    prtqqpklfe  gnmhydtpdi  rrfdpipaqy  vrvyperwsp  agigmrlevl  gcdwtdskpt
       601    vetlgptvks  eetttpypte  eeatecgenc  sfeddkdlql  psgfncnfdf  leepcgwmyd
       661    hakwlrttwa  ssspndrtf   pddrnflrlq  sdsqregqya  rlisppvhlp  rspvcmefqy
       721    qatggrgval  qvvreasqes  kllwviredq  ggewkhgrii  lpsydmeyqi  vfegvigkgr
       781    sgeiaiddir  istdvplenc  mepisafagg  tllpgteptv  dtvpmqpipa  ywyyvmaagg
       841    avlvlvsval  alvlhyhrfr  yaakktdhsi  tyktshytng  aplaveptlt  ikleqdrgsh
       901    c Protein sequence isoform 6 (SEQ ID NO (37)):
         1    mdmfpltwvf  lalyfsrhqv  rgqpdppcgg  rlnskdagyi  tspgypqdyp  shqncewivy
        61    apepnqkivl  nfnphfeiek  hdckydfiei  rdgdsesadl  lgkhcgniap  ptiissgsml
       121    yikftsdyar  qgagfslrye  ifktgsedcs  knftspngti  espgfpekyp  hnldctftil
       181    akpkmeiilq  flifdlehdp  lqvgegdcky  dwldiwdgip  hvgpligkyc  gtktpselrs
       241    stgilsltfh  tdmavakdgf  saryylvhqe  plenfqcnvp  lgmesgrian  eqisasstys
       301    dgrwtpqqsr  lhgddngwtp  nldsnkeylq  vdlrfltmlt  aiatqgaisr  etqngyyvks
       361    yklevstnge  dwmvyrhgkn  hkvfqannda  tevvlnklha  plltrfvrir  pqtwhsgial
       421    rlelfgcrvt  dapcsnmlgm  lsgliadsqi  sasstqeylw  spsaarlvss  rsgwfpripq
       481    aqpgeewlqv  dlgtpktvkg  viiqgarggd  sitavearaf  vrkfkvsysl  ngkdweyiqd
       541    prtqqpkvgc  swrpl Gene ID:              X17
Gene symbol:          PLXNA2
Gene description:     Plexin-A2
Unigene:              Hs.497626
Genbank:              BC132676
Entrez Gene:          5362
Refseq:               NM_025179
Protein sequence (SEQ ID NO (38)):
         1    meqrrpwpra  levdsrsvvl  lsvvwvllap  paagmpqfst  fhsenrdwtf  nhltvhqgtg
        61    avyvgainrv  ykltgnltiq  vahktgpeed  nkscyppliv  qpcsevltlt  nnvnklliid
       121    ysenrllacg  slyqgvckll  rlddlfilve  pshkkehyls  svnktgtmyg  vivrsegedg
       181    klfigtavdg  kqdyfptlss  rklprdpess  amldyelhsd  fvsslikips  dtlalvshfd
       241    ifyiygfasg  gfvyfltvqp  etpegvains  agdlfytsri  vrlckddpkf  hsyvslpfgc
       301    tragveyrll  qaaylakpgd  slaqafnits  qddvlfaifs  kgqkqyhhpp  ddsalcafpi
       361    rainlqiker  lqscyqgegn  lelnwllgkd  vqctkapvpi  ddnfcgldin  qplggstpve
       421    gltlyttsrd  rmtsvasyvy  ngysvvfvgt  ksgklkkira  dgpphggvqy  emvsylkdgs
       481    pilrdmafsi  dqrylyvmse  rqvtrvpves  ceqyttcgec  lssgdphcgw  calhnmcsrr
       541    dkcqqawepn  rfaasisqcv  slavhpssis  vsehsrllsl  vvsdapdlsa  giacafgnlt
       601    eveggqvsgsq  vicispgpkd  vpvipldqgw  fglelqlrsk  etgkifvste  fkfyncsahq
       661    lclscvnsaf  rchwckyrnl  cthdpttcsf  qegrinised  cpqlvpteei  lipvgevkpi
       721    tlkarnlpqp  qsgqrgyecv  lniqgaihrv  palrfnsssv  qcqnssyqyd  gmdisnlavd
       781    favvwngnfi  idnpqdlkvh  lykcaagres  cglclkadrk  fecgwcsger  rctlhqhcts
       841    psspwldwss  hnvkcsnpqi  teiltvsgpp  eggtrvtihg  vnlgldfsei  ahhvqvagvp
       901    ctplpgeyii  aeqivcemgh  alvgttsgpv  rlcigeckpe  fmtkshqqyt  fvnpsvlsln
       961    pirgpesggt  mvtitghylg  agssvavylg  nqtcefygrs  mseivcvspp  ssnglgpvpv
      1021    sysvdrahvd  snlqfeyidd  prvqriepew  siasghtplt  itgfnldviq  eprirvkfng
      1081    kesvnyckvv  ntttltclap  sltttdyrpgl  dtverpdefg  fvfnnvqsll  iyndtkfiyy
      1141    pnptfellsp  tgvldqkpgs  piilkgknlc  ppasggakln  ytvligetpc  avtvsetqll
      1201    ceppnitgqh  kvmvhvggmv  fspgsysvis  dsllltplaiv  siaaggslll  iiviivliay
      1261    krksrendlt  lkrlqmqmdn  lesrvaleck  eafaelqtni  neltsdldrs  gipylydyrty
      1321    amrvlfpgie  dhpvlrelev  qgngqhvek   alklfaqlin  nkvflltfir  tlelqrsfsm
      1381    rdrgnvasli  mtglqgrley  atdvlkqlls  dlidknlenk  nhpklllrrt  esvaekmltn
      1441    wfaflllhkfl  kecageplfm  lycaikqqme  kgpidaitge  aryslsedkl  irqqieyktl
      1501    ilncvnpdne  nspeipvkvl  ncdtitqvke  kildavyknv  pysqrpravd  mdlewrqgri
      1561    arvvlqdedi  ttkiegdwkr  lntlmhyqvs  drsvvalvpk  qtssynipas  asisrtsisr
      1621    ydssfrytgs  pdslrsrapm  itpdlesgvk  vwhlvknhdh  gdqkegdrgs  kmvseiyltr
      1681    llatkgtlqk  fvddlfetlf  stvhrgsalp  laikymfdfl  deqadrhsih  dtdvrhtwks
      1741    nclplrfwvn  viknpqfvfd  ihkgsitdac  lsvvaqtfmd  scstsehrlg  kdspsnklly
      1801    akdipsyksw  veryyadiak  lpaisdqdmn  aylaeqsrlh  avefnmlsal  neiysyvsky
      1861    seeligaleq  deqarrqrla  ykveqlinam  sies
```

TABLE 2-continued

```
Gene ID:            X18
Gene symbol:        PCDHA4
Gene description:   Protocadherin alpha-4
Unigene:            Hs.199343
Genbank:            AF152482 | AF152312
Entrez Gene:        56144
Refseq:             NM_0189071 NM_031500
Protein sequence isoform 1 (SEQ ID NO (39)):
         1  mefswgsgqe srrllllll laaweagngq lhysyseeak hgtfvgriaq dlglelaelv
        61  prlfrvaskg rggllevnlq ngilfvnsri dreelcrrsa ecsihleviv drplqvfhvd
       121  vevrdindnp pvfpatqknl siaesrplds rfplegasda digenallty rlspneyfsl
       181  ekppddelvk glglilrksl dreeapeifl vltatdggkp eltgtvqlli tvldandnap
       241  afdrtiykvr llenvpngtl viklnasdld eglngdivys fsndispnvk skfhidpitg
       301  qiivkgyidf eesksyeiiv egidkgqlpl sghcrvivev ednndnvpdl efkslslpir
       361  edaplgtvia lisvsdkdmg vnglvtcslt shvpfklyst fknyyslvld saldresysa
       421  yelvvtardg gspslwatas vsvevadvnd napafaqpey tvfvkennpp gchiftvsaw
       481  dadaqenalv syslverrvg eralssyvsv haesgkvyal qpldheelel lqfqvtarda
       541  gvpplgsnvt lqvfvldend napallapra ggtggavsel vpwsvgvghv vakvravdad
       601  sgynawlsye lqpgtggari pfrvglytge isttraldet daprhrllvl vkdhgepalt
       661  atatvlvslv esgqapkass ralvgavgpd aalvdvnvyl iiaicavssl lvltllllyta
       721  lrcsalpteg acapgkptlv cssavgswsy sqqrrprvcs gegppktdlm afspslpdsr
       781  dredqlqtte esfakprqpn pdwrysaslr agmhssvhle eagilragpg gpdqqwptvs
       841  satpepeage vsppvgagvn snswtfkygp gnpkgsgpge lpdkfiipgs paiisirqep
       901  tnsqidksdf itfgkkeetk kkkkkkgnk tqekkekgns ttdnsdq Protein sequence isoform 2 (SEQ ID NO (40)):
         1  mefswgsgqe srrllllll laaweagngq lhysvseeak hgtfvgriaq dlglelaelv
        61  prlfrvaskg rggllevnlq ngilfvnsri dreelcrrsa ecsihleviv drplqvfhvd
       121  vevrdindnp pvfpatqknl siaesrplds rfplegasda digenallty rlspneyfsl
       181  ekppddelvk glglilrksl dreeapeifl vltatdggkp eltgtvqlli tvldandnap
       241  afdrtiykvr llenvpngtl viklnasdld eglngdivys fsndispnvk skfhidpitg
       301  qiivkgyidf eesksyeiiv egidkgqlpl sghcrvivev ednndnvpdl efkslslpir
       361  edaplgtvia lisysdkdmg vnglvtcslt shvpfklvst fknyyslvld saldresysa
       421  yelvvtardg gspslwatas vsvevadvnd napafaqpey tvfvkennpp gchiftvsaw
       481  dadaqenalv syslverrvg eralssyvsv haesgkvyal qpldheelel lqfqvtarda
       541  gvpplgsnvt lqvfvldend napallapra ggtggavsel vpwsvgvghv vakvravdad
       601  sgynawlsye lqpgtggari pfrvglytge isttraldet daprhrllvl vkdhgepalt
       661  atatvlvslv esgqapkass ralvgavgpd aalvdvnvyl iiaicavssl lvltllllyta
       721  lrcsalpteg acapgkptlv cssavgswsy sqqrrprvcs gegppktdlm afspslpdsr
       781  dredqlqtte esfakvsv Gene ID:            X19
Gene symbol:        PCDHAC2
Gene description:   Protocadherin alpha-C2
Unigene:            Hs.199343
Genbank:            AF152304
Entrez Gene:        56134
Refseq:             NM_018899 | NM_031883
Protein sequence isoform 1 (SEQ ID NO (41)):
         1  meqagtrpaa tehprlrrpm pwllllplll lllllllpgpa asqlrysvpe eqapgalvgn
        61  varalglelr rlgpgclrin hlgapspryl eldltsgalf vneridreal ceqrprells
       121  levlahnpva vsaveveild indnsprfpr pnyqlqvses vapgarfhie saqdpdvgan
       181  svqtyelsps ehfeldlkpl genskvlelv lrkgldreqa alhhlvltav dggiparsgt
       241  aqisvrvldt ndnspafdqs tyrvqlreds erryslssyt
       301  sdrerqlfsi dastgevrvi ggldyeeass yqiyvqatdr gpvpmaghck vlvdivdvnd
       361  napevvltdl yspvpenatp ntiavlsvn dqdsgpnrkv slgleatlpf rlngfgnsyt
       421  lvvsgpldre rvavynitvt atdggipqlt slrtlkveis dindnppsfl edsysiyiqe
       481  nnlpgvllct vqatdpdeke naevtyslle reiqglpvts yvsinsasgs lyavnsfdye
       541  kfreffvctve aqdkgsppls stvtanvyvv dmndhaphil yptstnssaa femvprtapa
       601  gylvtkviam dsdsgqnawl fyhlaqtsdl dlfkvelhtg eirttrkmgd esgstfnitv
       661  vvrdngepsl sasvaitvav vdrvskilpd tqrhyksprt yseitlylii alstvsfifl
       721  ltiiilsiik cyrytaygta ccggfcgvre rspaelykqa nnnidariph glkvqphfie
       781  vrgngsltkt ycykacltag sgsdtfmfyn tgaqtgpgps gaqaavtdsr nltggsqna
       841  gnliilknea vsqneprqpn pdwrysaslr agmhssvhle eagilragpg gpdqqwptvs
       901  satpepeage vsppvgagvn snswtfkygp gnpkgsgpge lpdkfiipgs paiisirqep
       961  tnsqidksdf itfgkkeetk kkkkkkgnk tqekkekgns ttdnsdq Protein sequence isoform 2 (SEQ ID NO (42)):
         1  meqagtrpaa tehprlrrpm pwllllplll lllllllpgpa asqlrysvpe eqapgalvgn
        61  varalglelr rlgpgclrin hlgapspryl eldltsgalf vneridreal ceqrprclls
       121  levlahnpva vsaveveild indnsprfpr pnyqlqvses vapgarfhie saqdpdvgan
       181  svqtyelsps ehfeldlkpl qenskvlelv lrkgldreqa alhhlvltav dggiparsgt
       241  aqisvrvldt ndnspafdqs tyrvqlreds ppgtlvvkln asdpdegsng elryslssyt
       301  sdrerqlfsi dastgevrvi ggldyeeass yqiyvqatdr gpvpmaghck vlvdivdvnd
       361  napevvltdl yspvpenatp ntiavlsvn dqdsgpnrkv slgleatlpf rlngfgnsyt
       421  lvvsgpldre rvavynitvt atdggipqlt slrtlkveis dindnppsfl edsysiyiqe
       481  nnlpgvllct vqatdpdeke naevtyslle reiqglpvts yvsinsasgs lyavnsfdye
       541  kfreffvctve aqdkgsppls stvtanvyvv dmndhaphil yptstnssaa femvprtapa
       601  gylvtkviam dsdsgqnawl fyhlaqtsdl dlfkvelhtg eirttrkmgd esgstfnitv
       661  vvrdngepsl sasvaitvav vdrvskilpd tqrhyksprt yseitlylii alstvsfifl
```

TABLE 2-continued

```
       721    ltiiilsiik cyrytaygta ccggfcgvre rspaelykqa nnnidariph glkvqphfie
       781    vrgngsltkt ycykacltag sgsdtfmfyn tgaqtgpgps gaqaavtdsr nitgqsgqna
       841    gnliilknea vsqnevrqws ggllqthafv thppiscdla llsh Gene ID:            X20
Gene symbol:        GPC4
Gene description:   Glypican 4
Unigene:            Hs.58367
Genbank:            AF030186
Entrez Gene:        2239
Refseq:             NM_001448
Protein sequence (SEQ ID NO (43)):
         1    mrllwklvil lplinssagd gllsrpiftq ephdvifpld lsksevilnc aangypsphy
        61    rwkqngtdid ftmsyhyrld ggslainsph tdqdigmyqc latnllgtil srkaklqfay
       121    iedfetktrs tvsvregqgv vllcgppphf gdlsyawtfn dnplyvqedn rrfvsqetgn
       181    lyiakvepsd vgnytcfitn keaqrsvqgp ptplvqrtdg vmgeyepkie vrfpetiqaa
       241    kdssvklecf algnpvpdis wrrldgsplp gkvkysksqa ileipnfqqe degfyecias
       301    nlrgrnlakg qlifyappew eqkiqnthls iydnllweck asgkpnpwyt wlkngerlnp
       361    eeriqiengt liitmlnvsd sgvyqcaaen kyqiiyanae lrvlasapdf skspvkkksf
       421    vqvggdivig ckpnafpraa iswkrgtetl rqskriflle dgsikiynit rsdagsytci
       481    atnqfgtakn tgslivkert vitvppskmd vtvgesivlp cqvshdpsie vvfvwffngd
       541    vidlkkgvah feriggesvg dlmirniqlh hsgkylctvq ttleslsava diivrgppgp
       601    pedvqvedis sttsqlswra gpdnnspiqi ftiqtrtpfs vgwqavatvp eilngktyna
       661    tvvglspwve yefrvvagns igigepseps ellrtkasvp vvapvnihgg ggsrselvit
       721    wesipeelqn gegfgyiimf rpvgsttwsk ekvssvessr fvyrnesiip lspfevkvgv
       781    ynnegegsls tvtivysged epqlaprgts lqsfsaseme vswnaiawnr ntgrvlgyev
       841    lywtddskes migkirvsgn vttknitglk antiyfasvr ayntagtgps sppvnvttkk
       901    sppsqppani awkltnsklc lnwehvktme nesevlgyki lyrqnrqskt hiletnntsa
       961    ellvpfeedy lieirtvsdg gdgssseeir ipkmsslssr giqflepsth flsivivifh
      1021    cfaiqpli Gene ID:            X21
Gene symbol:        CNTN6
Gene description:   Contactin 6
Unigene:            Hs.387300
Genbank:            AB003592
Entrez Gene:        27255
Refseq:             NM_014461
Protein sequence (SEQ ID NO (44)):
         1    marfglpall ctlavlsaal laaelksksc sevrrlyvsk gfnkndaplh eingdhlkic
        61    pqgstccsqe meekyslqsk ddfksvvseq cnhlqavfas rykkfdeffk ellenaeksl
       121    ndmfvktygh lymqnselfk dlfwarlle yy vvgnvnleem lndfwarlle rmfrlvnsge
       181    hftdeylecv skyteqlkpf gdvprklklq vtrafvaart faqglavagd vvsksvsvnp
       241    taqcthallk miycshcrgl vtvkpcynyc snimrgclan qqdldfewnn fidamlmvae
       301    rlegpfnies vmdpidvkis daimnmqdns vqvsqkvfqg cgppkplpag risrsisesa
       361    fsarfrphhp eerpttaagt sldrlvtdvk eklkqakkfw sslpsnvcnd ermaagngne
       421    ddcwngkgks rylfavtgng lanqgnnpev qvdtskpdil ilrqimalrv mtskmknayn
       481    gndvdffdis dessgegsgs gceyqqcpse fdynatdhag ksanekadsa gvrpgaqayl
       541    ltvfcilflv mqrewr Gene ID:            X22
Gene symbol:        SLC9A7
Gene description:   solute carrier family 9 (sodium/hydrogen exchanger), member 7
Unigene:            Hs.496057
Genbank:            AF298591
Entrez Gene:        84679
Refseq:             NM_001257291 | NM_032591
Protein sequence isoform 1 (SEQ ID NO (45)):
         1    mepgdaarpg sgratgappp rllllplllg wglrvaaaas asssgaaaed ssameelate
        61    keaeeshrqd sysllltfill ltltiltiwl fkhrrvrflh etglamiygl ivgvilrygt
       121    patsgrdksl sctqedrafs tllvnvsgkf feytlkgeis pgkinsveqn dmlrkvtfdp
       181    evffnillpp iifhagyslk krhffrnlgs ilayaflgta vscfiignlm ygvvklmkim
       241    gqlsdkfyyt dclffgaiis atdpvtvlai fnelhadvdl yallfgesvl ndavaivlss
       301    sivayqpagl nthafdaaaf fksvgiflgi fsgsftmgav tgvvtalvtk ftklhcfpll
       361    etalfflmsw stfllaeacg ftgvvavlfc gitqahytyn nlsvesrsrt kqlfevlhfl
       421    aenfifsymg lalftfqkhv fspifiigaf vaiflgraah iyplsfflnl grrhkigwnf
       481    qhmmmfsglr gamafalair dtasyarqmm fttttllivff twwiigggtt pmlswlnirv
       541    gveepseedq nehhwqyfrv gvdpdqdppp nndsfqvlqg dgpdsargnr tkqesawifr
       601    lwysfdhnyl kpilthsgpp ltttlpawcg llarcltspq vydnqeplre edssfilteg
       661    dltltygdst vtangssssh tastslegsr rtkssseevl erdlgmgdqk vssrgtrlvf
       721    pledna Protein sequence isoform 2 (SEQ ID NO (46)):
         1    mepgdaarpg sgratgappp rllllplllg wglrvaaaas asssgaaaed ssameelate
        61    keaeeshrqd sysllltfill ltltiltiwl fkhrrvrflh etglamiygl ivgvilrygt
       121    patsgrdksl sctqedrafs tllvnvsgkf feytlkgeis pgkinsveqn dmlrkvtfdp
       181    evffnillpp iifhagyslk krhffrnlgs ilayaflgta vscffignlm ygvvklmkim
       241    gqlsdkfyyt dclffgaiis atdpvtvlai fnelhadvdl yallfgesvl ndavaivlss
       301    sivayqpagl nthafdaaaf fksvgiflgi fsgsftmgav tgvnanvtkf tklhcfplle
       361    talffflmsws tfllaeacgf tgvvavlfcg itqahytynn lsvesrsrtk qlfevlhfla
```

TABLE 2-continued

```
       421  enifsymgl alftfqkhvf spifiigafv aiflgraahi yplsfflnlg rrhkigwnfq
       481  hmmmfsglrg amafalaird tasyarqmmf tttlliivfft vwiigggttp mlswlnirvg
       541  veepseedqn ehhwqyfrvg vdpdqdpppn ndsfqvlqgd gpdsargnrt kqesawifrl
       601  wysfdhnylk pilthsgppl tttlpawcgl larcltspqv ydnqeplree dsdfiltegd
       661  ltltygdstv tangsssht astslegsrr tkssseevle rdlgmgdqkv ssrgtrlvfp
       721  ledna Gene ID:           X23
Gene symbol:       PVRL3
Gene description:  poliovirus receptor-related 3
Unigene:           Hs.293917
Genbank:           AK075105
Entrez Gene:       25945
Refseq:            NM_015480 | NM_001243286 | NM_001243288
Protein sequence isoform 1 (SEQ ID NO (47)):
         1  martlrpspl cpgggkaqls sasllgagll lqpptpppll lllfplllfs rlcgalagpi
        61  ivephvtavw gknvslkcli evnetitqis wekihgkssq tvavhhpqyg fsvqgeyqgr
       121  vlfknyslnd atitlhnigf sdsgkyicka vtfplgnaqs sttvtvlvep tvslikgpds
       181  lidggnetva aiciaatgkp vahidwegdl gemestttsf pnetatiisq yklfptrfar
       241  grritcvvkh palekdirys fildiqyape vsvtgydgnw fvgrkgvnlk cnadanpppf
       301  ksvwsrldgq wpdgllasdn tlhfvhpltf nysgvyickv tnslgqrsdq kviyisdppt
       361  tttlqptiqw hpstadiedl atepkklpfp lstlatikdd tiatiiasvv ggalfivlvs
       421  vlagifcyrr rrtfrgdyfa knyippsdmq kesqidvlqq deldsypdsv kkenknpvnn
       481  lirkdyleep ektqwnnven lnrferpmdy yedlkmgmkf vsdehydene ddlvshvdgs
       541  visrrewyv Protein sequence isoform 2 (SEQ ID NO (48)):
         1  martlrpspl cpgggkaqls sasllgagll lqpptpppll lllfplllfs rlcgalagpi
        61  ivephvtavw gknvslkcli evnetitqis wekihgkssq tvavhhpqyg fsvqgeyqgr
       121  vlfknyslnd atitlhnigf sdsgkyicka vtfplgnaqs sttvtvlvep tvslikgpds
       181  lidggnetva aiciaatgkp vahidwegdl gemestttsf pnetatiisq yklfptrfar
       241  grritcvvkh palekdirys fildiqyape vsvtgydgnw fvgrkgvnik cnadanpppf
       301  ksvwsrldgq wpdgilasdn tlhfvhpltf nysgvyickv tnslgqrsdq kviyisayns
       361  vaslnc Protein sequence isoform 3 (SEQ ID NO (49)):
         1  maegwrwcfv rrtpgllrgp llprsfsgnp ralagpiive phvtavwgkn vslkclievn
        61  etitqiswek ihgkssqtva vhhpqygfsv qgeyqgrvlf knyslndati tlhnigfsds
       121  gkyickavtf plgnaqsstt vtvlveptvs likgpdslid ggnetvaaic iaatgkpvah
       181  idwegdlgem estttsfpne tatiisqykl fptrfargrr itcvvkhpal ekdirysfil
       241  diqyapevsv tgydgnwfvg rkgvnlkcna danpppfksv wsrldgqwpd gllasdntlh
       301  fvhpltfnys gvyickvtns lgqrsdqkvi yisdvpfkqt ssiavagavi gavlalfiia
       361  ifvtvlltpr kkrpsyldkv idlppthkpp plyeersppl pqkdlfqpeh lplqtqfker
       421  evgnlqhsng lnsrsfdyed enpvgedgiq qmyplynqmc yqdrspgkhh qnndpkrvyi
       481  dprehyv Gene ID:           X24
Gene symbol:       SLC4A4
Gene description:  solute carrier family 4, sodium bicarbonate cotransporter, member 4
Unigene:           Hs.5462
Genbank:           AF011390
Entrez Gene:       8671
Refseq:            NM_001098484 | NM_001134742 | NM_003759
Protein sequence isoform 1 (SEQ ID NO (50)):
         1  medeavldrg asflkhvcde eeveghhtiy igvhvpksyr rrrrhkrktg hkekkekeri
        61  senysdksdi enadesssi lkplispaae rirfilgeed dspappqlft eldellavdg
       121  qemewketar wikfeekveq ggerwskphv atlslhslfe lrtcmekgsi mldreasslp
       181  qlvemivdhq ietgllkpel kdkvtytllr khrhqtkksn lrsladigkt vssasrmftn
       241  pdngspamth rnltssslnd isdkpekdql knkfmkklpr daeasnvlvg evdfldtpfi
       301  afvrlqqavm lgaltevpvp trfifillgp kgkaksyhei graiatlmsd evfhdiayka
       361  kdrhdliagi defldevivl ppgewdpair ieppkslpss dkrknmysgg envqmngdtp
       421  hdgghgggh gdceelqrtg rfcgglikdi krkapffasd fydalniqal sailfiylat
       481  vtnaitfggl lgdatdnmqg vlesflgtav sgaifclfag qpltilsstg pvlvferlif
       541  nfskdnnfdy lefriwiglw saficlilva tdasflvqyf trfteegfss lisfifiyda
       601  fkkmiklady ypinsnfkvg yntlfsctcv ppdpanisis ndttlapeyl ptmsstdmyh
       661  nttfdwafls kkecskyggn lvgnnenfvp ditlmsfilf lgtytssmal kkfktspyfp
       721  ttarklisdf aiilsilifc vidalvgvdt pklivpsefk ptspnrgwfv ppfgenpwwv
       781  claaaipall vtilifmdqq itavivnrke hklkkgagyh ldlfwvailm vicslmalpw
       841  yvaatvisia hidslkmete tsapgeqpkf lgvreqrvtg tlvfiltgls vfmapilkfi
       901  pmpvlygvfl ymgvaslngv qfmdrlklll mplkhqpdfi ylrhyplrrv hlftflqvlc
       961  lallwilkst vaaiifpvmi lalvavrkgm dylfsqhdls flddvipekd kkkkedekkk
      1021  kkkkgsldsd nddsdcpyse kvpsikipmd imeqqpflsd skpsdrersp tflerhtsc Protein sequence isoform 3 (SEQ ID NO (51)):
         1  medeavldrg asflkhvcde eeveghhtiy igvhvpksyr rrrrhkrktg hkekkekeri
        61  senysdksdi enadesssi lkplispaae rirfilgeed dspappqlft eldellavdg
       121  qemewketar wikfeekveq ggerwskphv atlslhslfe lrtcmekgsi mldreasslp
       181  qlvemivdhq ietgllkpel kdkvtytllr khrhqtkksn lrsladigkt vssasrmftn
       241  pdngspamth rnltssslnd isdkpekdql knkfmkklpr daeasnvlvg evdfldtpfi
       301  afvrlqqavm lgaltevpvp trflfillgp kgkaksyhei graiatlmsd evfhdiayka
```

TABLE 2-continued

```
     361    kdrhdliagi defidevivi ppgewdpair ieppkslpss dkrknmysgg envqmngdtp
     421    hdgghggggh gdceelqrtg rfcgglikdi krkapffasd fydalniqal sailfiylat
     481    vtnaitfggl lgdatdnmqg vlesflgtav sgaifclfag qpltilsstg pvlvferllf
     541    nfskdnnfdy lefrlwiglw saflclilva tdasflvqyf trfteegfss lisfifiyda
     601    fkkmiklady ypinsnfkvg yntlfsctcv ppdpanisis ndttlapeyl ptmsstdmyh
     661    nttfdwafls kkecskyggn lvgnnenfvp ditlmsfilf lgtytssmal kkfktspyfp
     721    ttarklisdf aiilsilifc vidalvgvdt pklivpsefk ptspnrgwfv ppfgenpwwv
     781    claaaipall vtilifmdqq itavivnrke hklkkgagyh ldlfwvailm vicslmalpw
     841    yvaatvisia hidslkmete tsapgeqpkf lgvreqrvtg tlvfiltgls vfmapilkfi
     901    pmpvlygvfl ymgvaslngv qfmdrlklll mplkhqpdfi ylrhyplrrn hlftflqvlc
     961    lallwilkst vaaiifpvmi lalvavrkgm dylfsqhdls flddvipekd kkkkedekkk
    1021    kkkkgsldsd nddekdhqhs lnathhadki pflqsigmps pprtpvkvvp qirieleped
    1081    ndyfwrskgt ettl
```

Protein sequence isoform 2 (SEQ ID NO (52)):

```
       1    mstenvegkp snlgergrar sstflrvvqp mfnhsiftsa vspaaerirf ilgeeddspa
      61    ppqlftelde llavdgqeme wketarwikf eekveqgger wskphvatls lhslfelrtc
     121    mekgsimldr easslpqlve mivdhqietg llkpelkdkv tytllrkhrh qtkksnlrsl
     181    adigktvssa srmftnpdng spamthrnlt ssslndisdk pekdqlknkf mkklprdaea
     241    snvlvgevdf ldtpfiafvr lqqavmlgal tevpvptrfl fillgpkgka ksyheigrai
     301    atlmsdevfh diaykakdrh dliagidefl devivlppge wdpairiepp kslpssdkrk
     361    nmysggenvq mngdtphdgg hgggghgdce elqrtgrfcg glikdikrka pffasdfyda
     421    lniqalsail fiylatvtna itfggllgda tdnmqgvles flgtaysgai fclfagqplt
     481    ilsstgpvlv ferllfnfsk dnnfdylefr lwiglwsafl clilvatdas flvqyftrft
     541    eegfsslisf ifiydafkkm ikladyypin snfkvgyntl fsctcvppdp anisisndtt
     601    lapeyiptms stdmyhnttf dwaflskkec skyggnlvgn nenfvpditl msfilflgty
     661    tssmalkkfk tspyfpttar klisdfaiil silifcvida lvgvdtpkli vpsefkptsp
     721    nrgwfvppfg enpwwvclaa aipallvtil ifmdqqitav ivnrkehklk gagyhldlf
     781    wvailmvics lmalpwyvaa tvisiahids lkmetetsap geqpkflgvr eqrvtgtlvf
     841    iltglsvfma pilkfipmpv lygvflymgv aslngvqfmd rlklllmplk hqpdfiylrh
     901    vplrrvhlft flqvlclall wilkstvaai ifpvmilalv avrkgmdylf sqhdlsfldd
     961    vipekdkkkk edekkkkkkk gsldsdndds dcpysekvps ikipmdimeq qpflsdskps
    1021    drersptfle rhtsc
```

Gene ID:            X25
Gene symbol:        CXADR
Gene description:   coxsackie virus and adenovirus receptor
Unigene:            Hs.634837
Genbank:            AY072912 | AY072911 | AY072910 | AK313526 |
Entrez Gene:        1525
Refseq:             NM_001338 | NM_001207063 | NM_001207064 | NM_001207065 |
                    NM_001207066

Protein sequence isoform 1 (SEQ ID NO (53)):

```
       1    malllcfvll cgvvdfarsl sittpeemie kakgetaylp ckftlspedq gpldiewlis
      61    padnqkvdqv iilysgdkiy ddyypdlkgr vhftsndlks gdasinvtnl qlsdigtyqc
     121    kvkkapgvan kkihvvlvk psgarcyvdg seeigsdfki kcepkegslp lqyewqklsd
     181    sqkmptswla emtssvisvk nasseysgty sctvrnrvgs dqcllrlnvv ppsnkaglia
     241    gaiigtllal aligliifcc rkrreekye kevhhdired vpppksrtst arsyigsnhs
     301    slgsmspsnm egyskqtynq vpsedfertp qsptlppakv aapnlsrmga ipvmipaqsk
     361    dgsiv
```

Protein sequence isoform 2 (SEQ ID NO (54)):

```
       1    malllcfvll cgvvdfarsl sittpeemie kakgetaylp ckftlspedq gpldiewlis
      61    padnqkvdqv iilysgdkiy ddyypdlkgr vhftsndlks gdasinvtnl qlsdigtyqc
     121    kvkkapgvan kkihvvlvk psgarcyvdg seeigsdfki kcepkegslp lqyewqklsd
     181    sqkmptswla gkmchlqrav rplpeatsav iihpwgpcll ptwkdiprls itkyqvktln
     241    allrvrlshl lr
```

Protein sequence isoform 3 (SEQ ID NO(55)):

```
       1    malllcfvll cgvvdfarsl sittpeemie kakgetaylp ckftlspedq gpldiewlis
      61    padnqkvdqv iilysgdkiy ddyypdlkgr vhftsndlks gdasinvtnl qlsdigtyqc
     121    kvkkapgvan kkihvvlgk mchlqravrp lpeatsavii hpwgpcllpt wkdiprlsit
     181    kyqvktlnal lrvrlshllr
```

Protein sequence isoform 4 (SEQ ID NO (56)):

```
       1    malllcfvll cgnndfarsl sittpeemie kakgetaylp ckftlspedq gpldiewlis
      61    padnqkvdqv grcatskepy vhcqklhrq
```

Protein sequence isoform 5 (SEQ ID NO(57)):

```
       1    malllcfvll cgvvdfarsl sittpeemie kakgetaylp ckftlspedq gpldiewlis
      61    padnqkvdqv iilysgdkiy ddyypdlkgr vhftsndlks gdasinvtnl qlsdigtyqc
     121    kvkkapgvan kkihvvlvk psgarcyvdg seeigsdfki kcepkegslp lqyewqklsd
     181    sqkmptswla emtssvisvk nasseysgty sctvrnrvgs dqcllrlnvv ppsnkaglia
     241    gaiigtllal aligliifcc rkrreekye kevhhdired vpppksrtst arsyigsnhs
     301    slgsmspsnm egyskqtynq vpsedfertp qsptlppakf kypyktdgit vv
```

TABLE 2-continued

```
Gene ID:          X26
Gene symbol:      CADM4
Gene description: cell adhesion molecule 4
Unigene:          Hs.370984
Genbank:          AF363368
Entrez Gene:      199731
Refseq:           NM_145296
Protein sequence (SEQ ID NO (58)):
       1   mgrarrfqwp llllwaaaag pgagqevqte nvtvaeggva eitcrlhqyd gsivviqnpa
      61   rqtlffngtr alkderfqle efsprrvrir lsdarledeg gyfcqlyted thhqiatltv
     121   lvapenpvve vreqavegge velsclvprs rpaatlrwyr drkelkgvss sqengkvwsv
     181   astvrfrvdr kddggiiice aqnqalpsgh skqtqyvldv qysptariha sqavvregdt
     241   lvltcavtgn prpnqirwnr gneslperae avgetltlpg lvsadngtyt ceasnkhgha
     301   ralyvlvvyd pgavveaqts vpyaivggil allvfliicv lvgmvwcsvr qkgsylthea
     361   sgldeqgear eaflngsdgh krkeeffi Gene ID:          Y1
Gene symbol:      CLCA2
Gene description: chloride channel accessory 2
Unigene:          Hs.241551
Genbank:          BC041096
Entrez Gene:      9635
Refseq:           NM_006536
Protein sequence (SEQ ID NO (59)):
       1   mtqrsiagpi cnlkfvtllv alsselpflg agvqlqdngy nglliainpq vpenqnlisn
      61   ikemiteasf ylfnatkrrv ffrnikilip atwkannnsk ikqesyekan vivtdwygah
     121   gddpytlqyr gcgkegkyih ftpnfllndn ltagygsrgr vfvhewahlr wgvfdeynnd
     181   kpfyinggnq ikvtrcssdi tgifvcekgp cpqenciisk lfkegctfiy nstqnatasi
     241   mfmqslssvv efcnasthnq eapnlqnqmc slrsawdvit dsadfhhsfp mngtelpppp
     301   tfslvqagdk vvclvldvss kmaeadrllq lqqaaefylm qiveihtfvg iasfdskgei
     361   raqlhqinsn ddrkllvsyl pttvsaktdi sicsglkkgf evveklngka ygsvmilvts
     421   gddkllgncl ptvlssgsti hsialgssaa pnleelsrlt gglkffvpdi snsnsmidaf
     481   srissgtgdi fqqhiqlest genvkphhql kntvtvdntv gndtmflvtw qasgppeiil
     541   fdpdgrkyyt nnfitnitfr taslwipgta kpghwtytln nthhslqalk vtvtsrasns
     601   avppatveaf verdslhfph pvmiyanvkq gfypilnatv tatvepetgd pvtlrllddg
     661   agadvikndg iysryffsfa angryslkvh vnhspsistp ahsipgsham yvpgytangn
     721   iqmnaprksv grneeerkwg fsrvssggsf svlgvpagph pdvfppckii dleavkveee
     781   ltlswtapge dfdqgqatsy eirmsksqln iqddfnnail vntskrnpqq agireififs
     841   pqistngpeh qpngethesh riyvairamd rnslqsaysn iaqaplfipp nsdpvpardy
     901   lilkgvltam gligiiclii wthhtlsrk kradkkengt kll Gene ID:          Y2
Gene symbol:      ECM1
Gene description: extracellular matrix protein 1
Unigene:          Hs.81071
Genbank:          U68187 | U68186 | AK097046
Entrez Gene:      1893
Refseq:           NM_004425 | NM_022664 | NM_001202858
Protein sequence isoform 1 (SEQ ID NO (60)):
       1   mgttaraalv ltylavasaa seggftatgq rqlrpehfqe vgyaappspp lsrslpmdhp
      61   dssqhgppfe gqsqvqppps qeatplqqek llpaqlpaek evgppplpqea vplqkelpsl
     121   qhpneqkegt papfgdqshp epeswnaaqh cqqdrsqggw ghrldgfppg rpspdnlnqi
     181   clpnrqhvvy gpwnlpqssy shltrqgetl nfleigysrc chcrshtnrl ecaklvweea
     241   msrfceaefs vktrphwcct rqgearfscf qeeapqphyq lracpshqpd issglelpfp
     301   pgyptldnik nichlrrfrs vprnlpatdp lqrellaliq lerefqrccr qgnnhtctwk
     361   awedtldkyc dreyavkthh hlccrhppsp trdecfarra pypnydrdil tidigrvtpn
     421   lmghlegnqr vltkhkhipg lihnmtarcc dlpfpeqacc aeeekltfin dlcgprrniw
     481   rdpalccyls pgdeqvncfn inylrnvalv sgdtenakgq geqgstggtn isstsepkee Protein sequence isoform 2 (SEQ ID NO (61)):
       1   mgttaraalv ltylavasaa seggftatgq rqlrpehfqe vgyaappspp lsrslpmdhp
      61   dssqhgppfe gqsqvqppps qeatplqqek llpaqlpaek evgppplpqea vplqkelpsl
     121   qhpneqkegt papfgdqshp epeswnaaqh cqqdrsqggw ghrldgfppg rpspdnlnqi
     181   clpnrqhvvy gpwnlpqssy shltrqgetl nfleigysrc chcrshtnrl ecaklvwedt
     241   ldkycdreya vkthhhlccr hppsptrdec farrapypny drdiltidig rvtpnlmghl
     301   cgnqrvltkh khipglihnm tarccdlpfp eqaccaeeek ltfindlcgp rrniwrdpal
     361   ccylspgdeq vncfninylr nvalvsgdte nakgqgeqgs tggtnissts epkee Protein sequence isoform 3 (SEQ ID NO (62)):
       1   mgttaraalv ltylavasaa seggftatgq rqlrpehfqe vgyaappspp lsrslpmdhp
      61   dssqhgppfe gqsgkegrgp rphsqpwlge rvgcshipps ivqpppsqea tplqqekllp
     121   aqlpaekevg pplpqeavpl qkelpslqhp neqkegtpap fgdqshpepe swnaaqhcqq
     181   drsqggwghr ldgfppgrps pdnlnqiclp nrqhvvygpw nlpqssyshl trqgetlnfl
     241   eigysrcchc rshtnrleca klvweeamsr fceaefsvkt rphwcctrqg earfscfqee
     301   apqphyqlra cpshqpdiss glelpfppgv ptldniknic hlrrfrsvpr nlpatdplqr
     361   ellaliqler efqrccrqgn nhtctwkawe dtldkycdre yavkthhhlc crhppsptrd
     421   ecfarrapyp nydrdiltid igrvtpnlmg hlcgnqrvlt khkhipglih nmtarccdlp
     481   fpeqaccaee ekltfindlc gprrniwrdp alccylspgd eqvncfniny lrnvalvsgd
     541   tenakgqgeq gstggtniss tsepkee
```

TABLE 2-continued

```
Gene ID:           Y3
Gene symbol:       CLDN1
Gene description:  claudin 1
Unigene:           Hs.439060
Genbank:           AY358652
Entrez Gene:       9076
Refseq:            NM_021101
Protein sequence (SEQ ID NO (63)):
       1    managlqllg filaflgwig aivstalpqw riysyagdni vtaqamyegl wmscvsqstg
      61    qiqckvfdsl lnlsstlqat ralmvvgill gviaifvatv gmkcmkcled devqkmrmav
     121    iggaifflag lailvatawy gnrivqefyd pmtpvnarye fgqalftgwa aaslcllgga
     181    llccscprkt tsyptprpyp kpapssgkdy v Gene ID:           Y4
Gene symbol:       SFN
Gene description:  stratifin
Unigene:           Hs.523718
Genbank:           AF029082
Entrez Gene:       2810
Refseq:            NM_006142
Protein sequence (SEQ ID NO (64)):
       1    merasliqka klaeqaerye dmaafmkgav ekgeelscee rnllsvaykn vvggqraawr
      61    vlssieqksn eegseekgpe vreyrekvet elqgvcdtvl glldshlike agdaesrvfy
     121    lkmkgdyyry laevatgddk kriidsarsa yqeamdiskk empptnpirl glalnfsvfh
     181    yeianspeea islakttfde amadlhtlse dsykdstlim qllrdnltlw tadnageegg
     241    eapqepqs Gene ID:           Y5
Gene symbol:       CD9
Gene description:  CD9 antigen
Unigene:           Hs.114286
Genbank:           AY966455
Entrez Gene:       928
Refseq:            NM_001769
Protein sequence (SEQ ID NO (65)):
       1    mpvkggtkci kyllfgfnfi fwlagiavla iglwlrfdsq tksifeqetn nnnssfytgv
      61    yiligagalm mlvgflgccg avqesqcmlg lffgfllvif aieiaaaiwg yshkdevike
     121    vqefykdtyn klktkdepqr etlkaihyal nccglaggve qfisdicpkk dvletftvks
     181    cpdaikevfd nkfhiigavg igiawmifg mifsmilcca irmremv Gene ID:           Y6
Gene symbol:       CD109
Gene description:  CD109 antigen
Unigene:           Hs.399891
Genbank:           AF410459
Entrez Gene:       135228
Refseq:            NM_133493 | NM_001159587 | NM_001159588
Protein sequence isoform 1 (SEQ ID NO (66)):
       1    mqgpplltaa hllcvctaal avapgprflv tapgiirpgg nvtigvelle hcpsqvtvka
      61    ellktasnit vsvleaegvf ekgsfktltl pslplnsade iyelrvtgrt qdeilfsnst
     121    rlsfetkris vfiqtdkaly kpkqevkfri vtlfsdfkpy ktslnilikd pksnliqqwl
     181    sqqsdlgvis ktfqlsshpi lgdwsiqvqv ndqtyyqsfq vseyvlpkfe vtlqtplycs
     241    mnskhlngti takytygkpv kgdvtltflp lsfwgkkkni tktfkingsa nfsfndeemk
     301    nvmdssngls eyldlssspgp veilttvtes vtgisrnvst nvffkqhdyi ieffdyttvl
     361    kpslnftatv kvtradrgnql tleerrnnvv itvtqrnyte ywsgsnsgnq kmeavqkiny
     421    tvpqsgtfki efpiledsse lqlkayflgs kssmavhslf kspsktyiql ktrdenikvg
     481    spfelvvsgn krlkelsymv vsrgqlvavg kqnstmfslt penswtpkac vivyyieddg
     541    eiisdvlkip vqlvfknkik lywskvkaep sekvslrisv tqpdsivgiv avdksvnlmn
     601    asnditmenv vhelelyntg yylgmfmnsf avfqecglwv ltdanltkdy idgvydnaey
     661    aerfmeeneg hivdihdfsl gssphvrkhf petwiwldtn mgyriyqefe vtvpdsitsw
     721    vatgfvised lglglttpv elqafqpffi flnlpysvir geefaleiti fnylkdatev
     781    kviieksdkf dilmtsnein atghqqtllv psedgatvlf pirpthlgei pitvtalspt
     841    asdavtqmil vkaegieksy sqsilldltd nrlqstlktl sfsfppntvt gservqitai
     901    gdvlgpsing laslirmpyg cgeqnminfa pniyildylt kkkqltdnlk ekalsfmrqg
     961    yqrellyqre dgsfsafgny dpsgstwlsa fvlrcflead pyididqnvl hrtytwlkgh
    1021    qksngefwdp grvihselqg gnkspvtlta yivtsllgyr kyqpnidvqe sihflesefs
    1081    rgisdnytla lityalssvg spkakealnm ltwraeqegg mqfwvssesk lsdswqprsl
    1141    dievaayall shflqfqtse gipimrwlsr qrnslggfas tqdttvalka lsefaalmnt
    1201    ertniqvtvt gpsspspvkf lidthnrlll qtaelavvqp tavnisangf gfaicqlnvv
    1261    ynvkasgssr rrrsiqnqea fdldvavken kddlnhvdln vctsfsgpgr sgmalmevnl
    1321    lsgfmvpsea islsetvkkv eydhgklnly ldsvnetqfc vnipavrnfk vsntqdasys
    1381    ivdyyeprrq avrsynsevk lsscdlcsdv qgcrpcedga sgshhhssvi fifcfkllyf
    1441    melwl Protein sequence isoform 2 (SEQ ID NO (67)):
       1    mqgpplltaa hllcvctaal avapgprflv tapgiirpgg nvtigvelle hcpsqvtvka
      61    ellktasnit vsvleaegvf ekgsfktltl pslplnsade iyelrvtgrt qdeilfsnst
     121    rlsfetkris vfiqtdkaly kpkqevkfri vtlfsdfkpy ktslnilikd pksnliqqwl
     181    sqqsdlgvis ktfqlsshpi lgdwsiqvqv ndqtyyqsfq vseyvlpkfe vtlqtplycs
     241    mnskhlngti takytygkpv kgdvtltflp lsfwgkkkni tktfkingsa nfsfndeemk
```

TABLE 2-continued

```
       301    nvmdssngls  eyldlsspgp  veilttvtes  vtgisrnvst  nvffkqhdyi  ieffdyttvl
       361    kpslnftatv  kvtradgnql  tleerrnnvv  itvtqrnyte  ywsgsnsgnq  kmeavqkiny
       421    tvpqsgtfki  efpiledsse  lqlkayflgs  kssmavhslf  kspsktyiql  ktrdenikvg
       481    spfelvvsgn  krlkelsymv  vsrgqlvavg  kqnstmfslt  penswtpkac  vivyyieddg
       541    eiisdvlkip  vqlvfknkik  lywskvkaep  sekvslrisv  tqpdsivgiv  avdksvnlmn
       601    asnditmenv  vhelelyntg  yylgmfmnsf  avfqecglwv  ltdanltkdy  idgvydnaey
       661    aerfmeeneg  hivdihdfsl  gssphyrkhf  petwiwldtn  mgyriyqefe  vtvpdsitsw
       721    vatgfvised  lglglttttpv  elqafqpffi  flnlpysvir  geefaleiti  fnylkdatev
       781    kviieksdkf  dilmtsnein  atghqqtllv  psedgatvlf  pirpthlgei  pitvtalspt
       841    asdavtqmil  vkaegieksy  sqsilldltd  nrlqstlktl  sfsfppntvt  gservqitai
       901    gdvlgpsing  laslirmpyg  cgeqnminfa  pniyildylt  kkkqltdnlk  ekalsfmrqg
       961    yqrellyqre  dgsfsafgny  dpsgstwlsa  fvlrcflead  pyididqnvl  hrtytwlkgh
      1021    qksngefwdp  grvihselqg  gnkspvtlta  yivtsllgyr  kyqpnidvqe  sihflesefs
      1081    rgisdnytla  lityalssvg  spkakealnm  ltwraeqegg  mqfwvssesk  lsdswqprsl
      1141    dievaayall  shflqfqtse  gipimrwlsr  qrnslggfas  tqdttvalka  lsefaalmnt
      1201    ertniqvtvt  gpsspslav   vqptavnisa  ngfgfaicql  nvvynvkasg  ssrrrrsiqn
      1261    qeafdldvav  kenkddlnhv  dlnvctsfsg  pgrsgmalme  vnllsgfmvp  seaislsetv
      1321    kkveydhgkl  nlyldsvnet  qfcvnipavr  nfkvsntqda  sysivdyyep  rrqavrsyns
      1381    evklsscdlc  sdvqgcrpce  dgasgshhhs  svififcfkl  lyfmelwl Protein sequence isoform 3 (SEQ ID NO (68)):
         1    mqgppllltaa hllcvctaal avapgprflv tapgiirpgg nvtigvelle hcpsqvtvka
        61    ellktasnit  vsvleaegvf  ekgsfktltl  psdpksnliq  qwlsqqsdlg  viskifqlss
       121    hpilgdwsiq  vqvndqtyyq  sfqvseyvlp  kfevtlqtpl  ycsmnskhln  gtitakytyg
       181    kpvkgdvtlt  flplsfwgkk  knitktfkin  gsanfsfnde  emknvmdssn  glsseyldlss
       241    pgpveiltttv tesvtgisrn vstnvffkqh dyiieffdyt tvlkpslnft atvkvtradg
       301    nqltleerrn nvvitvtqrn yteywsgsns gnqkmeavqk inytvpqsgt fkiefpiled
       361    sselqlkayf lgskssmavh slfkspskty iqlktrdeni kvgspfelvv sgnkrlkels
       421    ymvvsrgqlv avgkqnstmf sltpenswtp kacvivyyie ddgeiisdvl kipvqlvfkn
       481    kiklywskvk aepsekvslr isvtqpdsiv givavdksvn lmnasnditm envvhelely
       541    ntgyylgmfm nsfavfqecg lwvltdanlt kdyidgvydn aeyaerfmee neghivdihd
       601    fslgssphyr khfpetwiwl dtnmgyriyq efevtvpdsi tswvatgfvi sedlglgltt
       661    tpvelqafqp ffiflnlpys virgeefale itifnylkda tevkviieks dkfdilmtsn
       721    einatghqqt llvpsedgat vlfpirpthl geipitvtal sptasdavtq milvkaegie
       781    ksysqsilld ltdnrlqstl ktlsfsfppn tvtgservqi taigdvlgps inglaslirm
       841    pygcgeqnmi nfapniyild yltkkkqltd nlkekalsfm rqgyqrelly qredgsfsaf
       901    gnydpsgstw lsafvlrcfl eadpyididq nvlhrtytwl kghqksngef wdpgrvihse
       961    lqggnkspvt ltayivtsll gyrkyqpnid vqesihfles efsrgisdny tlalityals
      1021    svgspkakea lnmltwraeq eggmqfwvss esklsdswqp rsldievaay allshflqfq
      1081    tsegipimrw lsrqrnslgg fastqdttva lkalsefaal mntertniqv tvtgpsspsp
      1141    vkflidthnr lllqtaelav vqptavnisa ngfgfaicql nvvynvkasg ssrrrrsiqn
      1201    qeafdldvav kenkddlnhv dlnvctsfsg pgrsgmalme vnllsgfmvp seaislsetv
      1261    kkveydhgkl nlyldsvnet qfcvnipavr nfkvsntqda sysivdyyep rrqavrsyns
      1321    evklsscdlc sdvqgcrpce dgasgshhhs svififcfkl lyfmelwl Gene ID:              Y7
Gene symbol:          ITGB8
Gene description:     integrin, beta 8
Unigene:              Hs.592171
Genbank:              M73780
Entrez Gene:          3696
Refseq:               NM_002214
Protein sequence (SEQ ID NO (69)):
         1    mcgsalafft aafvclqndr rgpasflwaa wvfslvlglg qgednrcass naascarcla
        61    lgpecgwcvq edfisggsrs ercdivsnli skgcsvdsie ypsvhviipt eneintqvtp
       121    gevsiqlrpg aeanfmlkvh plkkypvdly ylvdvsasmh nnieklnsvg ndlsrkmaff
       181    srdfrlgfgs yvdktvspyi sihperihnq csdynldcmp phgyihvlsl tenitefeka
       241    vhrqkisgni dtpeggfdam lqaavceshi gwrkeakrll lvmtdqtshl aldsklagiv
       301    vpndgnchlk nnvyvksttm ehpslgqlse klidnninvi favqgkqfhw ykdllpllpg
       361    tiageieska anlnnlvvea yqklisevkv qvenqvqgiy fnitaicpdg srkpgmegcr
       421    nvtsndevlf nvtvtmkked vtggknyaii kpigfnetak ihihrncscq cednrgpkgk
       481    cvdetfldsk cfqcdenkch fdedqfsses ckshkdqpvc sgrgvcvcgk cschkiklgk
       541    vygkycekdd fscpyhhgnl caghgeceag rcqcfsgweg drcqcpsaaa qhcvnskgqv
       601    csgrgtcvcg rcectdprsi grfcehcptc ytackenwnc mqclhphnls qaildqckts
       661    calmeqqhyv dqtsecfssp sylriffiif ivtfligllk vliirqvilq wnsnkiksss
       721    dyrvsaskkd klilqsvctr avtyrrekpe eikmdiskln ahetfrcnf Gene ID:              Y8
Gene symbol:          EMP2
Gene description:     epithelial membrane protein 2
Unigene:              Hs.531561
Genbank:              BC009687
Entrez Gene:          2013
Refseq:               NM_001424
Protein sequence (SEQ ID NO (70)):
         1    mlvllaffia fhitsaallf iatvdnawwv gdeffadvwr ictnntnctv indsfqeyst
        61    lqavgqatmil stilcciaff ifvlqlfrlk qgerfvltsi iqlmsclcvm iaasiytdrr
       121    edihdknakf ypvtregsyg ysyilawvaf actfisgmmy lilrkrk
```

TABLE 2-continued

```
Gene ID:            Y9
Gene symbol:        FGFBP1
Gene description:   fibroblast growth factor binding protein 1
Unigene:            Hs.1690
Genbank:            BC008910
Entrez Gene:        9982
Refseq:             NM_005130
Protein sequence (SEQ ID NO (71)):
        1   mkicsltlls flllaaqvll vegkkkvkng lhskvvseqk dtlgntqikq ksrpgnkgkf
       61   vtkdqancrw aateqeegis lkvectqldh efscvfagnp tsclklkder vywkqvarnl
      121   rsqkdicrys ktavktrvcr kdfpesslkl vsstlfgntk prkektemsp rehikgkett
      181   psslavtqtm atkapecved pdmanqrkta lefcgetwss lctfflsivq dtsc Gene ID:            Y10
Gene symbol:        CDH3
Gene description:   cad herin 3, type 1, P-cadherin (placental)
Unigene:            Hs.191842
Genbank:            BC041846
Entrez Gene:        1001
Refseq:             NM_001793
Protein sequence (SEQ ID NO (72)):
        1   mglprgplas llllqvcwlq caasepcrav freaevtlea ggaeqepgqa lgkvfmgcpg
       61   qepalfstdn ddftvrnget vqerrslker nplkifpskr ilrrhkrdwv vapisvpeng
      121   kgpfpqrinq lksnkdrdtk ifysitgpga dsppegvfav eketgwllln kpldreeiak
      181   yelfghavse ngasvedpmn isiiivtdqnd hkpkftqdtf rgsvlegvlp gtsvmqvtat
      241   deddaiytyn gvvaysihsk epkdphdlmf tihrstgtis vissgldrek vpeytltiqa
      301   tdmdgdgstt tavavveild andnapmfdp qkyeahvpen avghevqrlt vtdldapnsp
      361   awratyylimg gddgdhftit thpesnqgil ttrkgldfea knqhtlyvev tneapfvlkl
      421   ptstativvh vedvneapvf vppskvvevq egiptgepvc vytaedpdke nqkisyrilr
      481   dpagwlamdp dsgqvtavgt ldredeqfvr nniyevmvla mdngsppttg tgtllltlid
      541   vndhgpvpep rqiticncqsp vrqvlnitdk dlsphtspfq aqltddsdiy wtaevneegd
      601   tvvlslkkfl kqdtydvhls lsdhgnkeql tviratvcdc hghvetcpgp wkggfilpvl
      661   gavlallfll lvllllvrkk rkikeplllp eddtrdnvfy ygeegggeed qdyditqlhr
      721   glearpevvl rndvaptiip tpmyrprpan pdeignfiie nlkaantdpt appydtllvf
      781   dyegsgsdaa slssltssas dqdqdydyln ewgsrfkkla dmyggedd Gene ID:            Y11
Gene symbol:        ITGB4
Gene description:   integrin, beta 4
Unigene:            Hs.632226
Genbank:            X53587
Entrez Gene:        3691
Refseq:             NM_000213 | NM_001005619 | NM_001005731
Protein sequence isoform 1 (SEQ ID NO (73)):
        1   magprpspwa rlllaalisv slsgtlanrc kkapvksctc cvrvdkdcay ctdemfrdrr
       61   cntqaellaa gcqresivvm essfqiteet qidttlrrsq mspqglrvrl rpgeeerhfel
      121   evfeplespv dlyilmdfsn smsddldnlk kmgqnlarvl sqltsdytig fgkfvdkvsv
      181   pqtdmrpekl kepwpnsdpp fsfknvislt edvdefrnkl qgerisgnld apeggfdail
      241   qtavctrdig wrpdsthllv fstesafhye adganvlagi msrnderchl dttgtytqyr
      301   tqdypsvptl vrllakhnii pifavtnysy syyeklhtyf pvsslgvlqe dssnivelle
      361   eafnrirsnl diraldsprg lrtevtskmf qktrtgsfhi rregevgiyqv qlralehvdg
      421   thvcqlpedq kgnihlkpsf sdglkmdagi icdvctcelq kevrsarcsf ngdfvcgqcv
      481   csegwsgqtc ncstgslsdi qpclregedk pcsgrgecqc ghcvcygegr yeggfceydn
      541   fqcprtsgfl cndrgrcsmg qcvcepgwtg pscdcplsna tcidsnggic ngrghcecgr
      601   chchqqslyt dticeinysa ihpglcedlr scvqcqawgt gekkgrtcee cnfkvkmvde
      661   lkraeevvvr csfrdeddddc tysytmegdg apgpnstvlv hkkkdcppgs fwwliplllll
      721   llpllalll lcwkycacck aclallpccn rghmvgfked hymlrenlma sdhldtpmlr
      781   sgnlkgrdvv rwkvtnnmqr pgfathaasi nptelvpygl slrvrlarlcte nllkpdtrec
      841   aqlrqeveen lnevyrqisg vhklqqtkfr qqpnagkkqd htivdtvlma prsakpallk
      901   ltekqveqra fhdlkvapgy ytltadqdar gmvefqegve lvdvrvplfi rpedddekql
      961   lveaidvpag tatlgrrlvn itiikeqard vvsfeqpefs vsrgdqvari pvirrvldgg
     1021   ksqvsyrtqd gtaqgnrdyi pvegellfqp geawkelqvk llelqevdsl lrgrqvrrfh
     1081   vqlsnpkfga hlgqphstti iirdpdeldr sftsqmlssq ppphgdlgap qnpnakaags
     1141   rkihfnwlpp sgkpmgyrvk ywiqgdsese ahlldskvps veltnlypyc dyemkvcayg
     1201   aqgegpyssl vscrthqevp sepgrlafnv vsstvtqlsw aepaetngei tayevcyglv
     1261   nddnrpigpm kkvlvdnpkn rmllienlre sqpyrytvka rngagwgper eaiinlatqp
     1321   krpmsipiip dipivdaqsg edydsflmys ddvlrspaqs qrpsysddtg cgwkfepllg
     1381   eeldlrryrw rlppelpirl sassgrssda eaphgppddg gaggkggslp rsatpgppge
     1441   hlvngrmdfa fpgstnslhr mtttsaaayg thlsphvphr vlstsstltr dynsltrseh
     1501   shsttlprdy stltsysshd srltagvpdt ptrlvfsalg ptslrvswqe prcerplqgy
     1561   sveyqllngg elhrlnipnp aqtsvvvedl lpnhsyvfry raqsqegwgr eregvities
     1621   qvhpqsplcp lpgsaftlst psapgplvft alspdslqls werprrpngd ivgylvtcem
     1681   aqgggpataf rvdgdspesr ltvpglsenv pykfkvqart tegfgpereg iitiesqdgg
     1741   pfpqlgsrag lfqhplqsey ssittthtsa tepflvdglt lgaqhleagg sltrhvtqef
     1801   vsrtlttsgt lsthmdqqff qt Protein sequence isoform 2 (SEQ ID NO (74)):
        1   magprpspwa rlllaalisv slsgtlanrc kkapvksctc cvrvdkdcay ctdemfrdrr
       61   cntqaellaa gcqresivvm essfqiteet qidttlrrsq mspqglrvil rpgeeerhfel
      121   evfeplespv dlyilmdfsn smsddldnlk kmgqnlarvl sqltsdytig fgkfvdkvsv
```

TABLE 2-continued

```
       181    pqtdmrpekl kepwpnsdpp fsfknvislt edvdefrnkl qgerisgnld apeggfdail
       241    qtavctrdig wrpdsthllv fstesafhye adganvlagi msrndcherchl dttgtytqyr
       301    tqdypsvptl vrllakhnii pifavtnysy syyeklhtyf pvsslgvlqe dssnivelle
       361    eafnrirsnl diraldsprg lrtevtskmf qktrtgsfhi rrgevgiyqv qlralehvdg
       421    thvcqlpedq kgnihlkpsf sdglkmdagi icdvctcelq kevrsarcsf ngdfvcgqcv
       481    csegwsgqtc ncstgslsdi qpclregedk pcsgrgecqc ghcvcygegr yegqfceydn
       541    fqcprtsgfl cndrgrcsmg qcvcepgwtg pscdcplsna tcidsnggic ngrghcecgr
       601    chchqqslyt dticeinysa ihpglcedlr scvqcqawgt gekkgrtcee cnfkvkmvde
       661    lkraeevvvr csfrdedddc tysytmegdg apgpnstvlv hkkkdcppgs fwwlipllll
       721    llpllalllll lcwkycacck aclallpccn rghmvgfked hymlrenlma sdhldtpmlr
       781    sgnlkgrdvv rwkvtnnmqr pgfathaasi nptelvpygl slrlarlcte nllkpdtrec
       841    aqlrqeveen lnevyrqisg vhklqqtkfr qqpnagkkqd htivdtvlma prsakpallk
       901    ltekqveqra fhdlkvapgy ytltadqdar gmvefqegve lvdvrvplfi rpedddekql
       961    lveaidvpag tatlgrrlvn itiikeqard vvsfeqpefs vsrgdqvari pvirrvldgg
      1021    ksqvsyrtqd gtaqgnrdyi pvegellfqp geawkelqvk llelqevdsl lrgrqvrrfh
      1081    vqlsnpkfga hlgqphstti iirdpdeldr sftsqmlssq ppphgdlgap qnpnakaags
      1141    rkihfnwlpp sgkpmgyrvk ywiqgdsese ahlldskvps veltnlypyc dyemkvcayg
      1201    aqgegpyssl vscrthqevp sepgrlafnv vsstvtqlsw aepaetngei tayevcyglv
      1261    nddnrpigpm kkvlvdnpkn rmllienlre sqpyrytvka rngagwgper eaiinlatqp
      1321    krpmsipiip dipivdaqsg edydsflmys ddvlrspsgs qrpsysddte hlvngrmdfa
      1381    fpgstnslhr mtttsaaayg thlsphvphr vlststltr dynsltrseh shsttlprdy
      1441    stltsvssshg lppiwehgrs rlplswalgs rsraqmkgfp psrgprdsii lagrpaapsw
      1501    gpdsrltagv pdtptrlvfs algptslrvs wqeprcerpl qgysveyqll nggelhrini
      1561    pnpaqtsvvv edllpnhsyv frvraqsqeg wgreregvit iesqvhpqsp lcplpgsaft
      1621    lstpsapgpl vftalspdsl qlswerprrp ngdivgylvt cemaqggggpa tafrvdgdsp
      1681    esrltvpgls envpykfkvq arttegfgpe regiitiesq dggpfpqlgs raglfqhplq
      1741    seyssittth tsatepflvd gltlgaqhle aggsltrhvt qefvsrtltt sgtlsthmdq
      1801    qffqt
```
Protein sequence isoform 3 (SEQ ID NO (75)):
```
         1    magprpspwa rllllaalisv slsgtlanrc kkapvksocte cvrvdkdcay ctdemfrdrr
        61    cntqaellaa gcqresivvm essfqiteet qidttlrrsq mspqglvrl rpgeerhfel
       121    evfeplespv dlyilmdfsn smsddldnlk kmgqnlarvl sqltsdytig fgkfvdkvsv
       181    pqtdmrpekl kepwpnsdpp fsfknvislt edvdefrnkl qgerisgnld apeggfdail
       241    qtavctrdig wrpdsthllv fstesafhye adganvlagi msrndcherchl dttgtytqyr
       301    tqdypsvptl vrllakhnii pifavtnysy syyeklhtyf pvsslgvlqe dssnivelle
       361    eafnrirsnl diraldsprg lrtevtskmf qktrtgsfhi rrgevgiyqv qlralehvdg
       421    thvcqlpedq kgnihlkpsf sdglkmdagi icdvctcelq kevrsarcsf ngdfvcgqcv
       481    csegwsgqtc ncstgslsdi qpclregedk pcsgrgecqc ghcvcygegr yegqfceydn
       541    fqcprtsgfl cndrgrcsmg qcvcepgwtg pscdcplsna tcidsnggic ngrghcecgr
       601    chchqqslyt dticeinysa ihpglcedlr scvqcqawgt gekkgrtcee cnfkvkmvde
       661    lkraeevvvr csfrdedddc tysytmegdg apgpnstvlv hkkkdcppgs fwwlipllll
       721    llpllalllll lcwkycacck aclallpccn rghmvgfked hymlrenlma sdhldtpmlr
       781    sgnlkgrdvv rwkvtnnmqr pgfathaasi nptelvpygl slrlarlcte nllkpdtrec
       841    aqlrqeveen lnevyrqisg vhklqqtkfr qqpnagkkqd htivdtvlma prsakpallk
       901    ltekqveqra fhdlkvapgy ytltadqdar gmvefqegve lvdvrvplfi rpedddekql
       961    lveaidvpag tatlgrrlvn itiikeqard vvsfeqpefs vsrgdqvari pvirrvldgg
      1021    ksqvsyrtqd gtaqgnrdyi pvegellfqp geawkelqvk llelqevdsl lrgrqvrrfh
      1081    vqlsnpkfga hlgqphstti iirdpdeldr sftsqmlssq ppphgdlgap qnpnakaags
      1141    rkihfnwlpp sgkpmgyrvk ywiqgdsese ahlldskvps veltnlypyc dyemkvcayg
      1201    aqgegpyssl vscrthqevp sepgrlafnv vsstvtqlsw aepaetngei tayevcyglv
      1261    nddnrpigpm kkvlvdnpkn rmllienlre sqpyrytvka rngagwgper eaiinlatqp
      1321    krpmsipiip dipivdaqsg edydsflmys ddvlrspsgs qrpsysddte hlvngrmdfa
      1381    fpgstnslhr mtttsaaayg thlsphvphr vlststltr dynsltrseh shsttlprdy
      1441    stltsvsshd srltagvpdt ptrlvfsalg ptslrvswqe prcerplqgy sveyqllngg
      1501    elhrlnipnp aqtsvvvedl lpnhsyvfrv raqsqegwgr eregvities qvhpqsplcp
      1561    lpgsaftlst psapgplvft alspdslqls werprrpngd ivgylvtcem aqgggpataf
      1621    rvdgdspesr ltvpglsenv pykfkvqart tegfgpereg iitiesqdgg pfpqlgsrag
      1681    lfqhplqsey ssittthtsa tepflvdglt lgaqhleagg sltrhvtqef vsrtlttsgt
      1741    lsthmdqqff qt
```

Gene ID: Y12
Gene symbol: LAMB3
Gene description: laminin, beta 3
Unigene: Hs.497636
Genbank: BC075838
Entrez Gene: 3914
Refseq: NM_000228
Protein sequence (SEQ ID NO (76)):
```
         1    mrpffllcfa lpgllhaqqa csrgacyppv gdllvgrtrf lrasstcglt kpetyctqyg
        61    ewqmkcckcd srqphnyysh rvenvasssg pmrwwqsqnd vnpvslqldl drrfqlqevm
       121    mefqgpmpag mliersssdfg ktwrvyqyla adctstfprv rqgrpqswqd vrcqslpqrp
       181    narlnggkvq lnlmdlvsgi patqsqkiqe vgeitnlrvn ftrlapvpqr gyhppsayya
       241    vsqlrlqgsc fchghadrca pkpgasagps tavqvhdvcv cqhntagpnc ercapfynnr
       301    pwrpaegqda hecqrcdcng hsetfchfda vfaasqgayg gvcdncrdht egkncercql
       361    hyfrnrrpga siqetciscr cdpdgavpca pcdpvtgqcv ckehvqgerc dlckpgftgl
       421    tyanpqgchr cdcnilgsrr dmpcdeesgr clclpnvvgp kcdqcapyhw klasgqgcep
       481    cacdphnsls pqcnqftgqc pcregfgglm csaaairqcp drtygdvatg cracdcdfrg
       541    tegpgcdkas grclcrpglt gprcdqcqrg ycnrypvcva chpcfqtyda dlreqalrfg
       601    rlrnataslw sgpgledrgl asrildaksk ieqiravlss pavteqevaq vasailslrr
```

TABLE 2-continued

```
       661    tlqglqldlp  leeetlslpr  dlesldrsfn  glltmyqrkr  eqfekissad  psgafrmlst
       721    ayeqsaqaaq  qvsdssrlld  qlrdsrreae  rlvrqagggg  gtgspklval  rlemsslpdl
       781    tptfnklcgn  srqmactpis  cpgelcpqdn  gtacgsrcrg  vlpraggafl  magqvaeqlr
       841    gfnaqlqrtr  qmiraaeesa  sqiqssaqrl  etqvsasrsq  meedvrrtrl  liqqvrdflt
       901    dpdtdaatiq  evseavlalw  lptdsatvlq  kmneiqaiaa  rlpnvdlvls  qtkqdiarar
       961    rlqaeaeear  srahavegqv  edvvgnlrqg  tvalqeaqdt  mqgtsrslrl  iqdrvaevqq
      1021    vlrpaeklvt  smtkqlgdfw  trmeelrhqa  rqqgaeavqa  qqlaegaseq  alsaqegfer
      1081    ikqkyaelkd  rlgqssmlge  qgariqsvkt  eaeelfgetm  emmdrmkdme  lellrgsqai
      1141    mlrsadltgl  ekrveqirdh  ingrvlyyat  ck
```

Gene ID:             Y13
Gene symbol:         CD55
Gene description:    CD55 antigen
Unigene:             Hs.126517
Genbank:             M31516
Entrez Gene:         1604
Refseq:              NM_000574
Protein sequence (SEQ ID NO (77)):

```
         1    mtvarpsvpa  alpllgelpr  lllvllclp   avwgdcglpp  dvpnaqpale  grtsfpedtv
        61    itykceesfv  kipgekdsvi  clkgsqwsdi  eefcnrscev  ptrlnsaslk  qpyitqnyfp
       121    vgtvveyecr  pgyrrepsls  pkltclqnlk  wstavefckk  kscpnpgeir  ngqidvpggi
       181    lfgatisfsc  ntgyklfgst  ssfclisgss  vqwsdplpec  reiycpappq  idngiiqger
       241    dhygyrqsvt  yacnkgftmi  gehsiyctvn  ndegewsgpp  pecrgkslts  kvppvtqkpt
       301    tvnvpttevs  ptsqktttkt  ttpnaqatrs  tpvsrttkhf  hettpnkgsg  ttsgttrlls
       361    ghtcftltgl  lgtlvtmgll  t
```

Gene ID:             Y14
Gene symbol:         CLDN16
Gene description:    claudin 16
Unigene:             Hs.251391
Genbank:             BC069682
Entrez Gene:         10686
Refseq:              NM_006580
Protein sequence (SEQ ID NO (78)):

```
         1    mtsrtpllvt  aclyysycns  rhlqggvrks  krpvfshcqv  petqktdtrh  lsgaragvcp
        61    cchpdgllat  mrdllqyiac  ffaffsagfl  ivatwtdcwm  vnaddslevs  tkerglwwec
       121    vtnafdgirt  cdeydsilae  hplklvvtra  lmitadilag  fgfltlllgl  dcvkflpdep
       181    yikvricfva  gatlliagtp  giigsvwyav  dvyverstiv  lhnifliqy   kfgwscwlgm
       241    agslgcflag  avltcclylf  kdvgpernyp  yslrkaysaa  gvsmaksysa  prtetakmya
       301    vdtrv
```

Gene ID:             Y15
Gene symbol:         LAMA3
Gene description:    laminin, alpha 3
Unigene:             Hs.436367
Genbank:             AY327115
Entrez Gene:         3909
Refseq:              NM_198129 | NM_001127717 | NM_000227 | NM_001127718
Protein sequence isoform 1 (SEQ ID NO (79)):

```
         1    maaaarprgr  algpvlpptp  lllvlrvlp   acgatardpg  aaaglslhpt  yfnlaeaari
        61    watatcgerg  pgegrpqpel  ycklvggpta  pgsghtiqgq  fcdycnsedp  rkahpvtnai
       121    dgserwwqsp  plssgtqynr  vnltldlgql  fhvayilikf  ansprpdlwv  lersvdfgst
       181    yspwqyfahs  kvdclkefgr  eanmavtrdd  dvlcvteysr  ivplengevv  vslingrpga
       241    knftfshtlr  eftkatnirl  rflrtntllg  hliskaqrdp  tvtrryyysi  kdisiggqcv
       301    cnghaevcni  nnpeklfrce  cqhhtcgetc  drcctgynqr  rwrpawqeqs  heceacnchg
       361    hasncyydpd  verqqaslnt  qgiyagggvc  incqhntagv  nceqcakgyt  rpygvpvdap
       421    dgcipcscdp  ehadgceqgs  grchckpnfh  gdncekcaig  yynfpfclri  pifpvstpss
       481    edpvagdikg  cdcnlegvlp  eicdahgrcl  crpgvegprc  dtcrsgfysf  picqacwcsa
       541    lgsyqmpcss  vtgqcecrpg  vtgqrcdrcl  sgaydfphcq  gsssacdpag  tinsnlgycq
       601    cklhvegptc  srckllywnl  dkenpsgcse  ckchkagtvs  gtgecrqgdg  dchckshvgg
       661    dscdtcedgy  faleksnyfg  cqgcqcdigg  alssmcsgps  gvcqcrehvv  gkvcqrpenn
       721    yyfpdlhhmk  yeiedgstpn  grdlrfgfdp  lafpefswrg  yaqmtsvqnd  vritlnvgks
       781    sgslfrvilr  yvnpgteavs  ghitiypswg  aaqskeiifl  pskepafvtv  pgngfadpfs
       841    itpgiwvaci  kaegvlldyl  vllprdyyea  svlqlpvtep  cayagppqen  cllyqhlpvt
       901    rfpctlacea  rhflldgepr  pvavrqptpa  hpvmvdlsgr  evelhlrlri  pqvghyvvvv
       961    eysteaaqlf  vvdvnvkssg  svlagqvniy  scnysvlcrs  avidhmsria  myelladadi
      1021    qlkghmarfl  lhqvciipie  efsaeyvrpq  vhciasygrf  vnqsatcvsl  ahetpptali
      1081    ldvlsgrpfp  hlpqqsspsv  dvlpgvtlka  pqnqvtlrgr  vphlgryvfv  ihfyqaahpt
      1141    fpaqvsvdgg  wpragsfhas  fcphvlgcrd  qviaegqief  disepevaat  vkvpegkslv
      1201    lvrvlvvpae  nydyqilhkk  smdkslefit  ncgknsfyld  pqtasrfckn  sarslvafyh
      1261    kgalpcechp  tgatgphcsp  eggqcpcqpn  vigrqctrca  tghygfprck  pcscgrrlce
      1321    emtgqcrcpp  rtvrpqcevc  ethsfsfhpm  agcegcncsr  rgtieaampe  cdrdsgqcrc
      1381    kpritgrqcd  rcasgfyrfp  ecvpcncnrd  gtepgvcdpg  tgaclckenv  egtecnvcre
      1441    gsfhldpanl  kgctscfcfg  vnnqchsshk  rrtkfvdmlg  whletadrvd  ipvsfnpgsn
      1501    smvadlqelp  atihsaswva  ptsylgdkvs  syggyltyqa  ksfglpgdmv  llekkpdvql
      1561    tgqhmsiiye  etntprpdrl  hhgrvhvveg  nfrhassrap  vsreelmtvl  srladvriqg
      1621    lyftetqrlt  lsevgleeas  dtgsgriala  veicacppay  agdscqgcsp  gyyrdhkgly
      1681    tgrcvpcncn  ghsnqcdgs   gicvncqhnt  agehcercqe  gyygnavhgs  cracpcphtn
      1741    sfatgcvvng  gdvrcscag   ytgtqcerca  pgyfgnpqkf  ggscqpcscn  sngqlgschp
      1801    ltgdcinqep  kdsspaeecd  dcdsevmttl  ndlatmgeql  rlyksqlqgl  sasagllqm
```

TABLE 2-continued

```
1861        rhmetqakdl  rnqllnyrsa  isnhgskieg  lereltdlnq  efetlqekaq  vnsrkaqtln
1921        nnvnratqsa  keldvkiknv  irnvhilllq  isgtdgegnn  vpsgdfsrew  aeaqrmmrel
1981        rnrnfgkhlr  eaeadkresq  lllnrirtwq  kthqgenngl  ansirdslne  yeaklsdlra
2041        rlqeaaaqak  qanglngene  ralgaiqrqv  keinslqsdf  tkylttadss  llqtnialql
2101        meksqkeyek  laaslnearq  elsdkvrels  rsagktslve  eaekharslq  elakqleeik
2161        rnasgdelvr  cavdaataye  nilnaikaae  daanraasas  esalqtvike  dlprkaktls
2221        snsdkllnea  kmtqkklkqe  vspalnnlqq  tlnivtvqke  vidtnlttlr  dglhgiqrgd
2281        idamissaks  mvrkanditd  evldglnpiq  tdverikdty  grtqnedfkk  altdadnsvn
2341        kltnklpdlw  rkiesinqql  lplgnisdnm  drireliqqa  rdaaskvavp  mrfngksgve
2401        vrlpndledl  kgytslslfl  qrpnsrengg  tenmfvmylg  nkdasrdyig  mavvdgqltc
2461        vynlgdreae  lqvdqiltks  etkeavmdrv  kfqriyqfar  lnytkgatss  kpetpgvydm
2521        dgrnsntlln  ldpenvvfyv  ggyppdfklp  srlsfppykg  cielddlnen  vlslynfkkt
2581        fnlnttevep  crrrkeesdk  nyfegtgyar  vptqphapip  tfgqtiqttv  drgllffaen
2641        gdrfislnie  dgklmvrykl  nselpkergv  gdainngrdh  siqikigklq  krmwinvdvq
2701        ntiidgevfd  fstyylggip  iairerfnis  tpafrgcmkn  lkktsgvvrl  ndtvgvtkkc
2761        sedwklvrsa  sfsrggqlsf  tdlglppteh  lqasfgfqtf  qpsgilldhq  twtrnlqvtl
2821        edgyielsts  dsgspifksp  qtymdgllhy  vsvisdnsgl  rlliddqllr  nskrlkhiss
2881        srqslrlggs  nfegcisnvf  vqrlslspev  ldltsnslkr  dvslggcsln  kppflmllkg
2941        strfnktktf  rinqllqdtp  vasprsvkvw  qdacsplpkt  qanhgalqfg  diptshllfk
3001        lpqellkprs  qfavdmqtts  srglvfhtgt  knsfmalyls  kgrlvfalgt  dgkklriksk
3061        ekcndgkwht  vvfghdgekg  rlvvdglrar  egslpgnsti  sirapvylgs  ppsgkpkslp
3121        tnsfvgclkn  fqldskplyt  psssfgvssc  lggplekgiy  fseegghvvl  ahsvllgpef
3181        klvfsirprs  ltgilihigs  qpgkhlcvyl  eagkvtasmd  sgaggtstsv  tpkqslcdgq
3241        whsvavtikq  hilhleldtd  ssytagqipf  ppastqeplh  lggapanltt  lripvwksff
3301        gclrnihvnh  ipvpvteale  vqgpvslngc  pdq
Protein sequence isoform 3 (SEQ ID NO: 80):
   1        maaaarprgr  algpvlpptp  lllvlrvlp   acgatardpg  aaaglslhpt  yfnlaeaari
  61        watatcgerg  pgegrpqpel  ycklvggpta  pgsghtiqgq  fcdycnsedp  rkahpvtnai
 121        dgserwwqsp  plssgtqynr  vnltldlgql  fhvayilikf  ansprpdlwv  lersvdfgst
 181        yspwqyfahs  kvdclkefgr  eanmavtrdd  dvlcvteysr  ivplengevv  vslingrpga
 241        knfftfshtlr eftkatnirl  rflrtntllg  hliskaqrdp  tvtrryyysi  kdisiggqcv
 301        cnghaevcni  nnpeklfrce  cqhhtcgetc  drcctgynqr  rwrpaaweqs  heceacnchg
 361        hasncyydpd  verqqaslnt  qglyagggvc  incqhntagv  nceqcakgyy  rpygvpvdap
 421        dgcipcscdp  ehadgceqgs  grchckpnfh  gdncekcaig  yynfpfclri  pifpvstpss
 481        edpvagdikg  cdcnlegvlp  eicdahgrcl  crpgvegprc  dtcrsgfysf  picqacwcsa
 541        lgsyqmpcss  vtgqcecrpg  vtgqrcdrcl  sgaydfphcq  gsssacdpag  tinsnlgycq
 601        cklhvegptc  srckllywnl  dkenpsgcse  dchckshvgg  gtgcrqgdg   gkvcqrpenn
 661        dscdtcedgy  faleksnyfg  cqgcqcdigg  alssmcsgps  gvcqcrehvv  gkvcqrpenn
 721        yyfpdlhhmk  yeiedgstpn  grdlrfgfdp  lafpefswrg  yaqmtsvqnd  vritlnvgks
 781        sgslfrvilr  yvnpgteavs  ghitiypswg  aaqskeiifl  pskepafvtv  pgngfadpfs
 841        itpgiwvaci  kaegvlldyl  vllprdyyea  svlqlpvtep  cayagppqen  cllyqhlpvt
 901        rfpctlacea  rhffldgepr  pvavrqptpa  hpvmvdlsgr  evelhlrlri  pqvghyvvvv
 961        eysteaaqlf  vvdvnvkssg  svlagqvniy  scnysvlcrs  avidhmsria  myelladadi
1021        qlkghmarfl  lhqvciipie  efsaeyvrpq  vhciasygrf  vnqsatcvsl  ahetpptali
1081        ldvlsgrpfp  hlpqqsspsv  dvlpgryvfv  pqnqvtlrgr  vphlgryvfv  ihfyqaahpt
1141        fpaqvsvdgg  wpragsfhas  fcphvlgcrd  qviaegqief  disepevaat  vkvpegkslv
1201        lvrvlvvpae  nydyqilhkk  smdkslefit  ncgknsfyld  pqtasrfckn  sarslvafyh
1261        kgalpcechp  tgatgphcsp  eggqcpcqpn  vigrqctrca  tghygfprck  pcscgrrlce
1321        emtgcrcpp   rtvrpqcevc  ethsfsfhpm  agcegcncsr  rgtieaampe  cdrdsggcrc
1381        kpritgrqcd  rcasgfyrfp  ecvpcncnrd  gtepgvcdpg  tgaclckenv  egtecnvcre
1441        gsfhldpanl  kgctscfcfg  vnnqchsshk  rrtkfvdmlg  whletadrvd  ipvsfnpgsn
1501        smvadlqelp  atihsaswva  ptsylgdkvs  syggyltyqa  ksfglpgdmv  llekkpdvql
1561        tgqhmsiiye  etntprpdrl  hhgrvhvveg  nfrhassrap  vsreelmtvl  srladvriqg
1621        lyftetqrlt  lsevgleeas  dtgssgriala veicacppay  agdscqgcsp  gyyrdhkgly
1681        tgrcvpcncn  ghsnqcqdgs  gicvncqhnt  agehcercqe  gyygnavhgs  cracpcphtn
1741        sfatgcvvng  gdvrcsckag  ytgtqcerca  pgyfgnpqkf  ggscqpcscn  snqglgschp
1801        ltgdcinqep  kdsspaeecd  dcdscvmtll  ndlatmgeql  rlvksqlqgl  sasaglleqm
1861        rhmetqakdl  rnqllnyrsa  isnhgskieg  lereltdlnq  efetlqekaq  vnsrkaqtln
1921        nnvnratqsa  keldvkiknv  irnvhmlnri  rtwqkthqge  nnglansird  slneyeakls
1981        dlrarlqeaa  aqakqanglin qeneralgai qrqvkeinsl  qsdftkyltt  adssllqtni
2041        alqlmeksqk  eyeklaasln  earqelsdkv  relsrsagkt  slveeaekha  rslqelakql
2101        eeikrnasgd  elvrcavdaa  tayenilnai  kaaedaanra  asasesalqt  vikedlprka
2161        ktlssnsdkl  lneakmtqkk  lkqevspaln  nlqqtlnivt  vqkevidtnl  ttlrdglhgi
2221        qrgdidamis  saksmvrkan  ditdevldgl  npiqtdveri  kdtygrtqne  dfkkaltdad
2281        nsvnkltnkl  pdlwrkiesi  nqqllplgni  sdnmdrirel  iqqardaask  vavpmrfngk
2341        sgvevrlpnd  ledlkgytsl  slflqrpnsr  enggtenmfv  mylgnkdasr  dyigmavvdg
2401        qltcvynlgd  reaelqvdqi  ltksetkeav  mdrvkfqriy  qfarlnytkg  atsskpetpg
2461        vydmdgrnsn  tllnldpenv  vfyvggyppd  fklpsrlsfp  pykgcieldd  lnenvlslyn
2521        fkktfnlntt  evepcrrrke  esdknyfegt  gyarvptqph  apiptfgqti  qttvdrgllf
2581        faengdrfis  lniedgklmv  ryklnselpk  ergvgdainn  grdhsiqiki  gklqkrmwin
2641        vdvqntiidg  evfdfstyyl  ggipiairer  fnistpafrg  cmknlkktsg  vvrlndtvgv
2701        tkkcsedwkl  vrsasfsrgg  qlsftdlglp  pteh lqasfg  fqtfqpsgil  ldhqtwtrnl
2761        qvtledgyie  lstsdsgspi  fkspqtymdg  llhyvsvisd  nsglrllidd  qllrnskrlk
2821        hisssrqslr  lggsnfegci  snvfvqrlsl  spevldltsn  slkrdvslgg  cslnkppflm
2881        llkgstrfnk  tktfrinqll  qdtpvasprs  vkvwqdacsp  lpktqanhga  lqfgdiptsh
2941        llfklpqell  kprsqfavdm  qttssrglvf  htgtknsfma  lylskgrlvf  algtdgkklr
3001        ikskekcndg  kwhtvvfghd  gekgrlvvdg  lraregslpg  nstisirapv  ylgsppsgkp
3061        kslptnsfvg  clknfqldsk  plytpsssfg  vssclggple  kgiyfseegg  hvvlahsvll
3121        gpefklvfsi  rprsltgili  higsqpgkhl  cvyleagkvt  asmdsgaggt  stsvtpkqsl
```

TABLE 2-continued

```
     3181   cdgqwhsvav tikqhilhle ldtdssytag qipfppastq eplhlggapa nlttlripvw
     3241   ksffgclrni hvnhipvpvt ealevqgpvs lngcpdq Protein sequence isoform 2 (SEQ ID NO (81)):
        1   mppavrrsac smgwlwifga algqclgyss qqqrvpflqp pgqsqlqasy vefrpsqgcs
       61   pgyyrdhkgl ytgrcvpcnc nghsnqcqdg sgicvncqhn tagehcercq egyygnavhg
      121   scracpcpht nsfatgcvvn ggdvrcscka gytgtqcerc apgyfgnpqk fggscqpcsc
      181   nsngqlgsch pltgdcinqe pkdsspaeec ddcdscvmtl lndlatmgeq lrlvksqlqg
      241   lsasaglleq mrhmetqakd lrnqllnyrs aisnhgskie glereltdln qefetlqeka
      301   qvnsrkaqtl nnnvnratqs akeldvkikn virnvhillk qisgtdgegn nvpsgdfsre
      361   waeaqrmmre lrnrnfgkhl reaeadkres qlllnrirtw qkthqgenng lansirdsln
      421   eyeaklsdlr arlqeaaaqa kqanglnqen eralgaiqrq vkeinslqsd ftkylttads
      481   sllqtnialq lmeksqkeye klaaslnear qelsdkvrel srsagktslv eeaekharsl
      541   qelakqleei krnasgdelv rcavdaatay enilnaikaa edaanraasa sesalqtvik
      601   edlprkaktl ssnsdkllne akmtqkklkq evspalnnlq qtlnivtvqk evidtnlttl
      661   rdglhgiqrg didamissak smvrkandit devldglnpi qtdverikdt ygrtqnedfk
      721   kaltdadnsv nkltnklpdl wrkiesinqq lllplgnislk mdrireliqq ardaaskvav
      781   pmrfngksgv evrlpndled lkgytslslf lqrpnsreng gtenmfvmyl gnkdasrdyi
      841   gmavvdgqlt cvynlgdrea elqvdqiltk setkeavmdr vkfqriyqfa rlnytkgats
      901   skpetpgvyd mdgrnsntll nldpenvvfy vggyppdfkl psrlsfppyk gcielddlne
      961   nvlslynfkk tfnlntteve pcrrrkeesd knyfegtgya rvptqphapi ptfgqtiqtt
     1021           vdrgllffae ngdrfislni edgklmvryk lnselpkerg vgdainngrd hsiqikigkl
     1081   qkrmwinvdv qntiidgevf dfstyylggi piairerfni stpafrgcmk nlkktsgvvr
     1141   lndtvgvtkk csedwklvrs asfsrggqls ftdlglpptd hlqasfgfqt fqpsgilldh
     1201   qtwtrnlqvt ledgyielst sdsgspifks pqtymdgllh yvsvisdnsg lrlliddqll
     1261   rnskrlkhis ssrqslrlgg snfegcisnv fvqrlslspe vldltsnslk rdvslggcsl
     1321   nkppflmllk gstrfnktkt frinqllqdt pvasprsvkv wqdacsplpk tqanhgalqf
     1381   gdiptshllf klpqellkpr sqfavdmqtt ssrglvfhtg tknsfmalyl skgrlvfalg
     1441   tdgkklriks kekcndgkwh tvvfghdgek grlvvdgira regslpgnst isirapvylg
     1501   sppsgkpksl ptnsfvgclk nfqldskply tpsssfgvss clggplekgi yfseegghvv
     1561   lahsvllgpe fklvfsirpr sltgilihig sqpgkhlcvy leagkvtasm dsgaggtsts
     1621   vtpkqslcdg qwhsvavtik qhilhleldt dssytagqip fppastqepl hlggapanlt
     1681   tlripvwksf fgclrnihvn hipvpvteal evqgpvslng cpdq Protein sequence isoform 4 (SEQ ID NO (82)):
        1   mppavrrsac smgwlwifga algqclgyss qqqrvpflqp pgqsqlqasy vefrpsqgcs
       61   pgyyrdhkgl ytgrcvpcnc nghsnqcqdg sgicvncqhn tagehcercq egyygnavhg
      121   scracpcpht nsfatgcvvn ggdvrcscka gytgtqcerc apgyfgnpqk fggscqpcsc
      181   nsngqlgsch pltgdcinqe pkdsspaeec ddcdscvmtl lndlatmgeq lrlvksqlqg
      241   lsasaglleq mrhmetqakd lrnqllnyrs aisnhgskie glereltdln qefetlqeka
      301   qvnsrkaqtl nnnvnratqs akeldvkikn virnvhmlnr irtwqkthqg ennglansir
      361   dslneyeakl sdlrarlqea aaqakqangl nqeneralga iqrqvkeins lqsdftkylt
      421   tadssllqtn ialqlmeksq keyeklaasl nearqelsdk vrelsrsagk tslveeaekh
      481   arslqelakq leeikrnasg delvrcavda atayenilna ikaaedaanr aasasesalq
      541   tvikedlprk aktlssnsdk llneakmtqk klkqevspal nnlqqtlniv tvqkevidtn
      601   lttlrdglhg iqrgdidami ssaksmvrka nditdevldg lnpiqtdver ikdtygrtqn
      661   edfkkaltda dnsvnkltnk lpdlwrkies inqqlllplgn nsrdaaskvav
      721   kvavpmrfng ksgvevrlpn dledlkgyts lslflqrpns renggtenmf vmylgnkdas
      781   rdyigmavvd gqltcvynlg dreaelqvdq iltksetkea vmdrvkfqri yqfarlnytk
      841   gatsskpetp gvydmdgrns ntllnldpen vvfyvggypp dfklpsrlsf ppykgcield
      901   dlnenvlsly nfkktfnlnt teveperrrk eesdknyfeg tgyarvptqp hapiptfgqt
      961   iqttvdrgll ffaengdrfi slniedgklm vryklnselp kergvgdain ngrdhsiqik
     1021   igklqkrmwi nvdvqntiid gevfdfstyy lggipiaire rfnistpafr gcmknlkkts
     1081   gvvrlndtvg vtkkcsedwk lvrsasfsrg gqlsftdlgl pptdhlqasf gfqtfqpsgi
     1141   lldhqtwtrn lqvtledgyi elstsdsgsp ifkspqtymd gllhyvsvis dnsglrllid
     1201   dqllrmskrl khisssrqsl rlggsnfegc isnvfvqrls lspevldlts nslkrdvslg
     1261   gcslnkppfl mllkgstrfn ktktfrinql lqdtpvaspr svkvwqdacs plpktqanhg
     1321   alqfgdipts hllfklpqel kprsqfavd mqttssrglv fhtgtknsfm alylskgrlv
     1381   falgtdgkkl rikskekcnd gkwhtvvfgh dgekgrlvvd glraregslp gnstisirap
     1441   vylgsppsgk pkslptnsfv gclknfqlds kplytpsssf gvssclggpl ekgiyfseeg
     1501   ghvvlahsvl lgpefklvfs irprsltgil ihgsqpgkh lcvyleagkv tasmdsgagg
     1561   tststvtpkqs lcdgqwhsva vtikqhilhl eldtdssyta gqipfppast qeplhlggap
     1621   anlttlripv wksffgclrn ihvnhipvpv tealevqgpv slngcpdq Gene ID:              Y16
Gene symbol:          CD40
Gene description:     CD40 molecule
Unigene:              Hs.472860
Genbank:              AB209660
Entrez Gene:          958
Refseq:               NM_001250 | NM_152854
Protein sequence isoform 1 (SEQ ID NO (83)):
        1   mvrlplqcvl wgclltavhp epptacrekq ylinsqccsl cqpgqklvsd cteftetecl
       61   pcgesefldt wnrethchqh kycdpnlglr vqqkgtsetd tictceegwh ctseacescv
      121   lhrscspgfg vkqiatgvsd ticepcpvgf fsnvssafek chpwtscetk dlvvqqagtn
      181   ktdvvcgpqd rlralvvipi ifgilfaill vlvfikkvak kptnkaphpk qepqeinfpd
      241   dlpgsntaap vqetlhgcqp vtqedgkesr isvqerq
```

TABLE 2-continued

```
Protein sequence isoform 2 (SEQ ID NO (84)):
        1   mvrlplqcvl wgclltavhp epptacrekq ylinsqccsl cqpgqklvsd cteftetecl
       61   pcgesefldt wnrethchqh kycdpnlglr vqqkgtsetd tictceegwh ctseacescv
      121   lhrscspgfg vkqiatgvsd ticepcpvgf fsnvssafek chpwtrspgs aespggdphh
      181   lrdpvchplg aglyqkggqe anq Gene ID:              Y17
Gene symbol:          COL17A1
Gene description:     collagen, type XVII, alpha 1
Unigene:              Hs.117938
Genbank:              AL138761
Entrez Gene:          1308
Refseq:               NM_000494
Protein sequence (SEQ ID NO (85)):
        1   mdvtkknkrd gtevteriyt etvttrltsl ppkggtsngy aktaslgggs rlekqslthg
       61   ssgyinstgs trghastssy rrahspastl pnspgstfer kthvtrhaye gsssgnsspe
      121   yprkefassss trgrsqtres eirvrlqsas pstrwteldd vkrllkgsrs asysptrnss
      181   ntlpipkkgt vetkivtass qsysgtydat ildanlpshv wsstlpagss mgtyhnnmtt
      241   qsssllntna ysagsvfgvp nnmascsptl hpglstsssv fgmqnnlaps lttlshgttt
      301   tstaygvkkn mpqspaavnt gvstsaactt svqsddllhk dckflilekd ntpakkemel
      361   limtkdsgkv ftaspasiaa tsfsedtlkk ekqaaynads glkaeangdl ktvstkgktt
      421   tadihsygss ggggsggggg vggagggpwg papawcpcgs ccswwkwllg llltwllllg
      481   llfglialae evrklkarvd elerirrsil pygdsmdrie kdrlqgmapa agadldkigl
      541   hsdsqeelwm fvrkklmmeq engnlrgspg pkgdmgspgp kgdrgfpgtp gipgplghpg
      601   pqgpkgqkgs vgdpgmegpm gqrgregpmg prgeagppgs gekgergaag epgphgppgv
      661   pgsvgpkgss gspgpqggppg pvglqglrge vglpgvkgdk gpmgppgpkg dqgekgprgl
      721   tgepgmrglp gavgepgakg amgpagpdgh qgprgeqglt gmpgirgppg psgdpgkpgl
      781   tgpqgpqglp gtpgrpgikg epgapgkivt segssmltvp gppgppgamg ppgppgapgp
      841   agpaglpghq evlnlqgppg ppgprgppgp sipgppgprg ppgeglpgpp ppgsflsns
      901   etflsgppgp pgppgpkgdg gppgprghqg eqglpgfsts gsssfglnlq gppgpppgpqgg
      961   pkgdkgdpgv pgalgipsgp seggsssstmy vsgppgppgp pgppgsisss gqeiqqyise
     1021   ymqsdsirsy lsgvqgppgp pgppgpvtti tgetfdysel ashvvsylrt sgygvslfss
     1081   sissedilav lqrddvrqyl rqylmgprgp pgppgasgdg sllsldyael ssrilsymss
     1141   sgisiglpgp pgppglpgts yeellsllrg sefrgivgps gppgppgipg nvwssisved
     1201   lssylhtagl sfipgppgpp gppgprgppg vsgalatyaa ensdsfrsel isyltspdvr
     1261   sfivgppgpp gpqgppgdsr llstdashsr gsssshsss vrrgssysss mstggggags
     1321   lgaggafgea agdrgpygtd igpgggygaa aeggmyagng gllgadfagd ldynelavry
     1381   sesmqrqgll qgmaytvqgp pgqpgpqgpp giskvfsays nvtadlmdff qtygaiqgpp
     1441   gqkgemgtpg pkgdrgpagp pghpgppgpr ghkgekgdkg dqvyagrrrr rsiavkp Gene ID:              Y18
Gene symbol:          DSC2
Gene description:     Desmocollin-2
Unigene:              Hs.95612
Genbank:              BC063291
Entrez Gene:          1824
Refseq:               NM_024422 | NM_004949
Protein sequence isoform Dsc2a (SEQ ID NO (86)):
        1   meaarpsgsw ngalcrllll tlailifasd acknvtlhvp skldaeklvg rvnlkecfta
       61   anlihssdpd fqiledgsvy ttntillsse krsftillsn tenqekkkif vflehqtkvl
      121   kkrhtkekvl rrakrrwapi pcsmlenslg pfplflqqvq sdtaqnytiy ysirgpgvdq
      181   eprnlfyver dtgnlyctrp vdreqyesfe iiafattpdg ytpelplpli ikiedendny
      241   pifteetytf tifencrvgt tvgqvcatdk depdtmhtrl kysiigqvpp sptlfsmhpt
      301   tgvitttssq ldrelidkyq lkikvqdmdg qyfglqttst ciiniddvnd hlptftrtsy
      361   vtsveentvd veilrvtved kdlvntanwr anytilkgne ngnfkivtda ktnegvlcvv
      421   kpinyeekqq milqigvvne apfsreaspr samstatvtv nvedqdegpe cnppiqtvrm
      481   kenaevgtts ngykaydpet rsssgirykk ltdptgwvti dentgsikvf rsldreaeti
      541   kngiynitvl asdqggrtct gtlgiilqdv ndnspfipkk tviickptms saeivavdpd
      601   epihgppfdf slessstsevq rmwrlkaind taarlsyqnd ppfgsyvvpi tvrdrlgmss
      661   vtsldvtlcd citendcthr vdpriggggv qlgkwailai llgiallfci lftlvcgass
      721   tskqpkvipd dlaqqnlivs nteapgddkv ysangfttqt vgasaqgvcg tvgsglkngg
      781   qetiemvkgg hqtsescrga ghhhtldscr gghtevdncr ytysewhsft qprlgekvyl
      841   cnqdenhkha qdyvltynye grgsvagsvg ccserqeedg lefldnlepk frtlaeacmk
      901   r Protein sequence isoform Dsc2b (SEQ ID NO (87)):
        1   meaarpsgsw ngalcrllll tlailifasd acknvtlhvp skldaeklvg rvnlkecfta
       61   anlihssdpd fqiledgsvy ttntillsse krsftillsn tenqekkkif vflehqtkvl
      121   kkrhtkekvl rrakrrwapi pcsmlenslg pfplflqqvq sdtaqnytiy ysirgpgvdq
      181   eprnlfyver dtgnlyctrp vdreqyesfe iiafattpdg ytpelplpli ikiedendny
      241   pifteetytf tifencrvgt tvgqvcatdk depdtmhtrl kysiigqvpp sptlfsmhpt
      301   tgvitttssq ldrelidkyq lkikvqdmdg qyfglqttst ciiniddvnd hlptftrtsy
      361   vtsveentvd veilrvtved kdlvntanwr anytilkgne ngnfkivtda ktnegvlcvv
      421   kplnyeekqq milqigvvne apfsreaspr samstatvtv nvedqdegpe cnppiqtvrm
      481   kenaevgtts ngykaydpet rsssgirykk ltdptgwvti dentgsikvf rsldreaeti
      541   kngiynitvl asdqggrtct gtlgiilqdv ndnspfipkk tviickptms saeivavdpd
```

TABLE 2-continued

```
    601    epihgppfdf slessstsevq rmwrlkaind taarlsyqnd ppfgsyvvpi tvrdrlgmss
    661    vtsldvticd citendcthr vdpriggggv qlgkwailai llgiallfci lftlvcgasg
    721    tskqpkvipd dlaqqnlivs nteapgddkv ysangfttqt vgasaqgvcg tvgsgikngg
    781    qetiemvkgg hqtsescrga ghhhtldscr gghtevdncr ytysewhsft qprlgeesir
    841    ghtlikn
```

Gene ID:              Y19
Gene symbol:          DSC1
Gene description:     Desmocollin-1
Unigene:              Hs.567260
Genbank:              X72925
Entrez Gene:          1823
Refseq:               NM_024211|NM_004948
Protein sequence isoform Dsc1a (SEQ ID NO (88)):

```
      1    malasaapgs ifckqllfsl lvltllcdac qkvylrvpsh lqaetlvgkv nleeclksas
     61    lirssdpafr iledgsiytt hdlilsserk sfsiflsdgq rreqqeikvv lsarenkspk
    121    krhtkdtalk rskrrwapip aslmenslgp fpqhvqqiqs daaqnytify sisgpgvdke
    181    pfnlfyiekd tgdifctrsi drekyeqfal ygyattadgy apeyplphii kieddndnap
    241    yfehrvtift vpencrsgts vgkvtatdld epdtlhtrlk ykilqqipdh pkhfsihpdt
    301    gvittttpfl drekcdtyql imevrdmggq pfglfntgti tisledednd ppsftetsyv
    361    teveenridv eilrmkvqdq dlpntphska vykilqgnen gnfiistdpn tnegvlcvvk
    421    plnyevnrqv ilqvgvinea qfskaasssqt ptmctttvtv kiidsdegpe chppvkviqs
    481    qdgfpaggel lgykaldpei ssgeglryqk lgdednwfei nqhtgdlrtl kvldreskfv
    541    knnqynisvv avdavgrsct gtlvvhlddy ndhapqidke vticqnnedf avlkpvdpdg
    601    pengppfqff ldnsasknwn ieekdgktai lrqrqnldyn yysvpiqikd rhglvathml
    661    tvrvcdcstp secrmkdkst rdvrpnvilg rwailamvlg svllcilft cfcvtakrtv
    721    kkcfpediaq qnlivsnteg pgeevteani rlpmqtsnic dtsmsvgtvg gqglktqqsf
    781    emvkggytld snkgghhqtl esvkgvgqgd tgryaytdwq sftqprlgek vylcgqdeeh
    841    khcedyvcsy nyegkgslag svgccsdrqe eeglefldhl epkfrtlakt cikk
```

Protein sequence isoform Dsc1b (SEQ ID NO (89)):

```
      1    malasaapgs ifckqllfsl lvltllcdac qkvylrvpsh lqaetlvgkv nleeclksas
     61    lirssdpafr iledgsiytt hdlilsserk sfsiflsdgq rreqqeikvv lsarenkspk
    121    krhtkdtalk rskrrwapip aslmenslgp fpqhvqqiqs daaqnytify sisgpgvdke
    181    pfnlfyiekd tgdifctrsi drekyeqfal ygyattadgy apeyplplii kieddndnap
    241    yfehrvtift vpencrsgts vgkvtatdld epdtlhtrlk ykilqqipdh pkhfsihpdt
    301    gvittttpfl drekcdtyql imevrdmggq pfglfntgti tisledednd ppsftetsyv
    361    teveenridv eilrmkvqdq dlpntphska vykilqgnen gnfiistdpn tnegvlcvvk
    421    plnyevnrqv ilqvgvinea qfskaasssqt ptmctttvtv kiidsdegpe chppvkviqs
    481    qdgfpaggel lgykaldpei ssgeglryqk lgdednwfei nqhtgdlrtl kvldreskfv
    541    knnqynisvv avdavgrsct gtlvvhlddy ndhapqidke vticqnnedf avlkpvdpdg
    601    pengppfqff ldnsasknwn ieekdgktai lrqrqnldyn yysvpiqikd rhglvathml
    661    tvrvcdcstp secrmkdkst rdvrpnvilg rwailamvlg svllcilft cfcvtakrtv
    721    kkcfpediaq qnlivsnteg pgeevteani rlpmqtsnic dtsmsvgtvg gqgiktqqsf
    781    emvkggytld snkgghhqtl esvkgvgqgd tgryaytdwq sftqprlgee sirghtlikn
```

Gene ID:              Y20
Gene symbol:          ITGA6
Gene description:     Integrin alpha-6
Unigene:              Hs.133397
Genbank:              X59512
Entrez Gene:          3655
Refseq:               NM_000210 | NM_001079818
Protein sequence isoform b (SEQ ID NO (90)):

```
      1    maaagqlcll ylsagllsrl gaafnldtre dnvirkygdp gslfgfslam hwqlqpedkr
     61    lllvgaprae alplqranrt gglyscdita rgpctriefd ndadptsesk edqwmgvtvq
    121    sqgpggkvvt cahryekrqh vntkqesrdi fgrcyvlsqn lrieddmdgg dwsfcdgrlr
    181    ghekfgscqq gvaatftkdf hyivfgapgt ynwkgivrve qknntffdmn ifedgpyevg
    241    getehdeslv pvpansylgf sldsgkgivs kdeithsga pranhsgavv llkrdmksah
    301    llpehifdge glassfgydv avvdlnkdgw qdivigapqy fdrdgevgga vyvymnqqgr
    361    wnnvkpirln gtkdsmfgia vknigdinqd gypdiavgap yddlgkvfiy hgsangintk
    421    ptqvlkgisp yfgysiagnm dldrnsypdv avgslsdsvt ifrsrpvini qktitvtpnr
    481    idlrqktacg apsgiclqvk scfeytanpa gynpsisivg tleaekerrk sglssrvqfk
    541    nqgsepkytq eltlkrqkqk vcmeetlwlq dnirdklrpi pitasveiqe pssrrrvnsl
    601    pevlpilnsd epktahidvh flkegcgddn vensnlkley kfctregnqd kfsylpiqkg
    661    vpelvlkdqk dialeitvtn spsnprnptk dgddaheakl iatfpdtlty sayrelrafp
    721    ekqlscvanq ngsqadcelg npfkrnsnvt fylvlsttev tfdtpdldin lkettsnqd
    781    nlapitakak vvielllsvs gvakpsqvyf ggtvvgeqam ksedevgsli eyefrvinlg
    841    kpltnlgtat lniqwpkeis ngkwllylvk veskglekvt cepqkeinsl nlteshnsrk
    901    kreitekqid dnrkfslfae rkyqtlncsv nvncvnircp lrgldskasl ilrsrlwnst
    961    fleeysklny ldilmrafid vtaaaenirl pnagtqvrvt vfpsktvaqy sgvpwwiilv
   1021    ailagilmla llvfilwkcg ffkrnkkdhy datyhkaeih aqpsdkerlt sda
```

Protein sequence isoform a (SEQ ID NO (91)):

```
      1    maaagqlcll ylsagllsrl gaafnldtre dnvirkygdp gslfgfslam hwqlqpedkr
     61    lllvgaprae alplqranrt gglyscdita rgpctriefd ndadptsesk edqwmgvtvq
    121    sqgpggkvvt cahryekrqh vntkqesrdi fgrcyvlsqn lrieddmdgg dwsfcdgrlr
    181    ghekfgscqq gvaatftkdf hyivfgapgt ynwkgivrve qknntffdmn ifedgpyevg
    241    getehdeslv pvpansylgf sldsgkgivs kdeitfvsga pranhsgavv llkrdmksah
    301    llpehifdge glassfgydv avvdlnkdgw qdivigapqy fdrdgevgga vyvymnqqgr
```

TABLE 2-continued

```
       361  wnnvkpirln  gtkdsmfgia  vknigdinqd  gypdiavgap  yddlgkvfiy  hgsangintk
       421  ptqvlkgisp  yfgysiagnm  dldrnsypdv  avgslsdsvt  ifrsrpvini  qktitvtpnr
       481  idlrqktacg  apsgiclqvk  scfeytanpa  gynpsisivg  tleaekerrk  sglssrvqfr
       541  nqgsepkytq  eltlkrqkqk  vcmeetlwlq  dnirdklrpi  pitasveiqe  pssrrnvnsl
       601  pevlpilnsd  epktahidvh  flkegcgddn  vcnsnlkley  kfctregnqd  kfsylpiqkg
       661  vpelvlkdqk  dialeitvtn  spsnprnptk  dgddaheakl  iatfpdtlty  sayrelrafp
       721  ekqlscvanq  ngsqadcelg  npfkrnsnvt  fylvlsttev  tfdtpdldin  lklettsnqd
       781  nlapitakak  vviellllsys  gvakpsqvyf  ggtvvgeqam  ksedevgsli  eyefrvinlg
       841  kpltnlgtat  lniqwpkeis  ngkwllylvk  veskglekvt  cepqkeinsl  nlteshnsrk
       901  kreitekqid  dnrkfslfae  rkyqtlncsv  nvncvnircp  lrgldskasl  ilrsrlwnst
       961  fleeyskliny  ldilmrafid  vtaaaenirl  pnagtqvrvt  vfpsktvaqy  sgvpwwiilv
      1021  ailagilmla  llvfilwkcg  ffkrsrydds  vpryhavrir  keereikdek  yidnlekkqw
      1081  itkwnenesy  s
```

Gene ID: Y21
Gene symbol: ITGB4
Gene description: Integrin beta-4
Unigene: Hs.632226
Genbank: X53587 | X51841 | X52186
Entrez Gene: 3691
Refseq: NM_000213 | NM_001005619 | NM_001005731
Protein sequence isoform 1 (SEQ ID NO (92)):

```
         1  magprpspwa  rlllaalisv  slsgtlanrc  kkapvksctc  cvrvdkdcay  ctdemfrdrr
        61  cntqaellaa  gcqresivvm  essfqiteet  qidttlrrsq  mspqglrvrl  rpgeerhfel
       121  evfeplespv  dlyilmdfsn  smsddldnlk  kmgqnlarvl  sqltsdytig  fgkfvdkvsv
       181  pqtdmrpekl  kepwpnsdpp  fsfknvislt  edvdefrnkl  qgerisgnld  apeggfdail
       241  qtavctrdig  wrpdsthllv  fstesafhye  adganvlagi  msrnderchl  dttgtytqyr
       301  tqdypsvptl  vrllakhnii  pifavtnysy  syyeklhtyf  pvsslgvlqe  dssnivelle
       361  eafnrirsnl  diraldsprg  lrtevtskmf  qktrtgsfhi  rrgevgiyqv  qlralehvdg
       421  thvcqlpedq  kgnihlkpsf  sdglkmdagi  icdvctcelq  kevrsarcsf  ngdfvcgqcv
       481  csegwsgqtc  ncstgslsdi  qpclregedk  pcsgrgecqc  ghcvcygegr  yegqfceydn
       541  fqcprtsgfl  cndrgrcsmg  qcvcepgwtg  psdcdplsna  tcidsnggic  ngrghcecgr
       601  chchqqslyt  dticeinysa  ihpglcedlr  scvqcqawgt  gekkgrtcee  cnfkvkmvde
       661  lkraeevvvr  csfrdeddde  tysyytmegdg  apgpnstvlv  hkkkdcppgs  fwwliplll
       721  llpllalll  lcwkycacck  aclallpccn  rghmvgfked  hymlrenlma  sdhldtpmlr
       781  sgnlkgrdvv  rwkvtnnmqr  pgfathaasi  nptelvpygl  slrlarlcte  nllkpdtrec
       841  aqlrqeveen  lnevyrqisg  vhklqqtkfr  qqpnagkkqd  htivdtvlma  prsakpallk
       901  ltekqveqra  fhdlkvapgy  ytltadqdar  gmvefqegve  lvdvrvplfi  rpedddekql
       961  lveaidvpag  tatlgrrlvn  itiikeqard  vvsfeqpefs  vsrgdqvari  pvirrvldgg
      1021  ksqvsyrtqd  gtaggnrdyi  pvegellfqp  geawkelqvk  llelqevdsl  lrgrqvrrfh
      1081  vqlsnpkfga  hlgqphstti  iirdpdeldr  sftsqmlssq  ppphgdlgap  qnpnakaags
      1141  rkihfnwlpp  sgkpmgyrvk  ywiqgdsese  ahlldskvps  veltnlypyc  dyemkvcayg
      1201  aqgegpyssl  vscrthqevp  sepgrlafnv  vsstvtqlsw  aepaetngei  tayevcyglv
      1261  nddnrpigpm  kkvlvdnpkn  rmllienlre  sqpyrytvka  rngagwgper  eaiinlatqp
      1321  krpmsipiip  dipivdaqsg  edydsflmys  ddvlrspsgs  qrpsvsddtg  cgwkfepllg
      1381  eeldlrrvtw  rlppeliprl  sassgrssda  eaphgppddg  gaggkggslp  rsatpgppge
      1441  hlvngrmdfa  fpgstnslhr  mttttsaayg  thlsphvphr  vlstssstltr  dynsltrseh
      1501  shsttlprdy  stltsvsshd  srltagvpdt  ptrlvfsalg  ptslrvswqe  prcerplqgy
      1561  sveyqllngg  elhrlnipnp  aqtsvvvedl  lpnhsyvfrv  raqsqegwgr  eregvities
      1621  qvhpqsplcp  lpgsaftlst  psapgplvft  alspdslqls  werprrpngd  ivgylvtcem
      1681  aqgggpataf  rvdgdspesr  ltvpglsenv  pykfkvqart  tegfgpereg  iitiesqdgg
      1741  pfpqlgsrag  lfqhplqsey  ssitttthtsa  tepflvdglt  lgaqhleagg  sltrhvtqef
      1801  vsrtlttsgt  lsthmdqqff  qt
```

Protein sequence isoform 2 (SEQ ID NO (93)):

```
         1  magprpspwa  rlllaalisv  slsgtlanrc  kkapvksctc  cvrvdkdcay  ctdemfrdrr
        61  cntqaellaa  gcqresivvm  essfqiteet  qidttlrrsq  mspqglrvil  rpgeerhfel
       121  evfeplespv  dlyilmdfsn  smsddldnlk  kmgqnlarvl  sqltsdytig  fgkfvdkvsv
       181  pqtdmrpekl  kepwpnsdpp  fsfknvislt  edvdefrnkl  qgerisgnld  apeggfdail
       241  qtavctrdig  wrpdsthllv  fstesafhye  adganvlagi  msrnderchl  dttgtytqyr
       301  tqdypsvptl  vrllakhnii  pifavtnysy  syyeklhtyf  pvsslgvlqe  dssnivelle
       361  eafnrirsnl  diraldsprg  lrtevtskmf  qktrtgsfhi  rrgevgiyqv  qlralehvdg
       421  thvcqlpedq  kgnihlkpsf  sdglkmdagi  icdvctcelq  kevrsarcsf  ngdfvcgqcv
       481  csegwsgqtc  ncstgslsdi  qpclregedk  pcsgrgecqc  ghcvcygegr  yegqfceydn
       541  fqcprtsgfl  cndrgrcsmg  qcvcepgwtg  psdcdplsna  tcidsnggic  ngrghcecgr
       601  chchqqslyt  dticeinysa  ihpglcedlr  scvqcqawgt  gekkgrtcee  cnfkvkmvde
       661  lkraeevvvr  csfrdeddde  tysyytmegdg  apgpnstvlv  hkkkdcppgs  fwwliplll
       721  llpllalll  lcwkycacck  aclallpccn  rghmvgfked  hymlrenlma  sdhldtpmlr
       781  sgnlkgrdvv  rwkvtnnmqr  pgfathaasi  nptelvpygl  slrlarlcte  nllkpdtrec
       841  aqlrqeveen  lnevyrqisg  vhklqqtkfr  qqpnagkkqd  htivdtvlma  prsakpallk
       901  ltekqveqra  fhdlkvapgy  ytltadqdar  gmvefqegve  lvdvrvplfi  rpedddekql
       961  lveaidvpag  tatlgrrlvn  itiikeqard  vvsfeqpefs  vsrgdqvari  pvirrvldgg
      1021  ksqvsyrtqd  gtaggnrdyi  pvegellfqp  geawkelqvk  llelqevdsl  lrgrqvrrfh
      1081  vqlsnpkfga  hlgqphstti  iirdpdeldr  sftsqmlssq  ppphgdlgap  qnpnakaags
      1141  rkihfnwlpp  sgkpmgyrvk  ywiqgdsese  ahlldskvps  veltnlypyc  dyemkvcayg
      1201  aqgegpyssl  vscrthqevp  sepgrlafnv  vsstvtqlsw  aepaetngei  tayevcyglv
      1261  nddnrpigpm  kkvlvdnpkn  rmllienlre  sqpyrytvka  rngagwgper  eaiinlatqp
      1321  krpmsipiip  dipivdaqsg  edydsflmys  ddvlrspsgs  qrpsvsddte  hlvngrmdfa
      1381  fpgstnslhr  mttttsaayg  thlsphvphr  vlstssstltr  dynsltrseh  shsttlprdy
      1441  stltsvsshg  lppiwehgrs  rlplswalgs  rsraqmkgfp  psrgprdsii  lagrpaapsw
```

TABLE 2-continued

```
      1501  gpdsrltagv  pdtptrlvfs  algptslrvs  wqeprcerpl  qgysveyqll  nggelhrini
      1561  pnpaqtsvvv  edllpnhsyv  frvraqseg   wgreregvit  iesqvhpqsp  lcplpgsaft
      1621  lstpsapgpl  vftalspdsl  qlswerprrp  ngdivgylvt  cemaqgggpa  tafrvdgdsp
      1681  esrltvpgls  envpykfkvq  arttegfgpe  regiitiesq  dggpfpqlgs  raglfqhplq
      1741  seyssitttth tsatepflvd  gltlgaqhle  aggsltrhvt  qefvsrtltt  sgtlsthmdq
      1801  qffqt Protein sequence isoform 3 (SEQ ID NO (94)):
         1  magprpspwa  rlllaalisv  slsgtlanrc  kkapvksctc  cvrvdkdcay  ctdemfrdrr
        61  cntqaellaa  gcqresivvm  essfqiteet  qidttlrrsq  mspqglrvrl  rpgeerhfel
       121  evfeplespv  dlyilmdfsn  smsddldnlk  kmgqnlarvl  sqltsdytig  fgkfvdkvsv
       181  pqtdmrpekl  kepwpnsdpp  fsfknvislt  edvdefrnkl  qgerisgnld  apeggfdail
       241  qtavctrdig  wrpdsthllv  fstesafhye  adganvlagi  msrndcrchl  dttgtytqyr
       301  tqdypsvptl  vrllakhnii  pifavtnysy  syyeklhtyf  pvsslgvlqe  dssnivelle
       361  eafnrirsnl  diraldsprg  lrtevtskmf  qktrtgsfhi  rrgevgiyqv  qlralehvdg
       421  thvcqlpedq  kgnihlkpsf  sdglkmdagi  icdvctcelq  kevrsarcsf  ngdfvcgqcv
       481  csegwsgqtc  ncstgslsdi  qpclregedk  pcsgrgecqc  ghcvcygegr  yegqfceydn
       541  fqcprtsgfl  cndrgrcsmg  qcvcepgwtg  pscdcplsna  tcidsnggic  ngrghcecgr
       601  chchqqslyt  dticeinysa  ihpglcedlr  scvqcqawgt  gekkgrtcee  cnfkvkmvde
       661  lkraeevvvr  csfrdeddc  tysytmegdg  apgpnstvlv  hkkkdcppgs  fwwliplll
       721  llpllalll   lcwkycacck  aclallpccn  rghmvgfked  hymlrenlma  sdhldtpmlr
       781  sgnlkgrdvv  rwkvtnnmqr  pgfathaasi  nptelvpygl  slrlarlcte  nllkpdtrec
       841  aqlrqeveen  lnevyrqisg  vhklqqtkfr  qqpnagkkqd  htivdtvlma  prsakpallk
       901  ltekqveqra  fhdlkvapgy  ytltadqdar  gmvefqegve  lvdvrvplfi  rpedddekql
       961  lveaidvpag  tatlgrrlvn  itiikeqard  vvsfeqpefs  vsrgdqvari  pvirrvldgg
      1021  ksqvsyrtqd  gtaqgnrdyi  pvegellfqp  geawkelqvk  llelqevdsl  lrgrqvrrfh
      1081  vqlsnpkfga  hlgqphstti  iirdpdeldr  sftsqmlssq  ppphgdlgap  qnpnakaags
      1141  rkihfnwlpp  sgkpmgyrvk  ywiqgdsese  ahlldskvps  veltnlypyc  dyemkvcayg
      1201  aqgegpyssl  vscrthqevp  sepgrlafnv  vsstvtqlsw  aepaetngei  tayevcyglv
      1261  nddnrpigpm  kkvlvdnpkn  rmllienlre  sqpyrytvka  rngagwgper  eaainlatqp
      1321  krpmsipiip  dipivdaqsg  edydsflmys  ddvlrspsgs  qrpsysddte  hlvngrmdfa
      1381  fpgstnslhr  mtttsaaayg  thlsphvphr  vlstssstltr dynsltrseh  shsttlprdy
      1441  stltsysshd  srltagvpdt  ptrlvfsalg  ptslrvswqe  prcerplqgy  sveyqllngg
      1501  elhrlnipnp  aqtsvvvedl  lpnhsyvfrv  raqsqegwgr  eregvities  qvhpqsplcp
      1561  lpgsaftlst  psapgplvft  alspdslqls  werprrpngd  ivgylvtcem  aqgggpataf
      1621  rvdgdspesr  ltvpglsenv  pykfkvqart tegfgpereg  iitiesqdgg  pfpqlgsrag
      1681  lfqhplqsey  ssittthtsa  tepflvdglt  lgaqhleagg  sltrhvtqef  vsrtlttsgt
      1741  lsthmdqqff  qt Gene ID:             Y22
Gene symbol:         PVRL4
Gene description:    Poliovirus receptor-related protein 4
Unigene:             Hs.492490
Genbank:             BC010423
Entrez Gene:         81607
Refseq:              NM_030916
Protein sequence (SEQ ID NO (95)):
         1  mplslgaemw  gpeawlllll  llasftgrcp  ageletsdvv  tvvlgqdakl  pcfyrgdsge
        61  qvgqvawarv  dagegaqela  llhskyglhv  spayegrveq  ppppprnpldg  svllrnavqa
       121  degeyecrvs  tfpagsfqar  lrlrvlvppl  pslnpgpale  egqgltlaas  ctaegspaps
       181  vtwdtevkgt  tssrsfkhsr  saavtsefhl  vpsrsmngqp  ltcvvshpgl  lqdqrithil
       241  hvsflaeasv  rgledqnlwh  igregamlkc  lsegqpppsy  nwtrldgplp  sgvrvdgdtl
       301  gfppltttehs giyvchvsne  fssrdsqvtv  dvldpqedsg  kqvdlvsasv  vvvgviaall
       361  fcllvvvvl   msryhrrkaq  qmtqkyeeel  tltrensirr  lhshhtdprs  qpeesvglra
       421  eghpdslkdn  sscsvmseep  egrsystltt  vreietqtel  lspgsgraee  eedqdegikq
       481  amnhfvqeng  tlrakptgng  iyingrghlv Gene ID:             Y23
Gene symbol:         SDC1
Gene description:    Syndecan-1
Unigene:             Hs.224607
Genbank:             BC008765
Entrez Gene:         6382
Refseq:              NM_001006946
Protein sequence (SEQ ID NO (96)):
         1  mrraalwlwl  calalslqpa  lpqivatnlp  pedqdgsgdd  sdnfsgsgag  alqditlsqq
        61  tpstwkdtql  ltaiptspep  tgleataast  stlpagegpk  egeavvlpev  epgltareqe
       121  atprprettq  lptthqastt  tattaqepat  shphrdmqpg  hhetstpagp  sqadlhtpht
       181  edggpsater  aaedgassql  paaegsgeqd  ftfetsgent  avvavepdrr  nqspvdqgat
       241  gasqglldrk  evlggviagg  lvglifavel  vgfmlyrmkk  kdegsyslee  pkqanggayq
       301  kptkqeefya
```

TABLE 2-continued

```
Gene ID:            Z1
Gene symbol:        ENPP1
Gene description:   Ectonucleotide pyrophosphatase/ phosphodiesterase family member 1
Unigene:            Hs.527295
Genbank:            BC059375
Entrez Gene:        5167
Refseq:             NM_006208
Protein sequence (SEQ ID NO (97)):
      1   merdgcaggg srggeggrap regpagngrd rgrshaaeap gdpqaaasll apmdvgeepl
     61   ekaarartak dpntykvlsl vlsvcvltti lgcifglkps cakevksckg rcfertfgnc
    121   rcdaacvelg nccldyqetc iepehiwtcn kfrcgekrlt rslcacsddc kdkgdcciny
    181   ssvcqgeksw veepcesine pqcpagfetp ptllfsldgf raeylhtwgg llpvisklkk
    241   cgtytknmrp vyptktfpnh ysivtglype shgiidnkmy dpkmnasfsl kskekfnpew
    301   ykgepiwvta kyqglksgtf fwpgsdvein gifpdiykmy ngsvpfeeri lavlqwlqlp
    361   kderphfytl yleepdsssgh sygpvssevi kalqrvdgmv gmlmdglkel nlhrclnlil
    421   isdhgmeqgs ckkyiylnky lgdvknikvi ygpaarlrps dvpdkyysfn yegiarnlsc
    481   repnqhfkpy lkhflpkrlh faksdriepl tfyldpqwql alnpserkyc gsgfhgsdnv
    541   fsnmqalfvg ygpgfkhgie adtfenievy nlmcdllnlt papnngthgs lnhllknpvy
    601   tpkhpkevhp lvqcpftrnp rdnlgcscnp silpiedfqt qfnltvaeek iikhetlpyg
    661   rprvlqkent icllsqhqfm sgysqdilmp lwtsytvdrn dsfstedfsn clyqdfripl
    721   spvhkcsfyk nntkvsygfl sppqlnknss giyseallttt nivpmyqsfq viwryfhdtl
    781   lrkyaeerng vnvvsgpvfd fdydgrcdsl enlrqkrrvi rnqeilipth ffivltsckd
    841   tsqtplhcen ldtlafilph rtdnsescvh gkhdsswvee llmlhrarit dvehitglsf
    901   yqqrkepvsd ilklkthlpt fsqed Gene ID:            Z2
Gene symbol:        CD34
Gene description:   Hematopoietic progenitor cell antigen CD34
Unigene:            Hs.374990
Genbank:            M81104
Entrez Gene:        947
Refseq:             NM_001773 | NM_001025109
Protein sequence isoform b (SEQ ID NO (98)):
      1   mlvrrgarag prmprgwtal cllsllpsgf msldnngtat pelptqgtfs nvstnvsyqe
     61   tttpstlgst slhpvsqhgn eattnitett vkftstsvit svygntnssv qsqtsvistv
    121   fttpanvstp ettlkpslsp gnvsdlstts tslatsptkp ytsssspilsd ikaeikcsgi
    181   revkltqgic leqnktssca efkkdrgegl arvlcgeeqa dadagaqvcs lllaqsevrp
    241   qclllvlanr teissklqlm kkhqsdlkkl gildfteqdv ashqsysqkt lialvtsgal
    301   lavlgitgyf lmnrrswspt gerlelep Protein sequence isoform a (SEQ ID NO (99)):
      1   mlvrrgarag prmprgwtal cllsllpsgf msldnngtat pelptqgtfs nvstnvsyqe
     61   tttpstlgst slhpvsqhgn eattnitett vkftstsvit svygntnssv qsqtsvistv
    121   fttpanvstp ettlkpslsp gnvsdlstts tslatsptkp ytsssspilsd ikaeikcsgi
    181   revkltqgic leqnktssca efkkdrgegl arvlcgeeqa dadagaqvcs lllaqsevrp
    241   qclllvlanr teissklqlm kkhqsdlkkl gildfteqdv ashqsysqkt lialvtsgal
    301   lavlgitgyf lmnrrswspt gerlgedpyy tengggqgys sgpgtspeaq gkasvnrgaq
    361   engtgqatsr nghsarqhvv adtel Gene ID:            Z3
Gene symbol:        JAM3
Gene description:   Junctional adhesion molecule C
Unigene:            Hs.150718
Genbank:            BC012147
Entrez Gene:        83700
Refseq:             NM_032801 | NM_001205329
Protein sequence isoform 1 (SEQ ID NO (100)):
      1   malrrpprlr lcarlpdffl lllfrgclig avnlkssnrt pvvqefesve lsciitdsqt
     61   sdpriewkki qdeqttyvff dnkiqgdlag raeilgktsl kiwnvtrrds alyrcevvar
    121   ndrkeideiv ieltvqvkpv tpvcrvpkav pvgkmatlhc qeseghprph yswyrndvpl
    181   ptdsranprf rnssfhlnse tgtlvftavh kddsgqyyci asndagsarc eeqemevydl
    241   niggiiggvl vvlavlalit lgiccayrrg yfinnkqdge syknpgkpdg vnyirtdeeg
    301   dfrhkssfvi Protein sequence isoform 2 (SEQ ID NO (101)):
      1   malrrpprlr lcarlpdffl lllfrgclig avnlkssnrt pvvqefesve lsciitdsqt
     61   sdpriewkki qdeqttyvff dnkiqvkpvt pvcrvpkavp vgkmatlhcq eseghprphy
    121   swyrndvplp tdsranprfr nssfhlnset gtlvftavhk ddsgqyycia sndagsarce
    181   eqemevydln iggiiggvlv vlavlalitl giccayrrgy finnkqdges yknpgkpdgv
    241   nyirtdeegd frhkssfvi
```

TABLE 2-continued

```
Gene ID:            Z4
Gene symbol:        CD14
Gene description:   Monocyte differentiation antigen CD14
Unigene:            Hs.163867
Genbank:            BC010507
Entrez Gene:        929
Refseq:             NM_000591
Protein sequence (SEQ ID NO (102)):
         1    merascllll llplvhvsat tpepceldde dfrcvcnfse pqpdwseafq cvsaveveih
        61    agglnlepfl krvdadadpr qyadtvkalr vrrltvgaaq vpaqllvgal rvlaysrlke
       121    ltledlkitg tmpplpleat glalsslrlr nvswatgrsw laelqqwlkp glkvlsiaqa
       181    hspafsceqv rafpaltsld lsdnpglger glmaalcphk fpaiqnlalr ntgmetptgv
       241    caalaaagvq phsldlshns lratvnpsap rcmwssalns lnlsfagleq vpkglpaklr
       301    vldlscnrln rapqpdelpe vdnltldgnp flvpgtalph egsmnsgvvp acarstlsvg
       361    vsgtlvllqg argfa Gene ID:            Z5
Gene symbol:        PLSCR4
Gene description:   Phospholipid scramblase 4
Unigene:            Hs.477869
Genbank:            AF199023
Entrez Gene:        57088
Refseq:             NM_001128304 | NM_001128306 | NM_001177304
Protein sequence isoform a (SEQ ID NO (103)):
         1    msgvvptape qpagemenqt kppdprpdap peynshflpg ppgtavpppt gypgglpmgy
        61    yspqqpstfp lyqpvggihp vryqpgkypm pnqsvpitwm pgptpmancp pgleylvqld
       121    nihvlqhfep lemmtcfetn nrydiknnsd qmvyivtedt ddftrnayrt lrpfvlrvtd
       181    cmgreimtmq rpfrctcccf ccpsarqele vqcppgvtig fvaehwnlcr avysiqnekk
       241    envmrvrgpc stygcgsdsv fevksldgis nigsiirkwn gllsamadad hfdihfpldl
       301    dvkmkamifg acflidfmyf ersppqrsr Protein sequence isoform b (SEQ ID NO (104)):
         1    msgvvptape qpagemenqt kppdprpdap peynshflpg ppgtavpppt gypgglpmgy
        61    yspqqpstfp lyqpvggihp vryqpgkypm pnqsvpitwm pgptpmancp pgleylvqle
       121    vqcppgvtig fvaehwnlcr avysiqnekk envmrvrgpc stygcgsdsv fevksldgis
       181    nigsiirkwn gllsamadad hfdihfpldl dvkmkamifg acflidfmyf ersppqrsr Protein sequence isoform c (SEQ ID NO (105)):
         1    menqtkppdp rpdappeyns hflpgppgta vppptgypgg lpmgyyspqq pstfplyqpv
        61    ggihpvryqp gkypmpnqsv pitwmpgptp mancppgley lvqlevqcpp gvtigfvaeh
       121    wnlcravysi qnekkenvmr vrgpcstygc gsdsvfevks ldgisnigsi irkwngllsa
       181    madadhfdih fpldldvkmk amifgacfli dfmyferspp qrsr Gene ID:            Z6
Gene symbol:        AMOT
Gene description:   angiomotin
Unigene:            Hs.528051
Genbank:            AF286598
Entrez Gene:        154796
Refseq:             NM_133265 | NM_001113490
Protein sequence isoform 2 (SEQ ID NO (106)):
         1    mpraqpssas yqpvpadpfa ivsraqqmve ilsdenrnlr qelegcyekv arlqkvetei
        61    qrvseayenl vksssskreal ekamrnkleg eirrmhdfnr dlrerletan kqlaekeyeg
       121    sedtrktisq lfaknkesqr ekekleaela tarstnedqr rhieirdqal snaqakvvkl
       181    eeelkkkqvy vdkvekmqqa lvqlqaacek reqlehrlrt rlereleslr iqqrqgncqp
       241    tnvseynaaa lmellrekee rilaleadmt kweqkyleen vmrhfaldaa atvaaqrdtt
       301    vishspntsy dtaleariqk eeeeilmank rcldmegrik tlhaqiiekd amikvlqqrs
       361    rkepskteql scmrpakslm sisnagsgll shsstltgsp imeekrddks wkgslgillg
       421    gdyraeyvps tpspvppstp llsahsktgs rdcstqterg tesnktaava pisvpapvaa
       481    aataaaitat aatitttmva aapvavaaaa apaaaaapsp ataaataaav spaaagqipa
       541    aasvasaaav apsaaaaaav qvapaapapv papalvpvpa paaaqasapa qtqaptsapa
       601    vaptpaptpt pavaqaevpa spatgpgphr lsipsltcnp dktdgpvfhs ntlerktpiq
       661    ilgqepdaem veyli Protein sequence isoform 1 (SEQ ID NO (107)):
         1    mrnseeqpsg gttvlqrllq eqlrygnpse nrsllaihqq atgngppfps gsgnpgpqsd
        61    vlspqdhhqq lvahaarqep qggeiqsenl imekqlsprm qnneelptye eakvkqgyvg
       121    gqqhasvgaa fyvtgvtnqk mrtegrpsvq rlnpgkmhqd eglrdlkqgh vrslserlmq
       181    mslatsgvka hppvtsapls ppqpndlykn ptsssefyka qgplpnqhsl kgmehrgppp
       241    eypfkgmppq svvckpqepg hfysehrlnq pgrteqglmr yqhppeygaa rpaqdislpl
       301    sarnsqphsp tssltsggsl pllqspppstr lsparhplvp nqgdhsahlp rpqqhflpnq
       361    ahqgdhyrls qpglsqqqqq qqqqhhhhh hqqqqqqqpq qqpgeaysam praqpssasy
       421    qpvpadpfai vsraqqmvei lsdenrnlrq elegcyekva rlqkveteiq rvseayenlv
       481    ksssskreale kamrnklege irrmhdfnrd lrerletank qlaekeyegs edtrktisql
       541    faknkesqre kekleaelat arstnedqrr hieirdqaln aqakvvkle eelkkkqvyv
       601    dkvekmqqal vqlqaacekr eqlehrlrtr lereleslri qqrqgncqpt nvseynaaal
       661    mellrekeer ilaleadmtk weqkyleenv mrhfaldaaa tvaaqrdtti ishspntsyd
       721    taleariqke eeeilmankr cldmegrikt lhaqiiekda mikvlqqrsr kepskteqls
       781    cmrpakslms isnagsglls hsstltgspi meekrddksw kgslgillgg dyraeyvpst
       841    pspvppstpl lsahsktgsr dcstqtergt esnktaavap isvpapvaaa ataaaitata
```

TABLE 2-continued

```
       901    atitttmvaa  apvavaaaaa  paaaaapspa  taaataaavs  paaagqipaa  asvasaaava
       961    psaaaaaavq  vapaapapvp  apalvpvpap  aaaqasapaq  tqaptsapav  aptpaptptp
      1021    avaqaevpas  patgpgphrl  sipsltcnpd  ktdgpvfhsn  tlerktpiqi  lgqepdaemv
      1081    eyli
```

Gene ID:            Z7
Gene symbol:        ENPEP
Gene description:   glutamyl aminopeptidase (aminopeptidase A)
Unigene:            Hs.435765
Genbank:            L12468
Entrez Gene:        2028
Refseq:             NM_001977
Protein sequence (SEQ ID NO (108)):

```
         1    mnfaeregsk  ryciqtkhva  ilcavvvgvg  livglavglt  rscdssgdgg  pgtapapshl
        61    psstaspsgp  paqdqdicpa  sedesgqwkn  frlpdfvnpv  hydlhvkpll  eedtytgtvs
       121    isinlsaptr  ylwlhlretr  itrlpelkrp  sgdqvqvrrc  feykkqeyvv  veaeeeltps
       181    sgdglylltm  efagwlngsl  vgfyrttyte  ngqvksivat  dheptdarks  fpcfdepnkk
       241    atytisithp  keygalsnmp  vakeesvddk  wtrttfeksv  pmstylvcfa  vhqfdsvkri
       301    snsgkpltiy  vqpeqkhtae  yaanitksvf  dyfeeyfamn  yslpkldkia  ipdfgtgame
       361    nwglityret  nllydpkesa  ssnqqrvatv  vahelvhqwf  gnivtmdwwe  dlwlnegfas
       421    ffeflgvnha  etdwqmrdqm  lledvlpvqe  ddslmsshpi  ivtvttpdei  tsvfdgisys
       481    kgssilrmle  dwikpenfqk  gcqmylekyq  fknaktsdfw  aaleeasrlp  vkevmdtwtr
       541    qmgypvlnvn  gvknitqkrf  lldpranpsq  ppsdlgytwn  ipvkwtedni  tssvlfnrse
       601    kegitlnssn  psgnaflkin  pdhigfyrvn  yevatwdsia  talslnhkif  ssadraslid
       661    dafalaraql  ldykvalnlt  kylkreenfl  pwqrvisavt  yiismfeddk  elypmieeyf
       721    qgqvkpiads  lgwndagdhv  tkllrssvlg  fackmgdrea  lnnasslfeq  wlngtvslpv
       781    nlrllvyryg  mqnsgneisw  nytleqyqkt  slaqekekll  yglasvknvt  llsryldllk
       841    dtnliktqdv  ftviryisyn  sygknmawnw  iqlnwdylvn  rytlnnrnlg  rivtiaepfn
       901    telqlwqmes  ffakypqaga  gekpreqvle  tvknniewlk  qhrntirewf  fnllesg
```

Gene ID:            Z8
Gene symbol:        THY1
Gene description:   Thy-1 cell surface antigen
Unigene:            Hs.644697
Genbank:            AP003396
Entrez Gene:        7070
Refseq:             NM_006288
Protein sequence (SEQ ID NO (109)):

```
         1    mnlaisiall  ltvlqvsrgq  kvtsltaclv  dqslrldcrh  entssspiqy  efsltretkk
        61    hvlfgtvgvp  ehtyrsrtnf  tskynmkvly  lsaftskdeg  tytcalhhsg  hsppissqnv
       121    tvlrdklvkc  egisllaqnt  swllllllsl  sllqatdfms  l
```

SEQUENCE LISTING

The patent contains a lengthy sequence listing. A copy of the sequence listing is available in electronic form from the USPTO web site (https://seqdata.uspto.gov/?pageRequest=docDetail&DocID=US11740239B2). An electronic copy of the sequence listing will also be available from the USPTO upon request and payment of the fee set forth in 37 CFR 1.19(b)(3).

What is claimed is:

1. A method of forming a composition enriched with human corneal endothelial cells comprising:

contacting a cell population containing human corneal endothelial cells expressing CD56 or CD166 with a first positive affinity reagent; and selecting cells to which the first positive affinity reagent is bound, wherein the first positive affinity reagent comprises an antibody that binds to CD56 surface protein expressed on the surface of human corneal endothelial cells, an antibody that binds to CD166 surface protein expressed on the surface of human corneal endothelial cells, an antibody that binds to coxsackievirus and adenovirus receptor (CAR) surface protein expressed on the surface of human corneal endothelial cells, or an antibody that binds to CD248 surface protein expressed on the surface of human corneal endothelial cells;

wherein the method comprises one or both of:

(i) the human corneal endothelial cells in the cell population express CD56, the first positive affinity reagent comprises an antibody or aptamer that binds to CD248 surface protein expressed on the surface of human corneal endothelial cells, an antibody or aptamer that binds to CAR surface protein expressed on the surface of human corneal endothelial cells, or an antibody or aptamer that binds to CD166 surface protein expressed on the surface of human corneal endothelial cells, and (ii) further comprising:

contacting the cell population containing human corneal endothelial cells with a second positive affinity reagent; and selecting cells to which the second positive affinity reagent is bound;

wherein the second positive affinity reagent differs from the first positive affinity reagent in regard to the identity of at least one surface protein that the first and second positive affinity reagents bind to and the second positive affinity reagent comprises an antibody or aptamer that binds to CD56 surface protein expressed on the surface of human corneal endothelial cells, an antibody or aptamer that binds to CD90 surface protein expressed on the surface of human corneal endothelial cells, an antibody or aptamer that binds to CD166 surface protein expressed on the surface of human corneal endothelial cells, an antibody or aptamer that binds to CD248 surface protein expressed on the surface of human corneal endothelial cells, or an antibody or aptamer that binds to CAR surface protein expressed on the surface of human corneal endothelial cells.

2. The method of claim 1, wherein the human corneal endothelial cells in the cell population express CD56, the first positive affinity reagent comprises an antibody or aptamer that binds to CD248 surface protein expressed on the surface of human corneal endothelial cells, an antibody or aptamer that binds to CAR surface protein expressed on the surface of human corneal endothelial cells, or an antibody or aptamer that binds to CD166 surface protein expressed on the surface of human corneal endothelial cells.

3. The method of claim 2, wherein said first positive affinity reagent comprises an antibody or aptamer that binds to CD166 surface protein expressed on the surface of human corneal endothelial cells.

4. The method of claim 1, further comprising:
contacting the cell population containing human corneal endothelial cells with a second positive affinity reagent; and
selecting cells to which the second positive affinity reagent is bound;
wherein the second positive affinity reagent compositionally differs from the first positive affinity reagent and the second positive affinity reagent comprises an antibody or aptamer that binds to CD56 surface protein expressed on the surface of human corneal endothelial cells, an antibody or aptamer that binds to CD90 surface protein expressed on the surface of human corneal endothelial cells, an antibody or aptamer that binds to CD166 surface protein expressed on the surface of human corneal endothelial cells, an antibody or aptamer that binds to CD248 surface protein expressed on the surface of human corneal endothelial cells, or an antibody or aptamer that binds to CAR surface protein expressed on the surface of human corneal endothelial cells.

5. The method of claim 1, further comprising:
contacting the cell population containing human corneal endothelial cells with a negative affinity reagent that selectively binds to human endothelial cells that have undergone a fibroblastic transformation relative to human corneal endothelial cells; and
removing cells that have undergone a fibroblastic transformation to which the negative affinity reagent is bound.

6. The method of claim 5, wherein the negative affinity reagent comprises an antibody or aptamer that binds to CD109 surface protein expressed on the surface of human corneal endothelial cells.

7. The method of claim 1, wherein the human corneal endothelial cells in the cell population express CD166, the first positive affinity reagent comprises an antibody or aptamer that binds to CD56 surface protein expressed on the surface of human corneal endothelial cells, an antibody or aptamer that binds to CD90 surface protein expressed on the surface of human corneal endothelial cells, an antibody or aptamer that binds to CD248 surface protein expressed on the surface of human corneal endothelial cells, or an antibody or aptamer that binds to CAR surface protein expressed on the surface of human corneal endothelial cells.

8. The method of claim 7, wherein the first positive affinity reagent comprises an antibody or aptamer that binds to CD56 surface protein expressed on the surface of human corneal endothelial cells, an antibody or aptamer that binds to CD248 surface protein expressed on the surface of human corneal endothelial cells, or an antibody or aptamer that binds to CAR surface protein expressed on the surface of human corneal endothelial cells.

9. The method of claim 7, wherein the first positive affinity reagent comprises an antibody or aptamer that binds to CD56 surface protein expressed on the surface of human corneal endothelial cells.

10. A composition enriched with human corneal endothelial cells comprising:
human corneal endothelial cells expressing at least one marker selected from the group consisting of: CD56, CD90, CD166, and coxsackie virus and adenovirus receptor (CAR); and
a first positive affinity reagent, wherein the first positive affinity reagent is an antibody against a surface protein expressed on the surface of human corneal endothelial cells, the surface protein selected from the group consisting of: CD56, CD90, CD166, CD248, and CAR,
wherein the marker expressed on the human corneal endothelial cells and the surface protein detected by the first positive affinity reagent are compositionally different;
wherein at least one of:
(i) the human corneal endothelial cell expresses CD56 and the first positive affinity reagent comprises an antibody or aptamer that binds to CD248 surface protein expressed on the surface of human corneal endothelial cells, an antibody or aptamer that binds to CAR surface proteins expressed on the surface of human corneal endothelial cells, an antibody or aptamer that binds to CD166 surface protein expressed on the surface of human corneal endothelial cells, or an antibody or aptamer that binds to CD90 surface protein expressed on the surface of human corneal endothelial cells and
(ii) the human corneal endothelial cell expresses CD56 and the first positive affinity reagent comprises an antibody or aptamer that binds to CD248 surface protein expressed on the surface of human corneal endothelial cells, an antibody or aptamer that binds to CAR surface protein expressed on the surface of human corneal endothelial cells, or an antibody or aptamer that binds to CD166 surface protein expressed on the surface of human corneal endothelial cells.

11. The composition of claim 10, wherein the human corneal endothelial cell expresses CD56 and the first positive affinity reagent comprises an antibody or aptamer that binds to CD248 surface protein expressed on the surface of human corneal endothelial cells, an antibody or aptamer that binds to CAR surface proteins expressed on the surface of human corneal endothelial cells, an antibody or aptamer that binds to CD166 surface protein expressed on the surface of human corneal endothelial cells, or an antibody or aptamer that binds to CD90 surface protein expressed on the surface of human corneal endothelial cells.

12. The composition of claim 11, wherein the first positive affinity reagent is an antibody or aptamer that binds to CD248 surface protein expressed on the surface of human corneal endothelial cells, an antibody or aptamer that binds to CAR surface protein expressed on the surface of human corneal endothelial cells, or an antibody or aptamer that binds to CD166 surface protein expressed on the surface of human corneal endothelial cells.

13. The composition of claim 12, wherein the first positive affinity reagent is an antibody or aptamer that binds to CD166 surface protein expressed on the surface of human corneal endothelial cells.

14. The composition of claim 10, wherein the composition further comprises a second positive affinity reagent that is compositionally different from the first positive affinity reagent, and the second positive affinity reagent is an antibody or aptamer that binds to CD90 surface protein expressed on the surface of human corneal endothelial cells, an antibody or aptamer that binds to CD166 surface protein expressed on the surface of human corneal endothelial cells, an antibody or aptamer that binds to CD248 surface protein expressed on the surface of human corneal endothelial cells, or an antibody or aptamer that binds to CAR surface protein expressed on the surface of human corneal endothelial cells.

15. The composition of claim 10, wherein the human corneal endothelial cells express CD166 and the first positive affinity reagent is an antibody or aptamer that binds to CD56 surface protein expressed on the surface of human corneal endothelial cells, an antibody or aptamer that binds to CD90 surface protein expressed on the surface of human corneal endothelial cells, an antibody or aptamer that binds to CD248 surface protein expressed on the surface of human corneal endothelial cells, or an antibody or aptamer that binds to CAR surface protein expressed on the surface of human corneal endothelial cells.

16. The composition of claim 15, wherein the first positive affinity reagent is an antibody or aptamer that binds to CD56 surface protein expressed on the surface of human corneal endothelial cells, an antibody or aptamer that binds to CD248 surface protein expressed on the surface of human corneal endothelial cells, or an antibody or aptamer that binds to CAR surface protein expressed on the surface of human corneal endothelial cells.

17. The composition of claim 15, wherein the first positive affinity reagent is an antibody or aptamer that binds to CD56 surface protein expressed on the surface of human corneal endothelial cells.

18. The composition of claim 10, wherein the composition further comprises a second positive affinity reagent that is compositionally different from the first positive affinity reagent, and the second positive affinity reagent is an antibody or aptamer that binds to CD56 surface protein expressed on the surface of human corneal endothelial cells, an antibody or aptamer that binds to CD90 surface protein expressed on the surface of human corneal endothelial cells, an antibody or aptamer that binds to CD248 surface protein expressed on the surface of human corneal endothelial cells, or an antibody or aptamer that binds to CAR surface protein expressed on the surface of human corneal endothelial cells.

19. The composition of claim 18, wherein the positive affinity reagents are coupled to a label.

20. The composition of claim 19, wherein the positive affinity reagents are coupled to different labels.

\* \* \* \* \*